US012679820B2

(12) United States Patent
Lane et al.

(10) Patent No.: US 12,679,820 B2
(45) Date of Patent: *Jul. 14, 2026

(54) COCRYSTALS, PHARMACEUTICAL COMPOSITIONS THEREOF, AND METHODS OF TREATMENT INVOLVING SAME

(71) Applicant: Servier Pharmaceuticals LLC, Boston, MA (US)

(72) Inventors: Benjamin S. Lane, Lynnfield, MA (US); Chong-Hui Gu, Waban, MA (US)

(73) Assignee: Servier Pharmaceuticals LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,859

(22) Filed: Nov. 8, 2023

(65) Prior Publication Data

US 2024/0343705 A1 Oct. 17, 2024

Related U.S. Application Data

(63) Continuation of application No. 17/723,666, filed on Apr. 19, 2022, now Pat. No. 11,851,417, which is a continuation of application No. 16/760,520, filed as application No. PCT/US2018/058930 on Nov. 2, 2018, now Pat. No. 11,345,677.

(60) Provisional application No. 62/580,501, filed on Nov. 2, 2017.

(51) Int. Cl.
*C07D 401/04* (2006.01)
*A61K 45/06* (2006.01)

(52) U.S. Cl.
CPC ............ *C07D 401/04* (2013.01); *A61K 45/06* (2013.01); *C07B 2200/13* (2013.01)

(58) Field of Classification Search
CPC .................................................... C07D 401/04
USPC .......................................................... 544/207
See application file for complete search history.

(56) References Cited

U.S. PATENT DOCUMENTS

2012/0149687 A1 6/2012 Lee et al.
2015/0018328 A1 1/2015 Konteatis et al.

FOREIGN PATENT DOCUMENTS

WO 2013102431 A1 7/2013
WO 2015003640 A1 1/2015

OTHER PUBLICATIONS

U.S. Department of Health an Human Services, Food and Drug Administration, Center for Drug Evaluation and Research (CDER) Regulatory classification of pharmaceutical co-crystals guidance for industry Feb. 2018, https://www.fda.gov/files/drugs/published/Regulatory-Classification-of-Pharmaceutical-Co-Crystals.pdf, retrieved Dec. 15, 2021.
Pharmaceutical Tech. (2006), vol. 30(10), pp. 1-17, particularly pp. 1-3.
Berge, et al., J. Pharmaceutical Sciences, 1977, 66, 1-19.
Dang, L et al., Nature 2009, 462, 739-744.
Geisbrecht et al., J. Biol. Chem., 1999, 274, 30527-30533.
Gerhard et al., The MGC Project Team, Genomes Res., 2004, 14, 2121-2127.
Latini, A. et al., Eur J. Neurosci, 2003, 17, 2017-2022.
Luo et al., J. Chromatogr A., 1147, 153-64, 2007.
Macrae et al., J. Appl. Cryst., 2006, 39, 453-457.
Munger et al., Nat Biotechnol, 2008, 26, 1179-1186.
Nekrutenko et al., Mol. Biol. Evol., 1998, 15, 1674-1684.
Sheldrick G. M., A Short History of SHELX., Acta Crystallogr A., 2008, 64: 112-122.
Sjoeblom et al., Science, 2006, 314, 268-274.
Spek, "Single-Crystal Structure Validation with the Program PLATON," J. Appl. Cryst., 2003, 36, 7-13.
Struys, E.A. et al., Am J. Hum Genet, 2005, 76, 358-360.
Wajner, J. Inherit Metab Dis, 2004, 27, 427-448.
Wiemann et al., Genome Res., 2001, 11, 422-435.
Variankaval N. et al., From Form to Function: Crystallization of Active Pharmaceutical Ingredients, AICHE, vol. 54, No. 7, 1685-1688, (2008).
Caira M. R., Crystalline Polymorphism of Organic Compounds, Topics in Curr. Chemist., vol. 198, pp. 168-208, (1988).
Jagadeesh N., Solubility Advantage of Amorphous Drugs and Pharmaceutical Cocrystals, Published as part of the Crystal Growth & Design 10th Anniversary Perspective, May 18, pp. 2662-2679, (2011).
Aitipamula et al., Polymorphs, Salts, and Cocrystals: What's in a Name?, Cryst. Growth Des., 12, 2147-2152 (2012).
Kazuhide Ashizawa et al., Polymorphism and crystallization of the pharmaceutical drugs, Maruzen Planet Co., Ldt, pp. 305-317 (2002).

*Primary Examiner* — Andrew D Kosar
(74) *Attorney, Agent, or Firm* — GOODWIN PROCTER LLP

(57) ABSTRACT

Provided are solid forms of a compound useful for treating cancer, pharmaceutical compositions thereof, and methods of treating cancer comprising administering the solid forms described herein to a patient in need thereof.

28 Claims, 39 Drawing Sheets

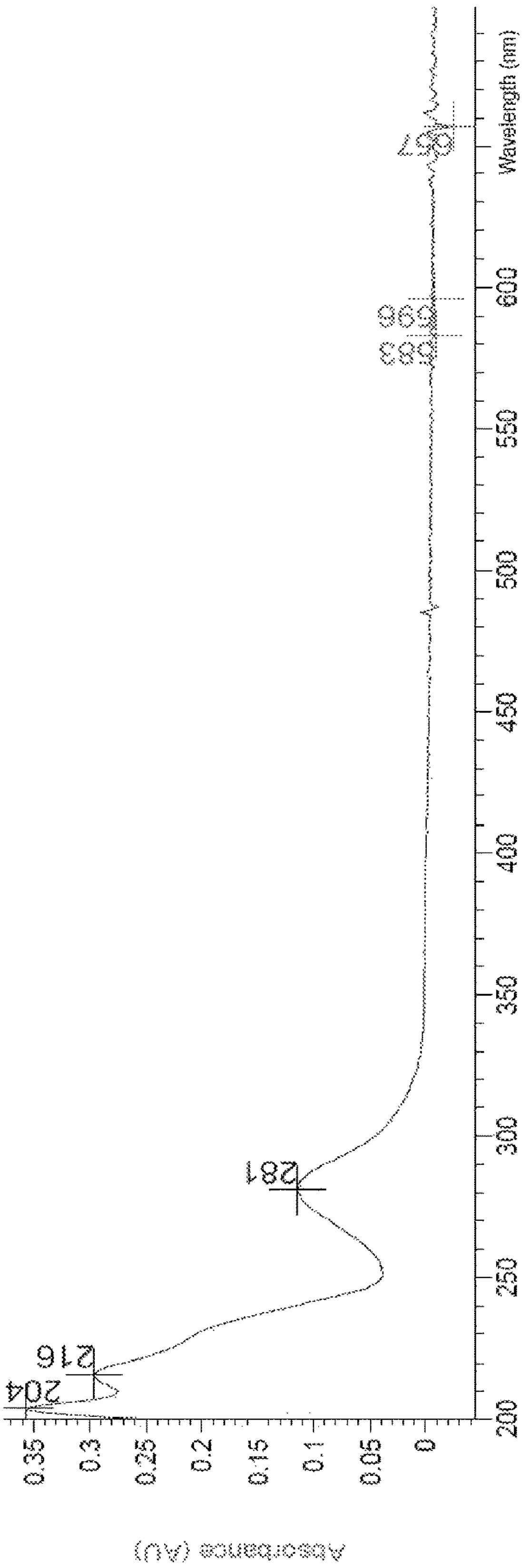
Figure 19
Replacement Sheet
19/39

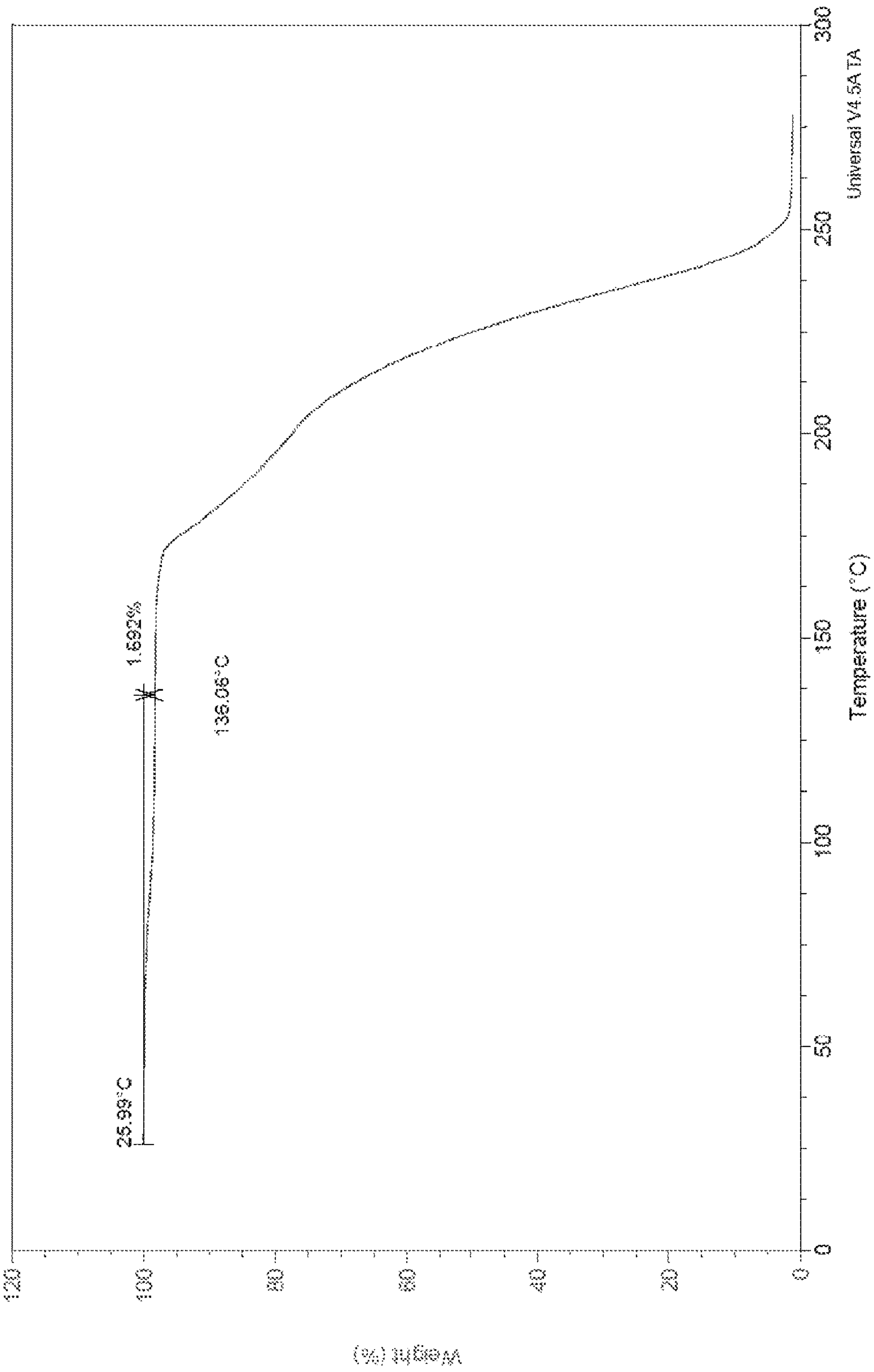
Figure 22
Replacement Sheet
22/39

COCRYSTALS, PHARMACEUTICAL COMPOSITIONS THEREOF, AND METHODS OF TREATMENT INVOLVING SAME

CROSS-REFERENCE TO RELATED APPLICATIONS

This application is a continuation of U.S. patent application Ser. No. 17/723,666, filed Apr. 19, 2022, which is a continuation of U.S. patent application Ser. No. 16/760,520, filed Apr. 30, 2020, now U.S. Pat. No. 11,345,677, which is a National Stage Entry of International Patent Application No. PCT/US2018/058930, filed Nov. 2, 2018, which claims the benefit of U.S. Provisional Patent Application No. 62/580,501, filed Nov. 2, 2017, the disclosures of which are incorporated herein by reference in their entirety.

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2,4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684(1998); Geisbrecht et al., J. Biol. Chem. 274:30527-30533(1999); Wiemann et al., Genome Res. 11:422-435(2001); The MGC Project Team, Genome Res. 14:2121-2127 (2004); Lubec et al., Submitted (December 2008) to UniProtKB; Kullmann et al., Submitted (June 1996) to the EMBL/GenBank/DDBJ databases; and Sjoeblom et al., Science 314:268-274 (2006).

Non-mutant, e.g., wild type, IDH1 catalyzes the oxidative decarboxylation of isocitrate to α-ketoglutarate.

It has been discovered that mutations of IDH1 present in certain cancer cells result in a new ability of the enzyme to catalyze the NADPH-dependent reduction of α-ketoglutarate to R(−)-2-hydroxyglutarate (2HG). The production of 2HG is believed to contribute to the formation and progression of cancer (Dang, L et al., Nature 2009, 462:739-44).

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November 1992) to the EMBL/GenBank/DDBJ databases; and The MGC Project Team, Genome Res. 14:2121-2127(2004).

Non-mutant, e.g., wild type, IDH2 catalyzes the oxidative decarboxylation of isocitrate to α-ketoglutarate (α-KG).

It has been discovered that mutations of IDH2 present in certain cancer cells result in a new ability of the enzyme to catalyze the NADPH-dependent reduction of α-ketoglutarate to R(−)-2-hydroxyglutarate (2HG). 2HG is not formed by wild-type IDH2. The production of 2HG is believed to contribute to the formation and progression of cancer (Dang, L et al, Nature 2009, 462:739-44).

U.S. Publication No. 2015/0018328 A1 discloses a compound described by the chemical name 6-(6-chloropyridin-2-yl)-$N^2$,$N^4$-bis((R)-1,1,1-trifluoropropan-2-yl)-1,3,5-triazine-2,4-diamine, which has been shown to act as an inhibitor of mutant IDH1 and IDH2 proteins in biochemical and cellular assays.

SUMMARY

The present disclosure relates to solid forms (e.g., cocrystals and other crystalline forms) of a compound of formula (I)

(I)

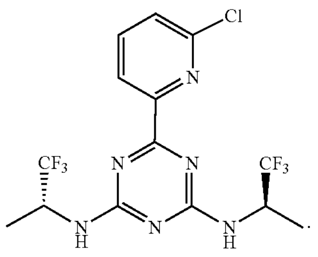

In one aspect, the disclosure relates to a cocrystal comprising the compound of formula (I) and citric acid.

In another aspect, the disclosure relates to a cocrystal comprising the compound of formula (I) and maleic acid.

In other aspects, the disclosure relates to crystalline forms of the free compound of formula (I).

In other aspects, the disclosure relates to a drug substance comprising a solid form of the compound of formula (I).

In other aspects, the disclosure relates to methods of preparing solid forms of the compound of formula (I).

In another aspect, the present application relates to a pharmaceutical composition comprising a solid form of the compound of formula (I) and one or more pharmaceutical excipients.

In another aspect, the present application relates to a method of treating a cancer characterized by the presence of an IDH1 or IDH2 mutation in a patient in need thereof, comprising administering a therapeutically effective amount of a solid form of the compound of formula (I), or a pharmaceutical composition thereof, to the patient.

BRIEF DESCRIPTION OF THE DRAWINGS

FIG. 19 depicts an Ultra-Violet (UV)/visible spectrum of the Citric Acid Cocrystal Type A of the compound of formula (I), prepared as described in Example 14.

FIG. 22 depicts a TGA thermogram of the Citric Acid Cocrystal Type A of the compound of formula (I), prepared as described in Example 14.

DETAILED DESCRIPTION

Figure 1:
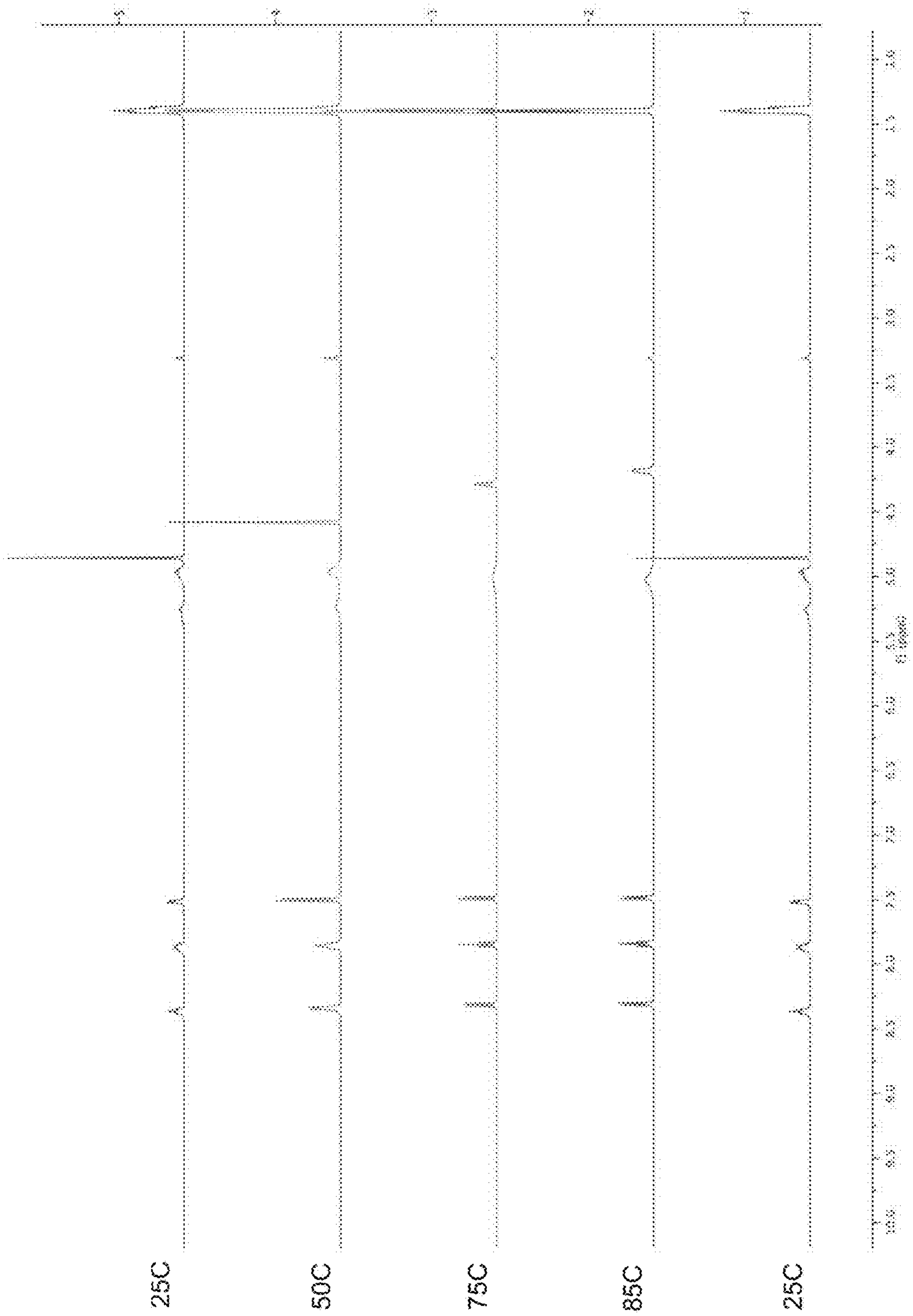
FIG. 1 depicts one-dimensional $^1H$ NMR spectra of Compound 1 in CDOD, taken over a range of temperatures from 25° C. to 85° C.

The present disclosure relates to solid forms of a compound of formula (I), as defined herein, drug substances comprising same, pharmaceutical compositions comprising same, methods of preparing same, and methods of treatment involving same.

As used herein, the compound of formula (I) includes the compound having the identified chemical structure, as well as any tautomer or rotamer thereof.

In the specification and claims, each atom of the compound of formula (I) is meant to represent any stable isotope of the specified element. In the Examples, no effort was made to enrich any atom of Compound 1 in a particular isotope, and therefore each atom likely was present at approximately the natural abundance isotopic composition of the specified element.

As used herein, the term "stable," when referring to an isotope, means that the isotope is not known to undergo spontaneous radioactive decay. Stable isotopes include, but are not limited to, the isotopes for which no decay mode is identified in V. S. Shirley & C. M. Lederer, Isotopes Project, Nuclear Science Division, Lawrence Berkeley Laboratory, Table of Nuclides (January 1980).

In some embodiments, the compound of formula (I) includes each constituent atom at approximately the natural abundance isotopic composition of the specified element.

Solid Forms

In one aspect, the disclosure relates to a cocrystal comprising a compound of formula (I)

(I)

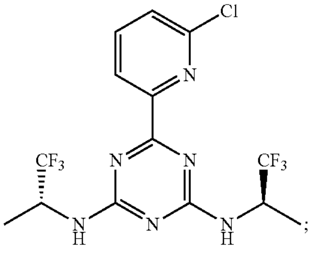

;

and citric acid (hereinafter "citric acid cocrystal").

As used herein, the term "cocrystal" refers to a crystalline solid made up of two or more neutral chemical species in a defined stoichiometric ratio that possesses distinct crystallographic and spectroscopic properties when compared to the species individually. A "cocrystal" is distinct from a "salt," which is made up of charged-balanced charged species. The species making up a cocrystal typically are linked by hydrogen bonding and other non-covalent and non-ionic interactions. Thus, a pharmaceutical cocrystal of a drug typically comprises the drug and one or more coformers. The combinations of drug and coformer(s) that will form cocrystals generally cannot be predicted ab initio, and cocrystal formation typically affects the physicochemical properties of a drug in unpredictable ways.

As used herein, the term "crystalline" refers to a solid material whose constituent particles (e.g., molecules) are arranged spatially in a regular and repeating lattice.

In another aspect, the citric acid cocrystal is citric acid cocrystal type A.

In some embodiments, citric acid cocrystal type A is characterized by an X-ray powder diffraction pattern, acquired in reflection mode (sometimes referred to as reflectance mode), comprising one or more peak positions, in degrees 2-theta (±0.2 degrees 2-theta), selected from the peak positions set forth in Tables 7 and 11 below. In other embodiments, the X-ray powder diffraction pattern comprises at least one peak position, in degrees 2-theta (±0.2 degrees 2-theta), selected from the group consisting of 5.7, 8.4, 11.4, 15.8, 18.1, 19.2, 21.1, 22.5, and 23.0. In other embodiments, the X-ray powder diffraction pattern comprises at least two peak positions, in degrees 2-theta (±0.2 degrees 2-theta), selected from the group consisting of 5.7, 8.4, 11.4, 15.8, 18.1, 19.2, 21.1, 22.5, and 23.0. In other embodiments, the X-ray powder diffraction pattern comprises at least three peak positions, in degrees 2-theta (±0.2 degrees 2-theta), selected from the group consisting of 5.7, 8.4, 11.4, 15.8, 18.1, 19.2, 21.1, 22.5, and 23.0. In other embodiments, the X-ray powder diffraction pattern comprises at least four peak positions, in degrees 2-theta (±0.2 degrees 2-theta), selected from the group consisting of 5.7, 8.4, 11.4, 15.8, 18.1, 19.2, 21.1, 22.5, and 23.0. In other embodiments, the X-ray powder diffraction pattern comprises peak positions, in degrees 2-theta (±0.2 degrees 2-theta), of 5.7 and 8.4, and at least three peak positions select from the group consisting of 11.4, 15.8, 18.1, 19.2, 21.1, 22.5, and 23.0. In other embodiments, the X-ray powder diffraction pattern comprises peak positions, in degrees 2-theta (±0.2 degrees 2-theta), of 5.7, 8.4, 11.4, 15.8, 18.1, 19.2, 21.1, 22.5, and 23.0.

In other embodiments, the X-ray powder diffraction pattern comprises the peak positions, in degrees 2-theta (±0.2 degrees 2-theta), set forth in Table 7. In other embodiments, the X-ray powder diffraction pattern comprises the peak positions, in degrees 2-theta (±0.2 degrees 2-theta), set forth in Table 11. In other embodiments, the X-ray powder diffraction pattern is similar to the X-ray powder diffraction pattern shown in FIG. 6. In other embodiments, the X-ray powder diffraction pattern is similar to the X-ray powder diffraction pattern shown in FIG. 20.

As used herein, where an X-ray powder diffraction pattern is described as having a specified number of peak positions, "in degrees 2-theta (±0.2 degrees 2-theta)," selected from a specified group of peak positions, the margin of error (±0.2 degrees 2-theta) shall be understood to apply to each peak position within the group.

As used herein, the term "similar," when referring to two or more X-ray powder diffraction patterns, means that the patterns would be understood by a person of ordinary skill in the art to represent the same crystalline form and that the patterns are the same, except for the types of variations that would be expected by a person of ordinary skill in the art to arise from experimental variations, such as instrumentation used, time of day, humidity, season, pressure, temperature, etc.

In some embodiments, citric acid cocrystal type A is characterized by a differential scanning calorimetry thermogram comprising an endothermic peak having an onset temperature of 170.6° C. (±5.0° C.). In other embodiments, citric acid cocrystal type A is characterized by a differential scanning calorimetry thermogram comprising an endothermic peak having an onset temperature of 170.6° C. (±2.0° C.).

In some embodiments, citric acid cocrystal type A further comprises water.

In some embodiments, citric acid cocrystal type A comprises the compound of formula (I), citric acid, and water in a molar ratio of 2:1:1. As a person of ordinary skill would understand, the measured molar ratio of the compound of formula (I), citric acid, and water in a given sample of the cocrystal may differ slightly from 2:1:1 due to the experimental error associated with available analytical methods, the presence of impurities (e.g., water or citric acid that is not incorporated in the crystal lattice), etc. It will be understood that cocrystals having a molar ratio of 2:1:1 fall within this embodiment, even if the measured ratio of the compound of formula (I), citric acid, and water differs slightly from 2:1:1.

In some embodiments, citric acid cocrystal type A comprises four molecules of the compound of formula (I), two citric acid molecules, and two water molecules per unit cell.

As used herein, the term “unit cell” refers to the smallest group of particles (e.g., molecules) in a crystalline solid that makes up the repeating pattern of the crystalline solid. In a cocrystal, the term “unit cell” refers to the smallest group of the two or more neutral chemical species that makes up the repeating pattern of the cocrystal.

As discussed in greater detail in the Examples, citric acid cocrystal type A was found to have a variety of favorable physicochemical properties, including high crystallinity, a sharp melting endotherm, and low hygroscopicity, and favorable bioavailability.

In another aspect, the disclosure relates to a cocrystal comprising a compound of formula (I)

(I)

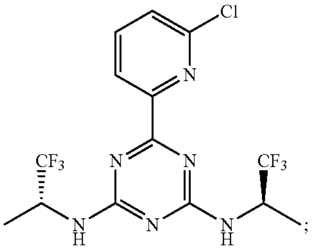

and maleic acid (hereinafter “maleic acid cocrystal”).

In another aspect, the maleic acid cocrystal is maleic acid cocrystal type A.

In some embodiments, the maleic acid cocrystal type A is characterized by an X-ray powder diffraction pattern, acquired in reflection mode (sometimes referred to as reflectance mode), comprising one or more peak positions, in degrees 2-theta (±0.2 degrees 2-theta), selected from the peak positions set forth in Table 9 below. In other embodiments, the X-ray powder diffraction pattern comprises at least one peak position, in degrees 2-theta (±0.2 degrees 2-theta), selected from the group consisting of 5.9, 8.1, 15.0, 15.2, 16.9, 17.8, 18.5, 21.1, 23.4, 26.9, and 28.2. In other embodiments, the X-ray powder diffraction pattern comprises at least two peak positions, in degrees 2-theta (±0.2 degrees 2-theta), selected from the group consisting of 5.9, 8.1, 15.0, 15.2, 16.9, 17.8, 18.5, 21.1, 23.4, 26.9, and 28.2. In other embodiments, the X-ray powder diffraction pattern comprises at least three peak positions, in degrees 2-theta (±0.2 degrees 2-theta), selected from the group consisting of 5.9, 8.1, 15.0, 15.2, 16.9, 17.8, 18.5, 21.1, 23.4, 26.9, and 28.2. In other embodiments, the X-ray powder diffraction pattern comprises at least four peak positions, in degrees 2-theta (±0.2 degrees 2-theta), selected from the group consisting of 5.9, 8.1, 15.0, 15.2, 16.9, 17.8, 18.5, 21.1, 23.4, 26.9, and 28.2. In other embodiments, the X-ray powder diffraction pattern comprises peak positions, in degrees 2-theta (±0.2 degrees 2-theta), of 8.1, 17.8, and 18.5, and at least three peak positions select from the group consisting of 5.9, 15.0, 15.2, 16.9, 21.1, 23.4, 26.9, and 28.2. In other embodiments, the X-ray powder diffraction pattern comprises peak positions, in degrees 2-theta (±0.2 degrees 2-theta), of 5.9, 8.1, 15.0, 15.2, 16.9, 17.8, 18.5, 21.1, 23.4, 26.9, and 28.2. In other embodiments, the X-ray powder diffraction pattern comprises the peak positions, in degrees 2-theta (±0.2 degrees 2-theta), set forth in Table 9. In other embodiments, the X-ray powder diffraction pattern is similar to the X-ray powder diffraction pattern shown in FIG. 12.

In some embodiments, maleic acid cocrystal type A is characterized by a differential scanning calorimetry thermogram comprising endothermic peaks having onset temperatures of 91.2° C. and 128.4° C. (±5.0° C.). In other embodiments, maleic acid cocrystal type A is characterized by a differential scanning calorimetry thermogram comprising endothermic peaks having onset temperatures of 91.2° C. and 128.4° C. (±2.0° C.).

In some embodiments, maleic acid cocrystal type A comprises the compound of formula (I) and maleic acid in a molar ratio of 1:1. As a person of ordinary skill would understand, the measured molar ratio of the compound of formula (I) and maleic acid in a given sample of the cocrystal may differ slightly from 1:1 due to the experimental error associated with available analytical methods, the presence of impurities (e.g., maleic acid that is not incorporated in the crystal lattice), etc. It will be understood that cocrystals having a molar ratio of 1:1 fall within this embodiment, even if the measured ratio of the compound of formula (I): maleic acid differs slightly from 1:1.

In another aspect, the disclosure relates to a crystalline form of a compound of formula (I)

(I)

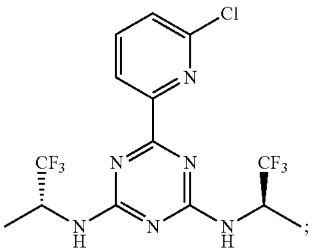

sometimes referred to as the Free Form Type A, wherein the crystalline form is characterized by an X-ray powder diffraction pattern, acquired in reflection mode (sometimes referred to as reflectance mode), comprising one or more peak positions, in degrees 2-theta (±0.2 degrees 2-theta), selected from the peak positions set forth in Table 15 below. In other embodiments, the X-ray powder diffraction pattern comprises at least one peak position, in degrees 2-theta (±0.2 degrees 2-theta), selected from the group consisting of 11.7, 12.8, 14.2, 17.8, 19.8, 20.7, 21.8, 22.2, and 25.0. In some embodiments, the X-ray powder diffraction pattern comprises at least two peak positions, in degrees 2-theta (±0.2 degrees 2-theta), selected from the group consisting of 11.7, 12.8, 14.2, 17.8, 19.8, 20.7, 21.8, 22.2, and 25.0. In other embodiments, the X-ray powder diffraction pattern comprises at least two peak positions, in degrees 2-theta (±0.2 degrees 2-theta), selected from the group consisting of 11.7, 12.8, 14.2, 17.8, 19.8, 20.7, 21.8, 22.2, and 25.0. In other embodiments, the X-ray powder diffraction pattern comprises at least three peak positions, in degrees 2-theta (±0.2 degrees 2-theta), selected from the group consisting of 11.7, 12.8, 14.2, 17.8, 19.8, 20.7, 21.8, 22.2, and 25.0. In other embodiments, the X-ray powder diffraction pattern comprises at least four peak positions, in degrees 2-theta (±0.2 degrees 2-theta), selected from the group consisting of 11.7, 12.8, 14.2, 17.8, 19.8, 20.7, 21.8, 22.2, and 25.0. In other embodiments, the X-ray powder diffraction pattern comprises peak positions, in degrees 2-theta (±0.2 degrees 2-theta), of 11.7, 17.8, and 21.8, and at least three peak positions select from the group consisting of 12.8, 14.2, 19.8, 20.7, 22.2, and 25.0. In other embodiments, the X-ray powder diffraction pattern comprises peak positions, in degrees 2-theta (±0.2 degrees 2-theta), of 11.7, 12.8, 14.2, 17.8, 19.8, 20.7, 21.8, 22.2, and 25.0. In other embodiments, the X-ray powder diffraction pattern comprises the peak positions, in degrees 2-theta (±0.2 degrees 2-theta), set forth in Table 15. In other embodiments, the X-ray powder diffraction pattern is similar to the X-ray powder diffraction pattern shown in FIG. 23.

In some embodiments, the crystalline form is characterized by a differential scanning calorimetry thermogram comprising an endothermic peak having an onset temperature of 221.9° C. (±5.0° C.). In other embodiments, the crystalline form is characterized by a differential scanning calorimetry thermogram comprising an onset temperature of 221.9° C. (±2.0° C.).

In another aspect, the disclosure relates to a crystalline form of a compound of formula (I)

(I)

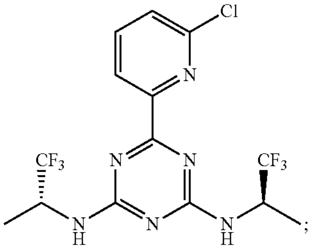

sometimes referred to as the Free Form Type B, wherein the crystalline form is characterized by an X-ray powder diffraction pattern, acquired in reflection mode (sometimes referred to as reflectance mode), comprising one or more peak positions, in degrees 2-theta (±0.2 degrees 2-theta), selected from the peak positions set forth in Table 19 below. In other embodiments, the X-ray powder diffraction pattern comprises at least one peak position, in degrees 2-theta (±0.2 degrees 2-theta), selected from the group consisting of 11.9, 13.2, 15.5, 17.8, 18.6, 20.8, 23.2, 23.9, and 26.5. In some embodiments, the X-ray powder diffraction pattern comprises at least two peak positions, in degrees 2-theta (±0.2 degrees 2-theta), selected from the group consisting of 11.9, 13.2, 15.5, 17.8, 18.6, 20.8, 23.2, 23.9, and 26.5. In other embodiments, the X-ray powder diffraction pattern comprises at least three peak positions, in degrees 2-theta (±0.2 degrees 2-theta), selected from the group consisting of 11.9, 13.2, 15.5, 17.8, 18.6, 20.8, 23.2, 23.9, and 26.5. In other embodiments, the X-ray powder diffraction pattern comprises at least four peak positions, in degrees 2-theta (±0.2 degrees 2-theta), selected from the group consisting of 11.9, 13.2, 15.5, 17.8, 18.6, 20.8, 23.2, 23.9, and 26.5. In other embodiments the X-ray powder diffraction pattern comprises peak positions, in degrees 2-theta (±0.2 degrees 2-theta), of 11.9, 17.8, and 23.9, and at least three peak positions select from the group consisting of 13.2, 15.5, 18.6, 20.8, 23.2, and 26.5. In other embodiments, the X-ray powder diffraction pattern comprises peak positions, in degrees 2-theta (±0.2 degrees 2-theta), of 11.9, 13.2, 15.5, 17.8, 18.6, 20.8, 23.2, 23.9, and 26.5. In other embodiments, the X-ray powder diffraction pattern comprises the peak positions, in degrees 2-theta (±0.2 degrees 2-theta), set forth in Table 19. In other embodiments, the X-ray powder diffraction pattern is similar to the X-ray powder diffraction pattern shown in FIG. 28.

In some embodiments, the crystalline form is characterized by a differential scanning calorimetry thermogram comprising an endothermic peak having an onset temperature of 221.5° C. (±5.0° C.). In other embodiments, the crystalline form is characterized by a differential scanning calorimetry thermogram comprising an onset temperature of 221.5° C. (±2.0° C.).

In some embodiments, the crystalline form is anhydrous.

In another aspect, the disclosure relates to a crystalline form of a compound of formula (I)

(I)

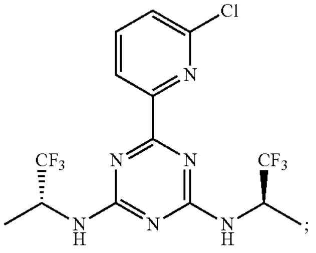

sometimes referred to as the Free Form Type C, wherein the crystalline form is characterized by an X-ray powder diffraction pattern, acquired in reflection mode (sometimes referred to as reflectance mode), comprising one or more peak positions, in degrees 2-theta (±0.2 degrees 2-theta), selected from the peak positions set forth in Table 21 below. In other embodiments, the X-ray powder diffraction pattern comprises at least one peak position, in degrees 2-theta (±0.2 degrees 2-theta), selected from the group consisting of 8.6, 10.5, 18.2, 20.2, 21.1, and 25.9. In some embodiments, the X-ray powder diffraction pattern comprises at least two peak positions, in degrees 2-theta (±0.2 degrees 2-theta), selected from the group consisting of 8.6, 10.5, 18.2, 20.2, 21.1, and 25.9. In other embodiments, the X-ray powder diffraction pattern comprises at least two peak positions, in degrees 2-theta (±0.2 degrees 2-theta), selected from the group consisting of 8.6, 10.5, 18.2, 20.2, 21.1, and 25.9. In other embodiments, the X-ray powder diffraction pattern comprises at least three peak positions, in degrees 2-theta (±0.2 degrees 2-theta), selected from the group consisting of 8.6, 10.5, 18.2, 20.2, 21.1, and 25.9. In other embodiments, the X-ray powder diffraction pattern comprises at least four peak positions, in degrees 2-theta (±0.2 degrees 2-theta), selected from the group consisting of 8.6, 10.5, 18.2, 20.2, 21.1, and 25.9. In other embodiments, the X-ray powder diffraction pattern comprises peak positions, in degrees 2-theta (±0.2 degrees 2-theta), of 8.6 and 21.1, and at least three peak positions select from the group consisting of 8.6, 10.5, 18.2, 20.2, 21.1, and 25.9. In other embodiments, the X-ray powder diffraction pattern comprises peak positions, in degrees 2-theta (±0.2 degrees 2-theta), of 8.6, 10.5, 18.2, 20.2, 21.1, and 25.9. In other embodiments, the X-ray powder diffraction pattern comprises the peak positions, in degrees 2-theta (±0.2 degrees 2-theta), set forth in Table 21. In other embodiments, the X-ray powder diffraction pattern is similar to the X-ray powder diffraction pattern shown in FIG. 32.

In some embodiments, the crystalline form is characterized by a differential scanning calorimetry thermogram comprising an endothermic peak having an onset temperature of 221.3° C. (±5.0° C.). In other embodiments, the crystalline form is characterized by a differential scanning calorimetry thermogram comprising an onset temperature of 221.3° C. (±2.0° C.).

In some embodiments, the crystalline form is a trihydrate.

In another aspect, the disclosure relates to a crystalline form of a compound of formula (I)

(I)

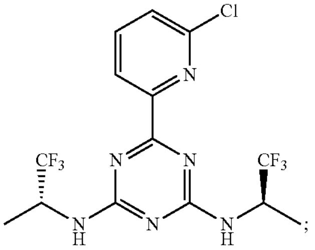

sometimes referred to as the Free Form Type D, wherein the crystalline form is characterized by an X-ray powder diffraction pattern, acquired in reflection mode (sometimes referred to as reflectance mode), comprising one or more peak positions, in degrees 2-theta (±0.2 degrees 2-theta), selected from the peak positions set forth in Table 23 below. In other embodiments, the X-ray powder diffraction pattern comprises at least one peak position, in degrees 2-theta (±0.2 degrees 2-theta), selected from the group consisting of 8.6, 9.7, 10.5, 15.6, 15.9, 16.7, 17.9, 20.3, 21.2, 24.9, 26.6, and 27.0. In some embodiments, the X-ray powder diffraction pattern comprises at least two peak positions, in degrees 2-theta (±0.2 degrees 2-theta), selected from the group consisting of 8.6, 9.7, 10.5, 15.6, 15.9, 16.7, 17.9, 20.3, 21.2, 24.9, 26.6, and 27.0. In other embodiments, the X-ray powder diffraction pattern comprises at least two peak positions, in degrees 2-theta (±0.2 degrees 2-theta), selected from the group consisting of 8.6, 9.7, 10.5, 15.6, 15.9, 16.7, 17.9, 20.3, 21.2, 24.9, 26.6, and 27.0. In other embodiments, the X-ray powder diffraction pattern comprises at least three peak positions, in degrees 2-theta (±0.2 degrees 2-theta), selected from the group consisting of 8.6, 9.7, 10.5, 15.6, 15.9, 16.7, 17.9, 20.3, 21.2, 24.9, 26.6, and 27.0. In other embodiments, the X-ray powder diffraction pattern comprises at least four peak positions, in degrees 2-theta (±0.2 degrees 2-theta), selected from the group consisting of 8.6, 9.7, 10.5, 15.6, 15.9, 16.7, 17.9, 20.3, 21.2, 24.9, 26.6, and 27.0. In other embodiments, the X-ray powder diffraction pattern comprises peak positions, in degrees 2-theta (±0.2 degrees 2-theta), of 15.9, 16.7, and 21.2, and at least three peak positions select from the group consisting of 8.6, 9.7, 10.5, 15.6, 17.9, 20.3, 24.9, 26.6, and 27.0. In other embodiments, the X-ray powder diffraction pattern comprises peak positions, in degrees 2-theta (±0.2 degrees 2-theta), of 8.6, 9.7, 10.5, 15.6, 15.9, 16.7, 17.9, 20.3, 21.2, 24.9, 26.6, and 27.0. In other embodiments, the X-ray powder diffraction pattern comprises the peak positions, in degrees 2-theta (±0.2 degrees 2-theta), set forth in Table 23. In other embodiments, the X-ray powder diffraction pattern is similar to the X-ray powder diffraction pattern shown in FIG. 36.

In some embodiments, the crystalline form is characterized by a differential scanning calorimetry thermogram comprising an endothermic peak having an onset temperature of 221.3° C. (±5.0° C.). In other embodiments, the crystalline form is characterized by a differential scanning calorimetry thermogram comprising an onset temperature of 221.3° C. (±2.0° C.).

In some embodiments, the crystalline form is a dioxane solvate.

In another aspect, the disclosure relates to an amorphous solid dispersion comprising a compound of formula (I)

(I)

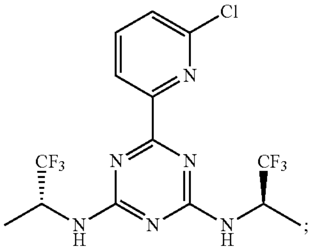

and a polymer.

As used herein, the term "dispersion" refers to a disperse system in which one substance (the dispersed phase) is distributed, in discrete units, throughout a second substance (the continuous phase or vehicle). In general, the dispersed phases can be solids, liquids, or gases. In the case of a solid dispersion, the dispersed and continuous phases are both solids.

As used herein, the term "amorphous solid dispersion" generally refers to a solid dispersion of two or more components, usually a therapeutically active compound and a polymer (or plurality of polymers), but possibly containing other components such as surfactants or other pharmaceutical excipients, where the therapeutically active compound is in the amorphous phase. In some embodiments, an amorphous solid dispersion includes the polymer(s) (and optionally a surfactant) constituting the dispersed phase, and the therapeutically active compound constitutes the continuous phase. In some embodiments, an amorphous solid dispersion includes the polymer(s) (and optionally a surfactant) constituting the continuous phase, and the therapeutically active compound constitutes the dispersed phase.

In some embodiments, the polymer is selected from the group consisting of hydroxypropyl methyl cellulose (HPMC), hydroxypropyl methylcellulose acetate succinate (HPMCAS), hydroxypropyl methyl cellulose phthalate (HPMCP), hydroxypropyl cellulose (HPC), ethylcellulose, cellulose acetate phthalate, and polyvinylpyrrolidone (PVP), or a mixture thereof. In other embodiments, the polymer is HPMCAS.

In some embodiments, the polymer is present in the amorphous solid dispersion in an amount of between about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, the polymer is (or the one or more polymers are) present in the amorphous solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, the polymer is (or the one or more polymers are) present in the amorphous solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, the compound of formula (I) is present in the amorphous solid dispersion in an amount of from about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, the compound of formula (I) is present in the amorphous solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, the compound of formula (I) is present in the amorphous solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, the amorphous solid dispersion further comprises a surfactant. In some embodiments, the surfactant is selected from the group consisting of sodium lauryl sulfate (SLS), vitamin E or a derivative thereof (e.g., vitamin E TPGS), docusate Sodium, sodium dodecyl sulfate, polysorbates (such as Tween 20 and Tween 80), poloxamers (such as Poloxamer 335 and Poloxamer 407), glyceryl monooleate, Span 65, Span 25, Capryol 90, pluronic copolymers (e.g., Pluronic F108, Pluronic P-123), and mixtures thereof. In some embodiments, the surfactant is SLS.

In some embodiments, the surfactant is present in the amorphous solid dispersion in an amount of from about 0.1% w/w to about 10% w/w, for example from about 0.5% w/w to about 2% w/w, or from about 1% w/w to about 3% w/w, from about 1% w/w to about 4% w/w, or from about 1% w/w to about 5% w/w. In some embodiments, the surfactant is present in the solid dispersion in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, or about 1% w/w. In some embodiments, the surfactant is present in the solid dispersion in an amount of about 0.5% w/w, about 1% w/w, about 1.5% w/w, about 2% w/w, about 2.5% w/w, about 3% w/w, about 3.5% w/w, about 4% w/w, about 4.5% w/w, or about 5% w/w.

In some embodiments, the amorphous solid dispersion comprises the compound of formula (I) and HPMCAS. In some embodiments, the amorphous solid dispersion consists essentially of the compound of formula (I) and HPMCAS. In some embodiments, the amorphous solid dispersion consists of the compound of formula (I) and HPMCAS. In some embodiments, the compound of formula (I) and HPMCAS are present in a weight ratio of between about 3:1 and about 1:3, or between about 2:1 and about 1:2, or between about 1.5:1 and about 1:1.5. In some embodiments, the compound of formula (I) and HPMCAS are present in a weight ratio of about 1:1.

In some embodiments, the amorphous solid dispersion has a glass transition temperature ($T_g$) of at least about 80° C. In other embodiments, the amorphous solid dispersion has a $T_g$ of between about 80° C. and about 130° C., between about 80° C. and about 120° C., between about 80° C. and about 100° C., or between about 80° C. and about 90° C.

Drug Substances

The disclosure also relates to drug substances comprising the solid forms of the compound of formula (I) described herein.

As used herein, the term "drug substance" refers to an active pharmaceutical ingredient. The term includes, but is not limited to, an active pharmaceutical ingredient that is incorporated in a pharmaceutical composition with one or more pharmaceutical excipients.

In some embodiments, the disclosure relates to drug substances having no more than specified concentrations of certain impurities, namely (R)-4-chloro-6-(6-chloropyridin-2-yl)-N-(1,1,1-trifluoropropan-2-yl)-1,3,5-triazin-2-amine (Compound 2), (R)-6-(6-chloropyridin-2-yl)-$N^2$-(1,1,1-trifluoropropan-2-yl)-1,3,5-triazine-2,4-diamine (Compound 3), (R)-4-(6-chloropyridin-2-yl)-6-((1,1,1-trifluoropropan-2-yl)amino)-1,3,5-triazin-2-ol (Compound 4), (R)-6-(6-chloropyridin-2-yl)-$N^2$-isopropyl-$N^4$-(1,1,1-trifluoropropan-2-yl)-1,3,5-triazine-2,4-diamine (Compound 5), (R)-6-(6-chloropyridin-2-yl)-$N^2$-ethyl-$N^4$-(1,1,1-trifluoropropan-2-yl)-1,3,5-triazine-2,4-diamine (Compound 6), 6-(4,6-bis(((R)-1,1,1-trifluoropropan-2-yl)amino)-1,3,5-triazin-2-yl)pyridin-2-ol (Compound 7), 6-(6-chloropyridin-2-yl)-$N^2$-((R)-1,1,1-trifluoropropan-2-yl)-$N^4$-((S)-1,1,1-trifluoropropan-2-yl)-1,3,5-triazine-2,4-diamine (Compound 8), and 6-(6-chloropyridin-2-yl)-$N^2$,$N^4$-bis((S)-1,1,1-trifluoropropan-2-yl)-1,3,5-triazine-2,4-diamine (Compound 9).

For the purposes of these embodiments, the concentration of each of Compounds 2-7 refers to the HPLC peak area % attributable to such Compound, as a percentage of the total HPLC peak area attributable to the compound of formula (I) and any organic impurities (compounds 2-9) measured by HPLC Method 1, as described in Examples 14 and 16. The concentration of each of Compounds 8 and 9 refers to the HPLC peak area % attributable to such Compound, as a percentage of the total HPLC peak area attributable to the compound of formula (I) and compounds 8 and 9 measured by HPLC Method 2, as described in Examples 14 and 16.

In one aspect, the disclosure relates to a drug substance comprising a citric acid cocrystal of the compound of formula (I), as described in any of the embodiments described herein. In some embodiments, the drug substance contains no more than 1.0% (area % by HPLC) of (R)-6-(6-chloropyridin-2-yl)-$N^2$-(1,1,1-trifluoropropan-2-yl)-1,3,5-triazine-2,4-diamine. In some embodiments, the drug substance contains no more than 1.0% (area % by HPLC) of (R)-6-(6-chloropyridin-2-yl)-$N^2$-ethyl-$N^4$-(1,1,1-trifluoropropan-2-yl)-1,3,5-triazine-2,4-diamine. In some embodiments, the drug substance contains no more than 1.0% (area % by HPLC) of (R)-6-(6-chloropyridin-2-yl)-$N^2$-isopropyl-$N^4$-(1,1,1-trifluoropropan-2-yl)-1,3,5-triazine-2,4-diamine. In some embodiments, the drug substance contains no more than 1.0% (area % by HPLC) of 6-(6-chloropyridin-2-yl)-$N^2$,$N^4$-bis((S)-1,1,1-trifluoropropan-2-yl)-1,3,5-triazine-2,4-diamine. In some embodiments, the drug substance contains no more than 1.0% (area % by HPLC) of 6-(6-chloropyridin-2-yl)-$N^2$-((R)-1,1,1-trifluoropropan-2-yl)-N4-((S)-1,1,1-trifluoropropan-2-yl)-1,3,5-triazine-2,4-diamine. In some embodiments, the drug substance contains no more than 1.0% (area % by HPLC) of (R)-4-(6-chloropyridin-2-yl)-6-((1,1,1-trifluoropropan-2-yl)amino)-1,3,5-triazin-2-ol. In some embodiments, the drug substance contains no more than 1.0% (area % by HPLC) of (R)-4-chloro-6-(6-chloropyridin-2-yl)-N-(1,1,1-trifluoropropan-2-yl)-1,3,5-triazin-2-amine. In some embodiments, the drug substance contains no more than 1.0% (area % by HPLC) of 6-(4,6-bis(((R)-1,1,1-trifluoropropan-2-yl)amino)-1,3,5-triazin-2-yl)pyridin-2-ol.

In another aspect, the disclosure relates to a drug substance comprising a Free Form Type A of the compound of formula (I), as described in any of the embodiments described herein. In some embodiments, the drug substance contains no more than 1.0% (area % by HPLC) of (R)-6-(6-chloropyridin-2-yl)-$N^2$-(1,1,1-trifluoropropan-2-yl)-1,3,5-triazine-2,4-diamine. In some embodiments, the drug substance contains no more than 1.0% (area % by HPLC) of (R)-6-(6-chloropyridin-2-yl)-$N^2$-ethyl-$N^4$-(1,1,1-trifluoropropan-2-yl)-1,3,5-triazine-2,4-diamine. In some embodiments, the drug substance contains no more than 1.0% (area % by HPLC) of (R)-6-(6-chloropyridin-2-yl)-$N^2$-isopropyl-$N^4$-(1,1,1-trifluoropropan-2-yl)-1,3,5-triazine-2,4-diamine. In some embodiments, the drug substance contains no more than 1.0% (area % by HPLC) of 6-(6-chloropyridin-2-yl)-$N^2$,$N^4$-bis((S)-1,1,1-trifluoropropan-2-yl)-1,3,5-triazine-2,4-diamine. In some embodiments, the drug substance contains no more than 1.0% (area % by HPLC) of 6-(6-chloropyridin-2-yl)-$N^2$-((R)-1,1,1-trifluoropropan-2-yl)-N4-((S)-1,1,1-trifluoropropan-2-yl)-1,3,5-triazine-2,4-diamine. In some embodiments, the drug substance contains no more than 1.0% (area % by HPLC) of (R)-4-(6-chloropyridin-2-yl)-6-((1,1,1-trifluoropropan-2-yl)amino)-1,3,5-triazin-2-ol. In some embodiments, the drug substance contains no more than 1.0% (area % by HPLC) of (R)-4-chloro-6-(6-chloropyridin-2-yl)-N-(1,1,1-trifluoropropan-2-yl)-1,3,5-triazin-2-amine. In some embodiments, the drug substance contains no more than 1.0% (area % by HPLC) of 6-(4,6-bis(((R)-1,1,1-trifluoropropan-2-yl)amino)-1,3,5-triazin-2-yl)pyridin-2-ol.

Impurities

The disclosure also relates to compounds that may be present as impurities in the solid forms described herein. Such compounds are useful as standards for determining the purity of the solid forms (e.g., cocrystals, drug substances, crystalline forms, and amorphous solid dispersions) described herein.

In one aspect, the disclosure relates to a compound selected from the group consisting of:

(R)-6-(6-chloropyridin-2-yl)-$N^2$-(1,1,1-trifluoropropan-2-yl)-1,3,5-triazine-2,4-diamine;

(R)-6-(6-chloropyridin-2-yl)-$N^2$-ethyl-$N^4$-(1,1,1-trifluoropropan-2-yl)-1,3,5-triazine-2,4-diamine;

(R)-6-(6-chloropyridin-2-yl)-$N^2$-isopropyl-$N^4$-(1,1,1-trifluoropropan-2-yl)-1,3,5-triazine-2,4-diamine;

(R)-4-(6-chloropyridin-2-yl)-6-((1,1,1-trifluoropropan-2-yl)amino)-1,3,5-triazin-2-ol;

(R)-4-chloro-6-(6-chloropyridin-2-yl)-N-(1,1,1-trifluoropropan-2-yl)-1,3,5-triazin-2-amine; and 6-(4,6-bis(((R)-1,1,1-trifluoropropan-2-yl)amino)-1,3,5-triazin-2-yl)pyridin-2-ol.

In one embodiment, compound is (R)-6-(6-chloropyridin-2-yl)-$N^2$-(1,1,1-trifluoropropan-2-yl)-1,3,5-triazine-2,4-diamine.

In one embodiment, compound is (R)-6-(6-chloropyridin-2-yl)-$N^2$-ethyl-$N^4$-(1,1,1-trifluoropropan-2-yl)-1,3,5-triazine-2,4-diamine.

In one embodiment, compound is (R)-6-(6-chloropyridin-2-yl)-$N^2$-isopropyl-$N^4$-(1,1,1-trifluoropropan-2-yl)-1,3,5-triazine-2,4-diamine.

In one embodiment, compound is (R)-4-(6-chloropyridin-2-yl)-6-((1,1,1-trifluoropropan-2-yl)amino)-1,3,5-triazin-2-ol.

In one embodiment, compound is (R)-4-chloro-6-(6-chloropyridin-2-yl)-N-(1,1,1-trifluoropropan-2-yl)-1,3,5-triazin-2-amine.

In one embodiment, compound is 6-(4,6-bis(((R)-1,1,1-trifluoropropan-2-yl)amino)-1,3,5-triazin-2-yl)pyridin-2-ol.

Tautomers

The disclosure also relates to tautomers of the chemical structure identified as the compound of formula (I). Such tautomers include:

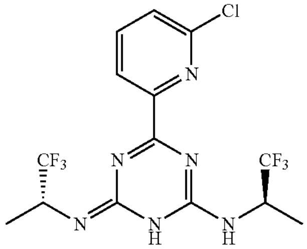 [SMILES: C[C@@H](/N=c1\nc(-c2cccc(Cl)n2)nc(N[C@H](C)C(F)(F)F)[nH]1)C(F)(F)F]

4-(6-chloropyridin-2-yl)-N—((R)-1,1,1-trifluoropropan-2-yl)-6-(((R)-1,1,1-trifluoropropan-2-yl)imino)-1,6-dihydro-1,3,5-triazin-2-amine;

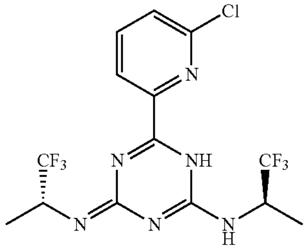 [SMILES: C[C@@H](/N=c1/nc(N[C@H](C)C(F)(F)F)[nH]c(-c2cccc(Cl)n2)n1)C(F)(F)F]

6-(6-chloropyridin-2-yl)-N—((R)-1,1,1-trifluoropropan-2-yl)-4-(((R)-1,1,1-trifluoropropan-2-yl)imino)-1,4-dihydro-1,3,5-triazin-2-amine;

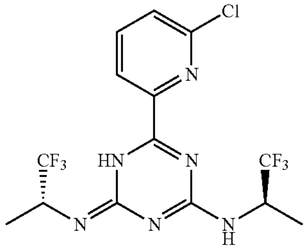 [SMILES: C[C@@H](/N=c1/nc(N[C@H](C)C(F)(F)F)nc(-c2cccc(Cl)n2)[nH]1)C(F)(F)F]

6-(6-chloropyridin-2-yl)-N—((R)-1,1,1-trifluoropropan-2-yl)-4-(((R)-1,1,1-trifluoropropan-2-yl)imino)-4,5-dihydro-1,3,5-triazin-2-amine; and

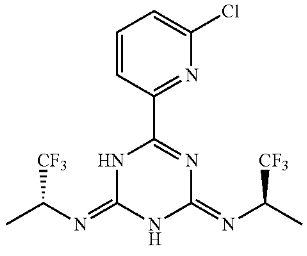 [SMILES: C[C@@H](/N=c1\nc(-c2cccc(Cl)n2)[nH]/c(=N\[C@H](C)C(F)(F)F)[nH]1)C(F)(F)F]

6-(6-chloropyridin-2-yl)-N2,N4-bis((R)-1,1,1-trifluoropropan-2-yl)-1,3,5-triazine-2,4(1H,3H)-diimine.

As used herein, the tautomers include the specified compounds, as well as any double bond isomers thereof.

In one embodiment, the disclosure relates to a compound that is:

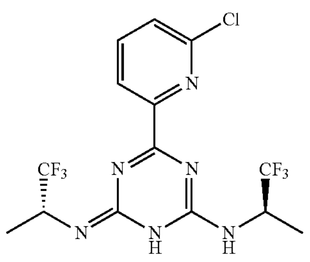 [SMILES: C[C@@H](/N=c1\nc(-c2cccc(Cl)n2)nc(N[C@H](C)C(F)(F)F)[nH]1)C(F)(F)F]

4-(6-chloropyridin-2-yl)-N—((R)-1,1,1-trifluoropropan-2-yl)-6-(((R)-1,1,1-trifluoropropan-2-yl)imino)-1,6-dihydro-1,3,5-triazin-2-amine;

or a pharmaceutically acceptable salt thereof.

In one embodiment, the disclosure relates to a compound that is:

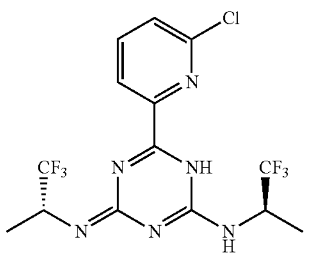 [SMILES: C[C@@H](/N=c1/nc(N[C@H](C)C(F)(F)F)[nH]c(-c2cccc(Cl)n2)n1)C(F)(F)F]

6-(6-chloropyridin-2-yl)-N—((R)-1,1,1-trifluoropropan-2-yl)-4-(((R)-1,1,1-trifluoropropan-2-yl)imino)-1,4-dihydro-1,3,5-triazin-2-amine;

or a pharmaceutically acceptable salt thereof.

In one embodiment, the disclosure relates to a compound that is:

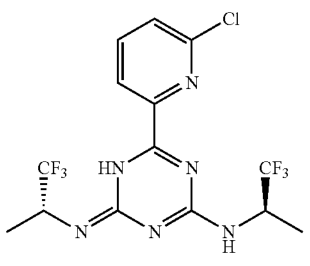 [SMILES: C[C@@H](/N=c1/nc(N[C@H](C)C(F)(F)F)nc(-c2cccc(Cl)n2)[nH]1)C(F)(F)F]

6-(6-chloropyridin-2-yl)-N—((R)-1,1,1-trifluoropropan-2-yl)-4-(((R)-1,1,1-trifluoropropan-2-yl)imino)-4,5-dihydro-1,3,5-triazin-2-amine;

or a pharmaceutically acceptable salt thereof.

In one embodiment, the disclosure relates to a compound that is:

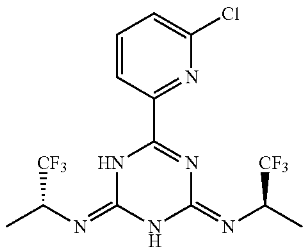 [SMILES: C[C@@H](/N=c1\nc(-c2cccc(Cl)n2)[nH]/c(=N\[C@H](C)C(F)(F)F)[nH]1)C(F)(F)F]

6-(6-chloropyridin-2-yl)-N2,N4-bis((R)-1,1,1-trifluoropropan-2-yl)-1,3,5-triazine-2,4(1H,3H)-diimine;

or a pharmaceutically acceptable salt thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" of a compound includes any non-toxic salt that, upon administration to a recipient, is capable of providing, either directly or indirectly, the compound. Pharmaceutically acceptable salts are described in detail in S. M. Berge, et al., *J. Pharmaceutical Sciences*, 1977, 66, 1-19, incorporated herein by reference.

Methods of Preparing Solid Forms of the Compound of Formula (I)

The disclosure also relates to methods of preparing solid forms of the compound of formula (I).

In one aspect, the disclosure relates to a method of preparing a citric acid cocrystal, comprising dissolving the compound of formula (I) and citric acid in a solvent to afford a solution; and precipitating the cocrystal.

In some embodiments, the cocrystal precipitated in the method is citric acid cocrystal type A (as described in any of the embodiments herein).

In some embodiments, the disclosure relates to a cocrystal prepared by any of the methods of preparing a citric acid cocrystal disclosed herein.

The citric acid employed in the method may be crystalline or amorphous and may be in any state of hydration or solvation. In some embodiments, the citric acid is anhydrous citric acid or citric acid monohydrate. In other embodiments, the citric acid is anhydrous citric acid. In other embodiments, the citric acid is citric acid monohydrate.

The solvent employed in the method may be any liquid or mixture of liquids suitable to dissolve the compound of formula (I) and citric acid. In some embodiments, the solvent comprises a polar organic solvent, such as methanol, ethyl acetate, acetonitrile, acetone, THF (e.g., THF/water (9:1 v/v)), or n-butanol (e.g., n-butanol/heptanes (1/3 v/v)). In some embodiments, the solvent comprises acetonitrile or acetone.

The compound of formula (I) and citric acid may be dissolved in the solvent in any molar ratio and in any concentration that allows for subsequent precipitation of the cocrystal from the solution. In some embodiments, the compound of formula (I) and citric acid are contacted with the solvent in a molar ratio of between about 1:2 and 4:1, or a molar ratio between about 1:1 and 3:1, or a molar ratio between about 1.5:1 and 2.5:1, or a molar ratio of about 2:1.

In some embodiments, the amount of the compound of formula (I) contacted with the solvent is sufficient to form about a 0.01 M to 3 M solution, or about a 1 M to 2 M solution, or about a 1.5 M solution, based on the amount of the compound of formula (I). As a person of ordinary skill in the art would understand, however, in the event that some of the compound of formula (I) and/or citric acid does not dissolve in the solvent, the actual molar ratio of citric acid and the compound of formula (I) in solution, and the actual concentration of the compound of formula (I) the solution, may differ from that which would be calculated from the amounts of the compound of formula (I) and citric acid contacted with the solvent.

In another aspect, the disclosure relates to a method of preparing a maleic acid cocrystal, comprising dissolving the compound of formula (I) and maleic acid in a solvent to afford a solution; and precipitating the cocrystal.

In some embodiments, the cocrystal precipitated in the method is maleic acid cocrystal type A (as described in any of the embodiments herein).

In some embodiments, the disclosure relates to a cocrystal prepared by any of the methods of preparing a maleic acid cocrystal disclosed herein.

The solvent employed in the method may be any liquid or mixture of liquids suitable to dissolve the compound of formula (I) and maleic acid. In some embodiments, the solvent comprises acetonitrile or acetone.

In another aspect, the disclosure relates to a method of preparing a crystalline form of the compound of formula (I), comprising dissolving the compound of formula (I) in ethyl acetate to afford a solution; and precipitating the crystalline form.

In some embodiments, the crystalline form precipitated in the method is the Free Form Type A (as described in any of the embodiments herein).

In some embodiments, the disclosure relates to a crystalline form prepared by any of the methods of preparing a crystalline form of the compound of formula (I) disclosed herein.

In some embodiments, precipitating the crystalline form comprises adding heptane to the solution.

In another aspect, the disclosure relates to a method of preparing a crystalline form of the compound of formula (I), comprising dissolving the compound of formula (I) in methyl isobutyl ketone to afford a solution; and precipitating the crystalline form.

In some embodiments, the crystalline form precipitated in the method is the Free Form Type B (as described in any of the embodiments herein).

In some embodiments, the disclosure relates to a crystalline form prepared by any of the methods of preparing a crystalline form of the compound of formula (I) disclosed herein.

In some embodiments, precipitating the crystalline form comprises adding heptane to the solution.

In another aspect, the disclosure relates to a method of preparing a crystalline form of the compound of formula (I), comprising dissolving the compound of formula (I) in dioxane to afford a solution; and precipitating the crystalline form.

In some embodiments, the crystalline form precipitated in the method is the Free Form Type C (as described in any of the embodiments herein).

In some embodiments, the disclosure relates to a crystalline form prepared by any of the methods of preparing a crystalline form of the compound of formula (I) disclosed herein.

In some embodiments, precipitating the crystalline form comprises adding water to the solution.

In another aspect, the disclosure relates to a method of preparing an amorphous solid dispersion of the compound of formula (I).

In some embodiments, the method comprises spray-drying a mixture comprising the compound of formula (I), a polymer, and an appropriate solvent or solvent mixture.

In some embodiments, the solvent is a volatile solvent (e.g., methylene chloride, acetone, methanol, ethanol, chloroform, tetrahydrofuran (THF), or a mixture thereof). In some embodiments, the solvent is acetone.

In some embodiments, the compound of formula (I) used in the spray-drying procedure is in the form of a cocrystal or crystalline form in accordance with any of the embodiments described herein.

Spray drying involves atomization of a liquid mixture containing, e.g., a solid and a solvent or solvent mixture, and removal of the solvent or solvent mixture. Atomization may be done, for example, through a two-fluid or pressure or electrosonic nozzle or on a rotating disk. Removal of the solvent or solvent mixture may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.). Techniques and methods for spray-drying may be found in Perry's Chemical Engineering Handbook, 6th Ed., R. H. Perry, D. W. Green & J. O. Maloney, eds., McGraw-Hill Book Co. (1984); and Marshall "Atomization and Spray-Drying" 50, Chem. Eng. Prog. Monogr. Series 2 (1954).

As used herein, the term "dissolving," when referring to dissolving one or more substances in a solvent to afford a solution, means contacting the substance(s) with an amount of solvent sufficient to dissolve at least some of each of the substance(s). The mixture comprising the substance(s) and solvent may be stirred and/or warmed to facilitate the dissolution of the substance(s) in the solvent. As a person of ordinary skill in the art would understand, some undissolved material (including some of the substance(s) and/or some other material) may remain suspended in the solution, and such suspended material may be separated from the solution (e.g., by filtration or decantation) prior to precipitation of a solid form. In some embodiments, water is added to the solution prior to precipitation of a solid form.

As used herein, the term "about," when referring to a molar ratio or concentration (e.g., molarity), means that the molar ratio or concentration has the specified value ±10%. For example, a molar ratio of "about 2:1" would include molar ratios between 1.8:1 and 2.2:1. Similarly, a concentration of "about 1.5 M" would include concentrations between 1.35 M and 1.65 M.

As used herein, the term "precipitating," when referring to precipitating a solid form from a solution, means causing the solid form to precipitate from the solution. Without intending to be bound by any theory, precipitation may be caused by saturating the solution with the solid form (e.g., by increasing the concentration of the solid form in the solution or by reducing the solubility of the solid form in the solution).

In some embodiments, "precipitating" comprises cooling the solution. Without intending to be bound by any theory, cooling the solution may cause precipitation of the solid form by decreasing the solubility of the solid form in the solution, such that the solid form reaches its saturation concentration.

In some embodiments, "precipitating" comprises evaporating a portion of the solvent from the solution. Without intending to be bound by any theory, evaporating solvent from the solution may cause precipitation of the solid form by increasing the concentration of the solid form in the solution to its saturation concentration.

In some embodiments, "precipitating" comprises adding an antisolvent to the solution. As used herein, the term "antisolvent" refers to a liquid in which the solid form is less soluble than the solvent used to form the solution. Without intending to be bound by any theory, the addition of an antisolvent to the solution may cause precipitation of the solid form by decreasing the solubility of the solid form in the solution, such that the solid form reaches its saturation concentration. In some embodiments, the antisolvent comprises a non-polar organic solvent. In some embodiments, the antisolvent comprises toluene. In some embodiments, the antisolvent comprises methyl tert-butyl ether. In some embodiments, the antisolvent comprises a $C_5$-$C_{12}$ alkane or cycloalkane.

In some embodiments, "precipitating" comprises seeding the solution with crystals of the solid form to be precipitated from solution. As used herein, the term "seeding" refers to the addition of a particular crystalline material to a solution to initiate recrystallization or crystallization of that particular crystalline material.

As used herein, the term "$C_5$-$C_{12}$ alkane or cycloalkane" means a saturated straight-chain, branched, or cyclic hydrocarbon having five to twelve carbon atoms. Examples include pentane, hexane, heptane, octane, cyclohexane, and the like.

In some embodiments, the method further comprises isolating the solid form. As used herein, the term "isolating" means separating the precipitated solid form from the solution. Such separation may be accomplished by any means known in the art, including without limitation filtration of the precipitated solid form and decantation of the solution from the precipitated solid form.

Compositions and Routes of Administration

In another aspect, the disclosure relates to a pharmaceutical composition comprising a solid form, drug substance, or compound or pharmaceutically acceptable salt, as described in any of the embodiments herein, and one or more pharmaceutical excipients.

In another aspect, the disclosure relates to a pharmaceutical composition comprising a therapeutically effective amount of a solid form, drug substance, or compound or pharmaceutically acceptable salt, as described in any of the embodiments herein, and one or more pharmaceutical excipients.

As used herein, the term "therapeutically effective amount," when referring to an amount of the solid form, drug substance, or compound or pharmaceutically acceptable salt described herein, refers to an amount that will elicit a biological or medical response in a patient, such as reducing or inhibiting an enzyme or a protein activity, alleviating or ameliorating certain symptoms, curing a disease, lessening the severity of a disease, slowing or delaying the progression of a disease, or preventing a disease. In some embodiments, the term "therapeutically effective amount" refers to the amount of solid form, drug substance, or compound or pharmaceutically acceptable salt that, when administered to a patient, is effective to inhibit mutant IDH1 and/or mutant IDH2. In other embodiments, the term "therapeutically effective amount" refers to the amount of the solid form, drug substance, or compound or pharmaceutically acceptable salt that, when administered to a patient, is effective to treat a cancer in the patient.

As used herein, the term "pharmaceutical excipient" refers to a carrier, adjuvant, or vehicle that may be administered to a patient together with the solid form, drug substance, or compound or pharmaceutically acceptable salt, that does not destroy the pharmacological activity of the compound of formula (I), and that is nontoxic when administered in doses sufficient to deliver a therapeutic amount of the compound of formula (I).

Pharmaceutical excipients that may be used in the pharmaceutical compositions described herein include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of the compound of formula (I).

In some cases, the pH of the pharmaceutical composition may be adjusted with pharmaceutically acceptable acids, bases or buffers.

The pharmaceutical compositions described herein may be administered orally, parenterally, by inhalation spray, topically, rectally, nasally, buccally, vaginally or via an implanted reservoir, preferably by oral administration or administration by injection. The pharmaceutical compositions may contain any conventional non-toxic pharmaceutically acceptable excipients.

As used herein, "parenteral" administration includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions may be orally administered in any orally acceptable dosage form including, but not limited to, capsules, tablets, emulsions and aqueous suspensions, dispersions and solutions. In the case of tablets for oral use, excipients which are commonly used include lactose, corn starch, microcrystalline cellulose, croscarmellose sodium, hydroxypropyl cellulose, colloidal silicon dioxide, and sodium lauryl sulfate. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions may also be administered in the form of suppositories for rectal administration. These compositions can be prepared by mixing the solid form, drug substance, or compound or pharmaceutically acceptable salt with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions may be administered topically to the skin. The pharmaceutical composition should be formulated with a suitable ointment containing the active components suspended or dissolved in a pharmaceutically acceptable excipient suitable for topical administration, including without limitation mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of one aspect of this invention may also be topically applied to the lower intestinal tract by rectal suppository formulation or in a suitable enema formulation. Transdermal patches are also included in one aspect of this invention.

The pharmaceutical compositions may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The amount of active ingredient that may be combined with one or more pharmaceutical excipients to produce a single dosage form will vary depending upon the patient treated and the particular mode of administration. A typical preparation will contain from about 5% to about 95% active compound (w/w). Alternatively, such preparations contain from about 20% to about 80% active compound. In some embodiments, the pharmaceutical composition comprises 1-10% w/w of the compound of formula (I) (based on the weight of the free compound of formula (I), apart from the weight of any coformer, salt former, water of hydration, solvent of solvation, and the like). In some embodiments, the pharmaceutical composition comprises 20-30% w/w of the compound of formula (I) (based on the weight of the free compound of formula (I), apart from the weight of any coformer, salt former, water of hydration, solvent of solvation, and the like). In some embodiments. The pharmaceutical composition comprises about 10 mg, about 25 mg, about 50 mg, about 100 mg, about 200 mg, or about 300 mg of the compound of formula (I) (based on the weight of the free compound of formula (I), apart from the weight of any coformer, salt former, water of hydration, solvent of solvation, and the like). In some embodiments, the pharmaceutical composition comprises about 10 mg or about 50 mg of the compound of formula (I) (based on the weight of the free compound of formula (I), apart from the weight of any coformer, salt former, water of hydration, solvent of solvation, and the like).

The pharmaceutical compositions may further comprise a therapeutically effective amount of an additional therapeutic agent, including without limitation any one of the additional therapeutic agents identified below as being useful in combination therapy.

As used herein, the term "therapeutically effective amount," when referring to an amount of an additional therapeutic agent, refers to an amount of the agent that will elicit a biological or medical response in a patient, such as reducing or inhibiting an enzyme or a protein activity, alleviating or ameliorating certain symptoms, curing a disease, lessening the severity of a disease, slowing or delaying the progression of a disease, or preventing a disease.

In another aspect, the invention relates to a pharmaceutical composition prepared by a process comprising mixing a therapeutically effective amount of a solid form, drug substance, or compound or pharmaceutically acceptable salt, as described in any of the embodiments herein, with one or more pharmaceutical excipients to afford the pharmaceutical composition.

As used here, the term "mixing" means includes any process in which the solid form, drug substance, or compound or pharmaceutically acceptable salt is contacted with one or more pharmaceutical excipients to afford a pharmaceutical composition, regardless of whether the pharmaceutical composition so obtained contains the solid form, drug substance, or compound or pharmaceutically acceptable salt. Thus, the term "mixing" includes processes in which the solid form, drug substance, or compound or pharmaceutically acceptable salt remains in the same solid form, as well as processes in which the solid form, drug substance, or compound or pharmaceutically acceptable salt is dissolved and/or converted to a different solid form. Examples of "mixing" processes including wet or dry blending, wet or dry granulation, suspension of the solid form, drug substance, or compound or pharmaceutically acceptable salt in the pharmaceutical excipient, and the like.

Uses of Solid Forms, Drug Substances, and Compounds and Salts and Pharmaceutical Compositions Thereof In another aspect, the invention relates to a method of treating a cancer characterized by the presence of an IDH1 or IDH2 mutation in a patient in need thereof, comprising administering a therapeutically effective amount of a solid form, drug substance, or compound or pharmaceutically acceptable salt, or a pharmaceutical composition thereof, as described in any of the embodiments herein, to the patient.

In another aspect, the invention relates to the use of a solid form, drug substance, or compound or pharmaceutically acceptable salt, or a pharmaceutical composition thereof, as described in any of the embodiments herein, for the manufacture of a medicament for use in treating a cancer characterized by the presence of an IDH1 or IDH2 mutation in a patient in need thereof.

In another aspect, the invention relates to a solid form, drug substance, or compound or pharmaceutically acceptable salt, or a pharmaceutical composition thereof, as described in any of the embodiments herein, for use in treating a cancer characterized by the presence of an IDH1 or IDH2 mutation in a patient in need thereof.

As used herein, the terms "treat" and "treating," when referring to a cancer, mean having a therapeutic effect on, alleviating or ameliorating one or more symptoms of, altering the progression of, eradicating, reducing the size of, slowing or inhibiting the growth or progression of, delaying or minimizing one or more symptoms associated with, reducing the malignancy of, or inducing stasis of the cancer. When referring to a disease other than a cancer, the terms "treat" and "treating" mean having a therapeutic effect on, alleviating or ameliorating one or more symptoms of, altering the progression of, eradicating, or delaying or minimizing one or more symptoms associated with the disease.

As used herein, the term "patient" refers to a mammal, including mice, rats, dogs and humans, which is afflicted with a cancer characterized by the presence of an IDH1 or IDH2 mutation. In some embodiments, the patient is a human. In some embodiments, the patient is a human adult (i.e., a human at least 18 years of age). In some embodiments, the patient is a human child (i.e., a human under 18 years of age).

In some embodiments, the cancer is characterized by the presence of an IDH1 mutation. In other embodiments, the IDH1 mutation is an R132X mutation. In other embodiments, the IDH1 mutation is an R132H or R132C mutation. In other embodiments, the IDH1 mutation is an R132H, R132C, R132L, R132V, R132S, or R132G mutation. In other embodiments, the IDH1 mutation is an R132H mutation. In other embodiments, the IDH1 mutation is an R132C mutation. In other embodiments, the IDH1 mutation results in accumulation of R(−)-2-hydroxyglutarate in the patient. In other embodiments, the IDH1 mutation results in a new ability of IDH1 to catalyze the NADPH-dependent reduction of α-ketoglutarate to R(−)-2-hydroxyglutarate. Thus, in some embodiments, treating a cancer characterized by an IDH1 mutation comprises inhibiting mutant IDH1 activity.

In some embodiments, the cancer is a tumor wherein at least 30, 40, 50, 60, 70, 80 or 90% of the tumor cells carry an IDH1 mutation, and in particular an IDH1 R132H or R132C mutation, at the time of diagnosis or treatment.

Without being bound by theory, applicants believe that mutant alleles of IDH1 wherein the IDH1 mutation results in a new ability of the enzyme to catalyze the NADPH-dependent reduction of α-ketoglutarate to R(−)-2-hydroxyglutarate, and in particular R132H and R132C mutations of IDH1, characterize a subset of all types of cancers, without regard to their cellular nature or location in the body. Thus, the compounds and methods of this invention are useful to treat any type of cancer that is characterized by the presence of a mutant allele of IDH1 imparting such activity, and in particular IDH1 R132H and R132C mutations.

As shown in Table 1, IDH1 R132X mutations are known to occur in a variety of cancers.

TABLE 1

Cancers Associated with IDH1 R132X Mutations

| Cancer Type | IDH1 R132X Mutation | Tumor Type |
|---|---|---|
| brain tumors | R132H | primary tumor |
| | R132C | primary tumor |
| | R132S | primary tumor |
| | R132G | primary tumor |
| | R132L | primary tumor |
| | R132V | primary tumor |
| fibrosarcoma | R132C | HT1080 fibrosarcoma cell line |
| Acute Myeloid Leukemia (AML) | R132H | primary tumor |
| | R132G | primary tumor |
| | R132C | primary tumor |
| Prostate cancer | R132H | primary tumor |
| | R132C | primary tumor |
| Acute lymphoblastic leukemia (ALL) | R132C | primary tumor |
| paragangliomas | R132C | primary tumor |

Accordingly, in some embodiments, the cancer is a cancer selected from the cancer types listed in Table 1, and the IDH1 mutation is one or more of the IDH1 R132X mutations listed in Table 1 for that particular cancer type.

IDH1 R132H mutations have been identified in glioma, acute myelogenous leukemia, sarcoma, melanoma, non-small cell lung cancer, cholangiocarcinomas, chondrosarcoma, myelodysplastic syndromes (MDS), myeloproliferative neoplasm (MPN), colon cancer, and angio-immunoblastic non-Hodgkin's lymphoma (NHL). Accordingly, in some embodiments, the cancer is selected from glioma, acute myelogenous leukemia, sarcoma, melanoma, non-small cell lung cancer (NSCLC), cholangiocarcinomas, chondrosarcoma, myelodysplastic syndromes (MDS), myeloproliferative neoplasm (MPN), colon cancer, or angio-immunoblastic non-Hodgkin's lymphoma (NHL). In some embodiments, the cancer is glioma, and the glioma is a low grade glioma or a secondary high grade glioma. In other embodiments, the cancer is glioma, and the glioma is a low grade glioma (grade II), anaplastic (grade III) or glioblastoma (GBM, grade IV).

In some embodiments, the cancer is characterized by the presence of an IDH2 mutation. In other embodiments, the IDH2 mutation is an R140X mutation. In other embodiments, the IDH2 mutation is an R1400, R140W, or R140L mutation. In other embodiments, the IDH2 mutation is an R172X mutation. In other embodiments, the IDH2 mutation is an R172K or R172G mutation. In other embodiments, the IDH2 mutation is an R140X mutation. In other embodiments, the IDH2 mutation is an R1400 mutation. In other embodiments, the IDH2 mutation is an R140W mutation. In other embodiments, the IDH2 mutation is an R140L mutation. In other embodiments, the IDH2 mutation is an R172X mutation. In other embodiments, the IDH2 mutation is an R172K mutation. In other embodiments, the IDH2 mutation is an R172G mutation. In other embodiments, the IDH2 mutation results in accumulation of R(−)-2-hydroxyglutarate in the patient. In other embodiments, the IDH2 mutation results in a new ability of IDH2 to catalyze the NADPH-dependent reduction of α-ketoglutarate to R(−)-2-hydroxyglutarate. Thus, in some embodiments, treating a cancer characterized by an IDH2 mutation comprises inhibiting mutant IDH2 activity.

Without being bound by theory, applicants believe that mutant alleles of IDH2 wherein the IDH2 mutation results in a new ability of the enzyme to catalyze the NADPH-dependent reduction of α-ketoglutarate to R(−)-2-hydroxyglutarate, and in particular R1400 and/or R172K mutations of IDH2, characterize a subset of all types of cancers, without regard to their cellular nature or location in the body. Thus, the compounds and methods of one aspect of this invention are useful to treat any type of cancer that is characterized by the presence of a mutant allele of IDH2 imparting such activity and in particular an IDH2 R1400 and/or R172K mutation.

In some embodiments, the cancer is a tumor wherein at least 30, 40, 50, 60, 70, 80 or 90% of the tumor cells carry an IDH2 mutation, and in particular an IDH2 R1400, R140W, or R140L and/or R172K or R172G mutation, at the time of diagnosis or treatment.

A cancer can be analyzed by sequencing cell samples to determine the presence and specific nature of any mutation (s) characterizing the cancer.

In some embodiments, the cancer is glioma, acute myelogenous leukemia, sarcoma, melanoma, non-small cell lung cancer (NSCLC), cholangiocarcinomas (e.g., intrahepatic cholangiocarcinoma (IHCC)), chondrosarcoma, myelodysplastic syndromes (MDS), myeloproliferative neoplasm (MPN), prostate cancer, chronic myelomonocytic leukemia (CMML), B-acute lymphoblastic leukemias (B-ALL), B-acute lymphoblastic leukemias (B-ALL), myeloid sarcoma, multiple myeloma, lymphoma colon cancer, or angio-immunoblastic non-Hodgkin's lymphoma (NHL). In some embodiments, the cancer is glioma, and the glioma is a low grade glioma or a secondary high grade glioma. In other embodiments, the cancer is glioma, the glioma is a low grade glioma (grade II), anaplastic (grade Ill) or glioblastoma (GBM, grade IV).

In some embodiments, the cancer is lymphoma (e.g., Non-Hodgkin lymphoma (NHL) such B-cell lymphoma (e.g., Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell lymphoma (e.g., mycosis fungoides, anaplastic large cell lymphoma, or precursor T-lymphoblastic lymphoma)).

In some embodiments, the cancer is glioma, myelodysplastic syndrome (MDS), myeloproliferative neoplasm (MPN), acute myelogenous leukemia (AML), sarcoma, melanoma, non-small cell lung cancer, chondrosarcoma, cholangiocarcinomas or angio-immunoblastic lymphoma. In other embodiments, the cancer is glioma, myelodysplastic syndrome (MDS), myeloproliferative neoplasm (MPN), acute myelogenous leukemia (AML), melanoma, chondrosarcoma, or angioimmunoblastic non-Hodgkin's lymphoma (NHL). In some embodiments, the cancer is glioma, and the glioma is a low grade glioma or a secondary high grade glioma. In other embodiments, the cancer is glioma, and the glioma is a low grade glioma (grade II), anaplastic (grade III) or glioblastoma (GBM, grade IV).

In some embodiments the cancer is refractory or relapsed. In other embodiments the cancer is newly diagnosed or previously untreated.

In one aspect of this embodiment, the efficacy of cancer treatment is monitored by measuring the levels of 2HG as described herein.

In some embodiments, the efficacy of cancer treatment is monitored by measuring the levels of 2HG in the patient. Typically levels of 2HG are measured prior to treatment, wherein an elevated level is indicated for the use of the compound of formula (I), including in the form of the solid form, drug substance, or compound or pharmaceutically acceptable salt or pharmaceutical composition thereof, as described in any of the embodiments herein, to treat the cancer. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, 2HG measurements will be utilized together with other well-known determinations of efficacy of cancer treatment, such as reduction in number and size of tumors and/or other cancer-associated lesions, improvement in the general health of the patient, and alterations in other biomarkers that are associated with cancer treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomonex) can be used as the column, as described above. Metabolites can be quantified by comparison of peak areas with pure metabolite standards at known concentration. Metabolite flux studies from $^{13}C$-glutamine can be performed as described, e.g., in Munger et al. Nat Biotechnol 26, 1179-86, 2008.

In some embodiments, 2HG is directly evaluated.

In other embodiments, a derivative of 2HG formed in the process of performing the analytic method is evaluated. By way of example, such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

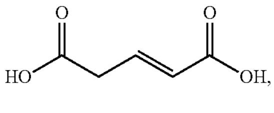, 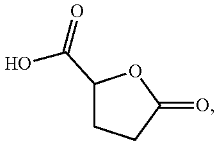, 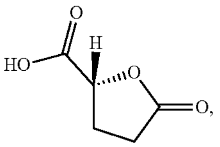, and 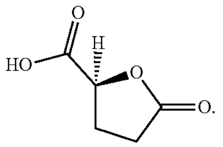.

In some embodiments, various evaluation steps are performed prior to and/or following treatment of a cancer with the solid form, drug substance, or compound or pharmaceutically acceptable salt or pharmaceutical composition thereof. Thus, in some embodiments, the method described herein further comprises an evaluation step prior to and/or after treatment with the solid form, drug substance, or compound or pharmaceutically acceptable salt or pharmaceutical composition thereof.

In some embodiments, the evaluation steps comprise evaluating the growth, size, weight, invasiveness, stage and/or other phenotype of the cancer. Thus, in some embodiments, the method described herein further comprises the step of evaluating the growth, size, weight, invasiveness, stage and/or other phenotype of the cancer prior to and/or after treatment with the solid form, drug substance, or compound or pharmaceutically acceptable salt or pharmaceutical composition thereof.

In some embodiments, prior to and/or after treatment with the solid form, drug substance, or compound or pharmaceutically acceptable salt or pharmaceutical composition thereof, the method further comprises the step of evaluating the IDH1 genotype of the cancer. This may be achieved by ordinary methods in the art, such as DNA sequencing, immuno analysis, and/or evaluation of the presence, distribution or level of 2HG.

In some embodiments, prior to and/or after treatment with the solid form, drug substance, or compound or pharmaceutically acceptable salt or pharmaceutical composition thereof, the method further comprises the step of determining the 2HG level in the patient. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. Am J Hum Genet 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, J Neurooncol 91, 233-6 (2009); Kolker, S., Mayatepek, E. & Hoffmann, G. F. Neuropediatrics 33, 225-31 (2002); Wajner, M., Latini, A., Wyse, A. T. & Dutra-Filho, C. S. J Inherit Metab Dis 27, 427-48 (2004)). Furthermore, elevated brain levels of 2HG result in increased ROS levels (Kolker, S. et al. Eur J Neurosci 16, 21-8 (2002); Latini, A. et al. Eur J Neurosci 17, 2017-22 (2003)), potentially contributing to an increased risk of cancer. The ability of 2HG to act as an NMDA receptor agonist may contribute to this effect (Kolker, S. et al. Eur J Neurosci 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate HIF1-alpha levels.

Thus, according to another embodiment, one aspect of the invention provides a method of treating 2-hydroxyglutaric aciduria, particularly D-2-hydroxyglutaric aciduria, in a patient by administering to the patient a therapeutically effective amount of the solid form, drug substance, or compound or pharmaceutically acceptable salt, or a pharmaceutical composition thereof, as described in any one of the embodiments herein.

Also provided are methods of treating a disease selected from Maffucci syndrome and Ollier disease, characterized by the presence of a mutant allele of IDH1 comprising the step of administering to patient in need thereof a therapeutically effective amount of the solid form, drug substance, or compound or pharmaceutically acceptable salt, or a pharmaceutical composition thereof, as described in any one of the embodiments herein.

Treatment methods described herein can additionally comprise various evaluation steps prior to and/or following treatment with the solid form, drug substance, or compound or pharmaceutically acceptable salt or pharmaceutical composition thereof.

In one embodiment, prior to and/or after treatment with the solid form, drug substance, or compound or pharmaceutically acceptable salt or pharmaceutical composition thereof, the method further comprises the step of evaluating the growth, size, weight, invasiveness, stage and/or other phenotype of the cancer.

In one embodiment, prior to and/or after treatment with the solid form, drug substance, or compound or pharmaceutically acceptable salt or pharmaceutical composition thereof, the method further comprises the step of evaluating the IDH2 genotype of the cancer. This may be achieved by ordinary methods in the art, such as DNA sequencing, immuno analysis, and/or evaluation of the presence, distribution or level of 2HG.

The solid form, drug substance, or compound or pharmaceutically acceptable salt, and pharmaceutical compositions thereof, as described in any of the embodiments herein, can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between about 1 mg and about 1000 mg/dose, every 4 to 120 hours, based on the amount of the compound of formula (I). In some embodiments, the solid form, drug substance, or compound or pharmaceutically acceptable salt or pharmaceutical composition thereof is administered once, twice, or three times a day. In other embodiments, the solid form, drug substance, or compound or pharmaceutically acceptable salt or pharmaceutical composition thereof is administered once a day. In other embodiments, the solid form, drug substance, or compound or pharmaceutically acceptable salt, or pharmaceutical composition thereof is administered twice a day. In other embodiments, the solid form, drug substance, or compound or pharmaceutically acceptable salt, or pharmaceutical composition thereof is administered three times a day. The methods herein contemplate administration of a therapeutically effective amount of the solid form, drug substance, or compound or pharmaceutically acceptable salt, or pharmaceutical composition thereof so as to achieve the desired or stated effect. Typically, the pharmaceutical compositions of one aspect of this invention will be administered from about 1 to about 6 times per day or alternatively, as a continuous infusion. In some embodiments, the solid form, drug substance, or compound or pharmaceutically acceptable salt, or pharmaceutical composition thereof is administered once a day. In other embodiments, the solid form, drug substance, or compound or pharmaceutically acceptable salt, or pharmaceutical composition thereof is administered twice a day. Such administration can be used as a chronic or acute therapy.

In some embodiments, the solid form, drug substance, or compound or pharmaceutically acceptable salt, or pharmaceutical composition thereof, as described in any of the embodiments herein, is administered in a dosage, based on the amount of the compound of formula (I), of: (1) from 1 to 100 mg/day, 2 to 50 mg/day, 3 to 30 mg/day, 4 to 20 mg/day, 5 to 15 mg/day, 8 to 12 mg/day, or about 10 mg/day; (2) from 1 to 500 mg/day, 1 to 250 mg/day, 5 to 100 mg/day, 8 to 75 mg/day, 10 to 50 mg/day, 15 to 40 mg/day, 20 to 30 mg/day, or about 25 mg/day; (3) from 1 to 500 mg/day, 10 to 250 mg/day, 20 to 100 mg/day, 30 to 80 mg/day, 40 to 60 mg/day, 45 to 55 mg/day, or about 50 mg/day; (4) from 1 to 500 mg/day, 20 to 400 mg/day, 40 to 200 mg/day, 50 to 150 mg/day, 75 to 125 mg/day, 85 to 115 mg/day, 90 to 110 mg/day, or about 100 mg/day; (5) from 1 to 500 mg/day, 50 to 400 mg/day, 100 to 300 mg/day, 150 to 250 mg/day, 175 to 225 mg/day, 185 to 215 mg/day, 190 to 210 mg/day, or about 200 mg/day; or (6) from 1 to 500 mg/day, 100 to 500 mg/day, 200 to 400 mg/day, 250 to 350 mg/day, 275 to 375 mg/day, 285 to 315 mg/day, 290 to 310 mg/day, or about 300 mg/day.

In some embodiments, the solid form, drug substance, or compound or pharmaceutically acceptable salt, or pharmaceutical composition thereof, as described in any of the embodiments herein, is administered in a dosage, based on the amount of the compound of formula (I), of from 0.01 to 10 mg/kg of body weight per day, 0.2 to 8.0 mg/kg of body weight per day, 0.4 to 6.0 mg/kg of body weight per day, 0.6 to 4.0 mg/kg of body weight per day, 0.8 to 2.0 mg/kg of body weight per day, 0.1 to 1 mg/kg of body weight per day, 0.2 to 1.0 mg/kg of body weight per day, 0.15 to 1.5 mg/kg of body weight per day, or 0.1 to 0.5 mg/kg of body weight per day.

In some embodiments, the solid form, drug substance, or compound or pharmaceutically acceptable salt, or pharmaceutical composition thereof, as described in any of the embodiments herein, is administered once per day or more than once per day (e.g., twice per day, three times per day, four times per day, etc.) to achieve administration of the daily dosages described herein. In some embodiments, the solid form, drug substance, or compound or pharmaceutically acceptable salt, or pharmaceutical composition thereof, as described in any of the embodiments herein, is administered once per day to achieve administration of the daily dosages described herein. In some embodiments, the solid form, drug substance, or compound or pharmaceutically acceptable salt, or pharmaceutical composition thereof, as described in any of the embodiments herein, is administered twice per day to achieve administration of the daily dosages described herein. In some embodiments, the solid form, drug substance, or compound or pharmaceutically acceptable salt, or pharmaceutical composition thereof, as described in any of the embodiments herein, is administered once per day in a dosage, based on the amount of the compound of formula (I), of: (1) about 10 mg, about 25 mg, about 50 mg, about 100 mg, about 200 mg, or about 300 mg per administration; (2) 30-70 mg, 35-65 mg, 40-60 mg, 45-55 mg, or about 50 mg per administration; or (3) 5-35 mg, 5-20 mg, 5-15 mg, or about 10 mg per administration. In some embodiments, the solid form, drug substance, or compound or pharmaceutically acceptable salt, or pharmaceutical composition thereof, as described in any of the embodiments herein, is administered twice per day in a dosage, based on the amount of the compound of formula (I), of: (1) 30-70 mg, 35-65 mg, 40-60 mg, 45-55 mg, or about 50 mg per administration; or (2) 5-35 mg, 5-20 mg, 5-15 mg, or about 10 mg per administration. The amounts of the solid form, drug substance, or compound or pharmaceutically acceptable salt, or pharmaceutical composition thereof, set forth herein are based on the amount of the compound of formula (I). Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

As used herein, the term "about," when referring to a dosage, means that the dosage has the specified value ±10%. For example, a dosage of "about 100 mg/kg" would include dosages between 90 mg/kg and 110 mg/kg.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of the compound of formula (I), administered as the solid form, drug substance, or compound or pharmaceutically acceptable salt, or a pharmaceutical composition thereof, as described in any of the embodiments herein, or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Previously Treated Patients

In some embodiments, the patient in need of treatment for a cancer characterized by the presence of an IDH1 or IDH2 mutation was previously administered a cancer therapy. In some embodiments, the patient was previously administered a cancer therapy for the cancer. The previously administered cancer therapy may have been effective or ineffective in treating the cancer, or may have been effective for some period of time in treating the cancer.

As used herein, the term "cancer therapy" refers to a cancer therapeutic agent or a cancer treatment. As used herein, the term "cancer therapeutic agent" refers to a therapeutic agent (other than the compound of formula (I), the solid form, drug substance, or compound or pharmaceutically acceptable salt, or the pharmaceutical composition thereof) that is indicated for treating a cancer. Cancer therapeutic agents include, for example, chemotherapy, targeted therapy agents, antibody therapies, immunotherapy agents, hormonal therapy agents, and check point inhibitors. Examples of each of these classes of cancer therapeutic agents are provided below. As used herein, the term “cancer treatment” refers to a treatment that is indicated for treating a cancer. Cancer treatments include, for example, surgery and radiation therapy.

In some embodiments, the cancer therapeutic agent is a chemotherapy agent. Examples of chemotherapy agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others), and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifamib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy.

In some embodiments, the cancer therapeutic agent is a differentiation agent. Differentiation agents include retinoids (such as all-trans-retinoic acid (ATRA), 9-cis retinoic acid, 13-cis-retinoic acid (13-cRA) and 4-hydroxy-phenretinamide (4-HPR)); arsenic trioxide; histone deacetylase inhibitors HDACs (such as azacytidine (Vidaza) and butyrates (e.g., sodium phenylbutyrate)); hybrid polar compounds (such as hexamethylene bisacetamide ((HMBA)); vitamin D; and cytokines (such as colony-stimulating factors including G-CSF and GM-CSF, and interferons).

In some embodiments, the cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib.

Other targeted therapy agents include biguanides such as metformin or phenformin.

Targeted therapy can also involve small peptides as “homing devices” which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, the cancer therapeutic agent is an antibody. Monoclonal antibody therapy is a strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox.

In some embodiments, the cancer therapeutic agent is an immunotherapy agent. Cancer immunotherapy refers to a diverse set of therapeutic strategies designed to induce the patient’s own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor’s immune cells will often attack the tumor in a graft-versus-tumor effect.

In some embodiments, the cancer therapeutic agent is a hormonal therapy agent. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial.

In some embodiments, the cancer therapeutic agent is a check point inhibitor. Check point inhibitor therapy is a form of cancer treatment in which manipulation of immune system checkpoints is used restore immune system function against cancer cells. Examples of check point inhibitors include ipilimumab, nivolumab, pembrolizumab, atezolizumab, avelumab, durvalumab, and the like.

Other cancer therapeutic agents include imatinib, gene therapy, peptide and dendritic cell vaccines, synthetic chlorotoxins, radiolabeled drugs and antibodies, Chimeric antigen receptors or CAR-Ts (e.g., Kymriah® (tisagenlecleucel), Yescarta® (axicabtagene ciloleucel)), Gliadel® (carmustine implant), and Avastin® (bevacizumab).

In some embodiments, the cancer treatment is radiation therapy. Radiation therapy involves the use of high-energy radiation (e.g., x-rays, gamma rays, or charged particles) to damage and/or kill cancer cells and to shrink tumors. In the methods of the invention, radiation may be delivered to the brain tumor (e.g., glioma) by a machine positioned outside the body (external-beam radiation therapy), by radioactive material placed in the body near the brain tumor (internal radiation therapy, also called brachytherapy), or by radioactive substances administered systemically (e.g., radioactive iodine) that travel through the bloodstream to the brain tumor. Alternatively, these delivery methods can be used in combination.

In some embodiments, the radiation therapy comprises external radiation therapy (e.g., external-beam radiation therapy including fractionated external-beam radiation therapy, stereotactic radiation such as Cyberknife® or Gamma Knife®, proton therapy, and the like), where the radiation is delivered to the brain tumor (e.g., glioma) by an instrument outside the body. External radiation therapy may be given as a course of several treatments over days or weeks. In one aspect of these embodiments, the radiation is administered in the form of x-rays.

In other embodiments, the radiation therapy comprises internal radiation therapy, where the radiation comes from an implant or a material (liquid, solid, semi-solid or other substance) placed inside the body. In one aspect of these embodiments, the internal radiation therapy is brachytherapy, where a solid radioactive source is placed inside the body near the brain tumor. In another aspect of these embodiments, the internal radiation therapy comprises the systemic administration of a radiation source, typically a radionuclide (radioisotope or unsealed source). The radiation source may be orally administered or may be injected into a vein.

Combination Therapies

In some embodiments, the methods described herein comprise the additional step of co-administering to a patient in need thereof an additional therapy.

In some embodiments, the medicament for use in treating a cancer characterized by the presence of an IDH1 or IDH2 mutation in a patient in need thereof is for use in combination with the co-administration of an additional therapy.

In another aspect, the solid form, drug substance, or compound or pharmaceutically acceptable salt, or pharmaceutical composition thereof for use in treating a cancer characterized by the presence of an IDH1 or IDH2 mutation is for use in combination with the co-administration of an additional therapy.

As used herein, the term "additional therapy" includes cancer therapies (including cancer therapeutic agents and cancer treatments), as described above, as well as non-cancer therapies (including non-cancer therapeutic agents and non-cancer treatments) administered to treat symptoms and/or secondary effects of the cancer. In other words, the term "additional therapy" includes additional therapeutic agents (i.e., cancer therapeutic agents and non-cancer therapeutic agents) and additional treatments (i.e., cancer treatments and non-cancer treatments).

In some embodiments, the additional therapy is a cancer therapy (i.e., a cancer therapeutic agent or cancer treatment), as described above.

In some embodiments, the additional therapy is a non-cancer therapy (i.e., a non-cancer therapeutic agent or non-cancer treatment).

In some embodiments, the additional therapy comprises one or more of a DNA-reactive agent, a PARP inhibitor, an anti-emesis agent, an anti-convulsant or anti-epileptic agent, a checkpoint inhibitor, PVC chemotherapy, bevacizumab, and gemcitabine.

In some embodiments, the additional therapy comprises a DNA-reactive agent. As used herein, "DNA-reactive agents" are those agents, such as alkylating agents, cross-linking agents, and DNA intercalating agents, which interact covalently or non-covalently with cellular DNA. For example, DNA-reactive agents include adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, mitozolomide, nedaplatin, oxaliplatin, piposulfan, procarbazine, semustine, streptozocin, temozolomide, thiotepa, treosulfan, diethylnitrosoamine, benzo(a)pyrene, doxorubicin, mitomycin-C, and the like. Many of these DNA-reactive agents are useful in cancer therapy as DNA-reactive chemotherapeutic agents.

In some embodiments, the additional therapy comprises a PARP inhibitor. As used herein, "PARP inhibitor" refers to an inhibitor of the enzyme poly ADP ribose polymerase (PARP). Examples of PARP inhibitors include pamiparib, olaparib, rucaparib, velaparib, iniparib, talazoparib, niraparib, and the like.

In some embodiments, the additional therapy is a checkpoint inhibitor. As used herein, "checkpoint inhibitor" refers to a therapeutic agent that inhibits an immune checkpoint (e.g., CTLA-4, PD-1/PD-L1, and the like) that otherwise would prevent immune system attacks on cancer cells, thereby allowing the immune system to attack the cancer cells. Examples of check point inhibitors include ipilimumab, nivolumab, pembrolizumab, atezolizumab, avelumab, durvalumab, BGB-A317, spartalizumab, and the like.

In some embodiments, the additional therapy is PVC chemotherapy. As used herein, "PVC chemotherapy" refers to a chemotherapy regimen comprising the combined administration of procarbazine, lomustine (which is sold under the trade name CCNU®), and vincristine (which is sold under the trade name Onocovin®). Typically, the vincristine is administered intravenously, while the procarbazine, and lomustine are administered orally. PCV chemotherapy often is administered in cycles, wherein each cycle comprises a single administration of vincristine and lomustine and a 10-day course of treatment with procarbazine.

In some embodiments, the additional therapy is bevacizumab. Bevacizumab, which is sold under the trade name Avastin®, is a recombinant humanized monoclonal antibody.

In some embodiments, the additional therapy is gemcitabine. Gemcitabine, which is sold under the trade name Gemzar®, is a pyrimidine nucleoside analog.

In some embodiments, the additional therapy is a non-cancer therapeutic agent. As used herein, the term "non-cancer therapeutic agent" refers to a therapeutic agent that is used to treat symptoms suffered by patients afflicted with a cancer, and/or undergoing treatment for a cancer, but that is not indicated for treating the cancer itself. Examples of "non-cancer therapeutic agents" include anti-seizure and anti-epileptic agents, anti-emesis agents, anti-diarrheal agents, and the like.

In some embodiments, the additional therapy is an anti-seizure or anti-epileptic agent. As used herein, "anti-seizure or anti-epileptic agent" refers to a drug that is effective for treating or preventing seizures, including epileptic seizures. Examples of anti-seizure and anti-epileptic agents include acetazolamide, barbexaclone, beclamide, brivaracetam, cannabidiol, carbamazepine, clobazam, clonazepam, clorazepate, diazepam, divalproex sodium, eslicarbazepine acetate, ethadione, ethosuximide, ethotoin, etiracetam, felbamate, fosphenytoin, gabapentin, lacosamide, lamotrigine, levetiracetam, lorazepam, mephenytoin, mesuximide, methazolamide, methylphenobarbital, midazolam, nimetazepam, nitrazepam, oxcarbazepine, paraldehyde, paramethadoine, perampanel, piracetam, phenacemide, pheneturide, phenobarbital, phensuximide, phenytoin, potassium bromide, pregabalin, primidone, progabide, pyridoxine, rufinamide, seletracetam, sodium valproate, stiripentol, sultiame, temazepam, tiagabine, topiramate, trimethadione, valnoctamide, valproic acid, valpromide, vigabatrin, zonisamide, and the like.

In some embodiments, the additional therapy is an anti-emesis agent. As used herein, "anti-emesis agent" refers to a drug that is effective to reduce vomiting and nausea symptoms. Examples of anti-emesis agents include 5-$HT_3$ receptor antagonists (e.g., dolasetron, granisetron, ondansetron, tropisetron, palonosetron, mirtazapine, and the like), dopamine agonists (e.g., domperidone, olanzapine, droperidol, haloperidol, chlorpromazine, prochlorperazine, alizapride, prochlorperazine, metoclopramide, and the like), NK1 receptor antagonists (e.g., aprepitant, casopitant, rolapitant, and the like), antihistamines (e.g., cinnarizine, cyclizine, diphenhydramine, dimenhydrinate, doxylamine, meclizine, promethazine, hydroxyzine, and the like), cannabinoids (e.g, cannabis, dronabinol, synthetic cannabinoids, and the like), benzodiazepines (e.g., midazolam, lorazepam, and the like), anticholinergics (e.g., scopolamine and the like), steroids (e.g., dexamethasone and the like), trimethobenzamide, ginger, propofol, glucose/fructose/phosphoric acid (which is sold under the trade name Emetrol®), peppermint, muscimol, ajwain, bismuth-subsalicylate, and the like.

In some embodiments, the additional therapy is an anti-diarrheal agent.

Examples of anti-diarrheal agents include bismuth subgallate, *Saccharomyces boulardii* lyo, atropine, diphenoxylate, difenoxin, *Lactobacillus acidophilus*, bismuth subsalicylate, loperamide, *Lactobacillus bulgaricus*, *Lactobacillus rhamnosus* gg, attapulgite, crofelemer, simethicone, and the like.

In some embodiments, the additional therapy is a non-cancer treatment. As used herein, the term "non-cancer treatment" refers to a treatment that is used to treat symptoms suffered by patients afflicted with a cancer, and/or undergoing treatment for a cancer, but that is not indicated for treating the cancer itself. Examples of non-cancer treatments include acupuncture, biofeedback, distraction, emotional support and counseling, hypnosis, imagery, relaxation, skin stimulation, and the like.

The term "co-administering" as used herein, means that the additional therapy is administered prior to, concurrently with, consecutively with, or following the administration of the solid form, drug substance, or compound or pharmaceutically acceptable salt, or pharmaceutical composition thereof as part of a treatment regimen to provide a beneficial effect from the combined action of the solid form, drug substance, or compound or pharmaceutically acceptable salt (or pharmaceutical composition thereof) and the additional therapy. Where the additional therapy is an additional therapeutic agent, the additional therapeutic agent may be administered together with the solid form, drug substance, or compound or pharmaceutically acceptable salt as part of a single dosage form (such as a composition of one aspect of this invention comprising a cocrystal, drug substance, crystalline form, or amorphous solid dispersion and the therapeutic agent) or as separate, multiple dosage forms. Alternatively, the therapeutic agent may be administered prior to, consecutively with, or following the administration of the solid form, drug substance, or compound or pharmaceutically acceptable salt. In such combination therapy treatment, both the solid form, drug substance, or compound or pharmaceutically acceptable salt and the additional therapeutic agent(s) are administered by conventional methods. The administration of a composition of one aspect of this invention, comprising both a solid form, drug substance, or compound or pharmaceutically acceptable salt and an additional therapeutic agent, to a patient does not preclude the separate administration of that same therapeutic agent, any other additional therapeutic agent or the solid form, drug substance, or compound or pharmaceutically acceptable salt to said patient at another time during a course of treatment. Where the additional therapy is an additional treatment, the additional treatment may be administered prior to, consecutively with, concurrently with or following the administration of the solid form, drug substance, or compound or pharmaceutically acceptable salt or pharmaceutical composition thereof.

In some embodiments, when the additional therapy is a cancer therapy, both the solid form, drug substance, or compound or pharmaceutically acceptable salt and the cancer therapy are administered at dosage levels of between about 1 to 100%, or between about 5 to 95%, of the dosage normally administered in a monotherapy regimen.

Enumerated Embodiments

In some embodiments, the disclosure relates to:

1. A cocrystal comprising a compound of formula (I)

(I)

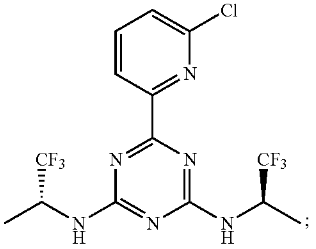

and citric acid.

2. The cocrystal of embodiment 1, wherein the cocrystal is characterized by an X-ray powder diffraction pattern, acquired in reflection mode, comprising at least one peak position, in degrees 2-theta (±0.2 degrees 2-theta), selected from the group consisting of 5.7, 8.4, 11.4, 15.8, 18.1, 19.2, 21.1, 22.5, and 23.0.

3. The cocrystal of embodiment 1 or 2, wherein the X-ray powder diffraction pattern comprises at least two peak positions, in degrees 2-theta (±0.2 degrees 2-theta), selected from the group consisting of 5.7, 8.4, 11.4, 15.8, 18.1, 19.2, 21.1, 22.5, and 23.0.

4. The cocrystal of any one of embodiments 1-3, wherein the X-ray powder diffraction pattern comprises at least three peak positions, in degrees 2-theta (±0.2 degrees 2-theta), selected from the group consisting of 5.7, 8.4, 11.4, 15.8, 18.1, 19.2, 21.1, 22.5, and 23.0.

5. The cocrystal of any one of embodiments 1-4, wherein the X-ray powder diffraction pattern comprises at least four peak positions, in degrees 2-theta (±0.2 degrees 2-theta), selected from the group consisting of 5.7, 8.4, 11.4, 15.8, 18.1, 19.2, 21.1, 22.5, and 23.0.

6. The cocrystal of any one of embodiments 1-5 wherein the X-ray powder diffraction pattern comprises peak positions, in degrees 2-theta (±0.2 degrees 2-theta), of 5.7 and 8.4, and at least three peak positions select from the group consisting of 11.4, 15.8, 18.1, 19.2, 21.1, 22.5, and 23.0.

7. The cocrystal of any one of embodiments 1-6, wherein the cocrystal is characterized by a differential scanning calorimetry thermogram comprising an endothermic peak having an onset temperature of 170.6° C. (±2.0° C.).

8. The cocrystal of any one of embodiments 1-7, further comprising water.

9. The cocrystal of any one of embodiments 1-8, wherein the compound of formula (I), citric acid, and water are present in a molar ratio of 2:1:1.

10. The cocrystal of any one of embodiments 1-9, wherein the cocrystal comprises four molecules of the compound of formula (I), two citric acid molecules, and two water molecules per unit cell.

11. A drug substance comprising the cocrystal of any one of embodiments 1-10.

12. The drug substance of embodiment 11, wherein the drug substance contains no more than 1.0% (area % by HPLC) of (R)-6-(6-chloropyridin-2-yl)-$N^2$-(1,1,1-trifluoropropan-2-yl)-1,3,5-triazine-2,4-diamine.

13. The drug substance of embodiment 11 or 12, wherein the drug substance contains no more than 1.0% (area % by HPLC) of (R)-6-(6-chloropyridin-2-yl)-$N^2$-ethyl-$N^4$-(1,1,1-trifluoropropan-2-yl)-1,3,5-triazine-2,4-diamine.

14. The drug substance of any one of embodiments 11-13, wherein the drug substance contains no more than 1.0% (area % by HPLC) of (R)-6-(6-chloropyridin-2-yl)-$N^2$-isopropyl-$N^4$-(1,1,1-trifluoropropan-2-yl)-1,3,5-triazine-2,4-diamine.

15. The drug substance of any one of embodiments 11-14, wherein the drug substance contains no more than 1.0% (area % by HPLC) of 6-(6-chloropyridin-2-yl)-$N^2$,$N^4$-bis((S)-1,1,1-trifluoropropan-2-yl)-1,3,5-triazine-2,4-diamine.

16. The drug substance of any one of embodiments 11-15, wherein the drug substance contains no more than 1.0% (area % by HPLC) of 6-(6-chloropyridin-2-yl)-$N^2$-((R)-1,1,1-trifluoropropan-2-yl)-N4-((S)-1,1,1-trifluoropropan-2-yl)-1,3,5-triazine-2,4-diamine.

17. The drug substance of any one of embodiments 11-16, wherein the drug substance contains no more than 1.0% (area % by HPLC) of (R)-4-(6-chloropyridin-2-yl)-6-((1,1,1-trifluoropropan-2-yl)amino)-1,3,5-triazin-2-ol.

18. The drug substance of any one of embodiments 11-17, wherein the drug substance contains no more than 1.0% (area % by HPLC) of (R)-4-chloro-6-(6-chloropyridin-2-yl)-N-(1,1,1-trifluoropropan-2-yl)-1,3,5-triazin-2-amine.

19. The drug substance of any one of embodiments 11-18, wherein the drug substance contains no more than 1.0% (area % by HPLC) of 6-(4,6-bis(((R)-1,1,1-trifluoropropan-2-yl)amino)-1,3,5-triazin-2-yl)pyridin-2-ol.

20. A pharmaceutical composition comprising a therapeutically effective amount of the cocrystal of any one of embodiments 1-10 or the drug substance of any one of embodiments 11-19 and one or more pharmaceutical excipients.

21. The pharmaceutical composition of embodiment 20, wherein the pharmaceutical composition comprises 1-10% w/w of the compound of formula (I).

22. The pharmaceutical composition of embodiment 20 or 21, wherein the pharmaceutical composition is in the form of an orally acceptable dosage form and comprises about 10 mg, about 25 mg, about 50 mg, about 100 mg, about 200 mg, or about 300 mg of the compound of formula (I).

23. The pharmaceutical composition of embodiment 22, wherein the pharmaceutical composition comprises about 10 mg or about 50 mg of the compound of formula (I).

24. The pharmaceutical composition of embodiment 20, wherein the pharmaceutical composition comprises 20-30% w/w of the compound of formula (I).

25. The pharmaceutical composition of embodiment 24, wherein the pharmaceutical composition is in the form of an orally acceptable dosage form and comprises about 10 mg, about 25 mg, about 50 mg, about 100 mg, about 200 mg, or about 300 mg of the compound of formula (I).

26. The pharmaceutical composition of embodiment 25, wherein the pharmaceutical composition comprises about 10 mg or about 50 mg of the compound of formula (I).

27. A pharmaceutical composition prepared by a process comprising:

mixing a therapeutically effective amount of the cocrystal of any one of embodiments 1-10 or the drug substance of any one of embodiments 11-19 with one or more pharmaceutical excipients to afford the pharmaceutical composition.

28. A method of preparing a cocrystal comprising a compound of formula (I)

(I)

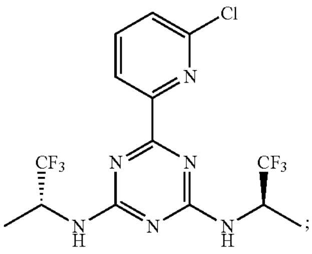

;

and citric acid, comprising:

dissolving the compound of formula (I) and citric acid in a solvent to afford a solution; and precipitating the cocrystal.

29. The method of embodiment 28, wherein the solvent comprises acetonitrile or acetone.

30. The method of embodiment 28 or 29, wherein said precipitating comprises cooling the solution.

31. The method of any one of embodiments 28-30, wherein said precipitating comprises evaporating a portion of the solvent from the solution.

32. The method of any one of embodiments 28-31, wherein said precipitating comprises adding an antisolvent to the solution.

33. The method of embodiment 32, wherein the antisolvent comprises a $C_5$-$C_{12}$ alkane or cycloalkane.

34. The method of embodiment 32, wherein the antisolvent comprises toluene or MTBE.

35. The method of any one of embodiments 28-34, wherein said precipitating comprises seeding the solution with crystals of the cocrystal.

36. The method of any one of embodiments 28-35, further comprising isolating the cocrystal.

37. A cocrystal comprising a compound of formula (I)

(I)

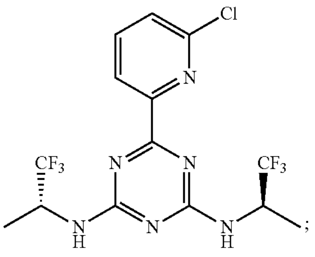

and maleic acid.

38. The cocrystal of embodiment 37, wherein the cocrystal is characterized by an X-ray powder diffraction pattern, acquired in reflection mode, comprising at least one peak position, in degrees 2-theta (±0.2 degrees 2-theta), selected from the group consisting of 5.9, 8.1, 15.0, 15.2, 16.9, 17.8, 18.5, 21.1, 23.4, 26.9, and 28.2.

39. The cocrystal of embodiment 37 or 38, wherein the X-ray powder diffraction pattern comprises at least two peak positions, in degrees 2-theta (±0.2 degrees 2-theta), selected from the group consisting of 5.9, 8.1, 15.0, 15.2, 16.9, 17.8, 18.5, 21.1, 23.4, 26.9, and 28.2.

40. The cocrystal of any one of embodiments 37-39, wherein the X-ray powder diffraction pattern comprises at least three peak positions, in degrees 2-theta (±0.2 degrees 2-theta), selected from the group consisting of 5.9, 8.1, 15.0, 15.2, 16.9, 17.8, 18.5, 21.1, 23.4, 26.9, and 28.2.

41. The cocrystal of any one of embodiments 37-40, wherein the X-ray powder diffraction pattern comprises at least four peak positions, in degrees 2-theta (±0.2 degrees 2-theta), selected from the group consisting of 5.9, 8.1, 15.0, 15.2, 16.9, 17.8, 18.5, 21.1, 23.4, 26.9, and 28.2.

42. The cocrystal of any one of embodiments 37-41 wherein the X-ray powder diffraction pattern comprises peak positions, in degrees 2-theta (±0.2 degrees 2-theta), of 8.1, 17.8, and 18.5, and at least three peak positions select from the group consisting of 5.9, 15.0, 15.2, 16.9, 21.1, 23.4, 26.9, and 28.2.

43. The cocrystal of any one of embodiments 37-42, wherein the cocrystal is characterized by a differential scanning calorimetry thermogram comprising endothermic peaks having onset temperatures of 91.2° C. and 128.4° C. (±2.0° C.).

44. The cocrystal of any one of embodiments 37-43, wherein the compound of formula (I) and maleic acid are present in a molar ratio of 1:1.

45. A pharmaceutical composition comprising a therapeutically effective amount of the cocrystal of any one of embodiments 37-44 and one or more pharmaceutical excipients.

46. The pharmaceutical composition of embodiment 45, wherein the pharmaceutical composition comprises 1-10% w/w of the compound of formula (I).

47. The pharmaceutical composition of embodiment 45 or 46, wherein the pharmaceutical composition is in the form of an orally acceptable dosage form and comprises about 10 mg, about 25 mg, about 50 mg, about 100 mg, about 200 mg, or about 300 mg of the compound of formula (I).

48. The pharmaceutical composition of embodiment 47, wherein the pharmaceutical composition comprises about 10 mg or about 50 mg of the compound of formula (I).

49. The pharmaceutical composition of embodiment 45, wherein the pharmaceutical composition comprises 20-30% w/w of the compound of formula (I).

50. The pharmaceutical composition of embodiment 49, wherein the pharmaceutical composition is in the form of an orally acceptable dosage form and comprises about 10 mg, about 25 mg, about 50 mg, about 100 mg, about 200 mg, or about 300 mg of the compound of formula (I).

51. The pharmaceutical composition of embodiment 50, wherein the pharmaceutical composition comprises about 10 mg or about 50 mg of the compound of formula (I).

52. A pharmaceutical composition prepared by a process comprising:

mixing a therapeutically effective amount of the cocrystal of any one of embodiments 37-44 with one or more pharmaceutical excipients to afford the pharmaceutical composition.

53. A method of preparing a cocrystal comprising a compound of formula (I)

(I)

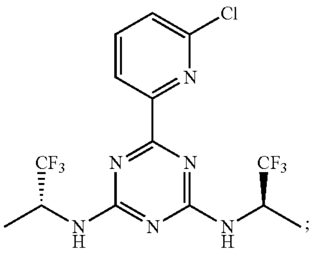

and maleic acid, comprising:

dissolving the compound of formula (I) and maleic acid in a solvent to afford a solution; and precipitating the cocrystal.

54. The method of embodiment 53, wherein the solvent comprises acetonitrile or acetone.

55. The method of embodiment 53 or 54, wherein said precipitating comprises seeding the solution with crystals of the cocrystal.

56. The method of any one of embodiments 53-55, further comprising isolating the cocrystal.

57. A crystalline form of a compound of formula (I)

(I)

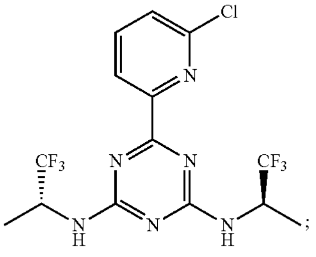

wherein the crystalline form is characterized by an X-ray powder diffraction pattern, acquired in reflection mode, comprising at least one peak position, in degrees 2-theta (±0.2 degrees 2-theta), selected from the group consisting of 11.7, 12.8, 14.2, 17.8, 19.8, 20.7, 21.8, 22.2, and 25.0.

58. The crystalline form of embodiment 57, wherein the X-ray powder diffraction pattern comprises at least two peak positions, in degrees 2-theta (±0.2 degrees 2-theta), selected from the group consisting of 11.7, 12.8, 14.2, 17.8, 19.8, 20.7, 21.8, 22.2, and 25.0.

59. The crystalline form of embodiment 57 or 58, wherein the X-ray powder diffraction pattern comprises at least three peak positions, in degrees 2-theta (±0.2 degrees 2-theta), selected from the group consisting of 11.7, 12.8, 14.2, 17.8, 19.8, 20.7, 21.8, 22.2, and 25.0.

60. The crystalline form of any one of embodiments 57-59, wherein the X-ray powder diffraction pattern comprises at least four peak positions, in degrees 2-theta (±0.2 degrees 2-theta), selected from the group consisting of 11.7, 12.8, 14.2, 17.8, 19.8, 20.7, 21.8, 22.2, and 25.0.

61. The crystalline form of any one of embodiments 57-60 wherein the X-ray powder diffraction pattern comprises peak positions, in degrees 2-theta (±0.2 degrees 2-theta), of 11.7, 17.8, and 21.8, and at least three peak positions select from the group consisting of 12.8, 14.2, 19.8, 20.7, 22.2, and 25.0.

62. The crystalline form of any one of embodiments 57-61, wherein the crystalline form is characterized by a differential scanning calorimetry thermogram comprising an endothermic peak having an onset temperature of 221.9° C. (±2.0° C.).

63. A drug substance comprising the crystalline form of any one of embodiments 57-62.

64. The drug substance of embodiment 63, wherein the drug substance contains no more than 1.0% (area % by HPLC) of (R)-6-(6-chloropyridin-2-yl)-$N^2$-(1,1,1-trifluoropropan-2-yl)-1,3,5-triazine-2,4-diamine.

65. The drug substance of embodiment 63 or 64, wherein the drug substance contains no more than 1.0% (area % by HPLC) of (R)-6-(6-chloropyridin-2-yl)-$N^2$-ethyl-$N^4$-(1,1,1-trifluoropropan-2-yl)-1,3,5-triazine-2,4-diamine.

66. The drug substance of any one of embodiments 63-65, wherein the drug substance contains no more than 1.0% (area % by HPLC) of (R)-6-(6-chloropyridin-2-yl)-$N^2$-isopropyl-$N^4$-(1,1,1-trifluoropropan-2-yl)-1,3,5-triazine-2,4-diamine.

67. The drug substance of any one of embodiments 63-66, wherein the drug substance contains no more than 1.0% (area % by HPLC) of 6-(6-chloropyridin-2-yl)-$N^2$,$N^4$-bis((S)-1,1,1-trifluoropropan-2-yl)-1,3,5-triazine-2,4-diamine.

68. The drug substance of any one of embodiments 63-67, wherein the drug substance contains no more than 1.0% (area % by HPLC) of 6-(6-chloropyridin-2-yl)-$N^2$-((R)-1,1,1-trifluoropropan-2-yl)-N4-((S)-1,1,1-trifluoropropan-2-yl)-1,3,5-triazine-2,4-diamine.

69. The drug substance of any one of embodiments 63-68, wherein the drug substance contains no more than 1.0% (area % by HPLC) of (R)-4-(6-chloropyridin-2-yl)-6-((1,1,1-trifluoropropan-2-yl)amino)-1,3,5-triazin-2-ol.

70. The drug substance of any one of embodiments 63-69, wherein the drug substance contains no more than 1.0% (area % by HPLC) of (R)-4-chloro-6-(6-chloropyridin-2-yl)-N-(1,1,1-trifluoropropan-2-yl)-1,3,5-triazin-2-amine.

71. The drug substance of any one of embodiments 63-70, wherein the drug substance contains no more than 1.0% (area % by HPLC) of 6-(4,6-bis(((R)-1,1,1-trifluoropropan-2-yl)amino)-1,3,5-triazin-2-yl)pyridin-2-ol.

72. A pharmaceutical composition comprising a therapeutically effective amount of the crystalline form of any one of embodiments 57-62 or the drug substance of any one of embodiments 63-71 and one or more pharmaceutical excipients.

73. The pharmaceutical composition of embodiment 72, wherein the pharmaceutical composition comprises 1-10% w/w of the compound of formula (I).

74. The pharmaceutical composition of embodiment 72 or 73, wherein the pharmaceutical composition is in the form of an orally acceptable dosage form and comprises about 10 mg, about 25 mg, about 50 mg, about 100 mg, about 200 mg, or about 300 mg of the compound of formula (I).

75. The pharmaceutical composition of embodiment 74, wherein the pharmaceutical composition comprises about 10 mg or about 50 mg of the compound of formula (I).

76. The pharmaceutical composition of embodiment 72, wherein the pharmaceutical composition comprises 20-30% w/w of the compound of formula (I).

77. The pharmaceutical composition of embodiment 76, wherein the pharmaceutical composition is in the form of an orally acceptable dosage form and comprises about 10 mg, about 25 mg, about 50 mg, about 100 mg, about 200 mg, or about 300 mg of the compound of formula (I).

78. The pharmaceutical composition of embodiment 77, wherein the pharmaceutical composition comprises about 10 mg or about 50 mg of the compound of formula (I).

79. A pharmaceutical composition prepared by a process comprising:

mixing a therapeutically effective amount of the crystalline form of any one of embodiments 57-62 or the drug substance of any one of embodiments 63-71 with one or more pharmaceutical excipients to afford the pharmaceutical composition.

80. A method of preparing a crystalline form of a compound of formula (I)

(I)

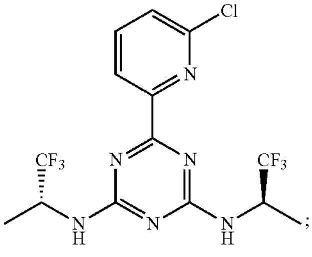

comprising:

dissolving the compound of formula (I) ethyl acetate to afford a solution; and precipitating the crystalline form.

81. The method of embodiment 80, wherein precipitating the crystalline form comprises adding heptane to the solution.

82. The method of embodiment 80 or 81, wherein said precipitating comprises seeding the solution with crystals of the crystalline form.

83. The method of any one of embodiments 80-82, further comprising isolating the crystalline form.

84. A crystalline form of a compound of formula (I)

(I)

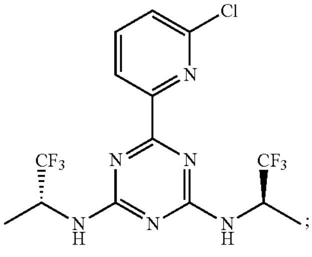

;

wherein the crystalline form is characterized by an X-ray powder diffraction pattern, acquired in reflection mode, comprising at least one peak position, in degrees 2-theta (±0.2 degrees 2-theta), selected from the group consisting of 11.9, 13.2, 15.5, 17.8, 18.6, 20.8, 23.2, 23.9, and 26.5.

85. The crystalline form of embodiment 84, wherein the X-ray powder diffraction pattern comprises at least two peak positions, in degrees 2-theta (±0.2 degrees 2-theta), selected from the group consisting of 11.9, 13.2, 15.5, 17.8, 18.6, 20.8, 23.2, 23.9, and 26.5.

86. The crystalline form of embodiment 84 or 85, wherein the X-ray powder diffraction pattern comprises at least three peak positions, in degrees 2-theta (±0.2 degrees 2-theta), selected from the group consisting of 11.9, 13.2, 15.5, 17.8, 18.6, 20.8, 23.2, 23.9, and 26.5.

87. The crystalline form of any one of embodiments 84-86, wherein the X-ray powder diffraction pattern comprises at least four peak positions, in degrees 2-theta (±0.2 degrees 2-theta), selected from the group consisting of 11.9, 13.2, 15.5, 17.8, 18.6, 20.8, 23.2, 23.9, and 26.5.

88. The crystalline form of any one of embodiments 84-87 wherein the X-ray powder diffraction pattern comprises peak positions, in degrees 2-theta (±0.2 degrees 2-theta), of 11.9, 17.8, and 23.9, and at least three peak positions select from the group consisting of 13.2, 15.5, 18.6, 20.8, 23.2, and 26.5.

89. The crystalline form of any one of embodiments 84-88, wherein the crystalline form is characterized by a differential scanning calorimetry thermogram comprising an endothermic peak having an onset temperature of 221.5° C. (±2.0° C.).

90. The crystalline form of any one of embodiments 84-89, wherein the crystalline form is anhydrous.

91. A pharmaceutical composition comprising a therapeutically effective amount of the crystalline form of any one of embodiments 84-90 and one or more pharmaceutical excipients.

92. The pharmaceutical composition of embodiment 91, wherein the pharmaceutical composition comprises 1-10% w/w of the compound of formula (I).

93. The pharmaceutical composition of embodiment 91 or 92, wherein the pharmaceutical composition is in the form of an orally acceptable dosage form and comprises about 10 mg, about 25 mg, about 50 mg, about 100 mg, about 200 mg, or about 300 mg of the compound of formula (I).

94. The pharmaceutical composition of embodiment 93, wherein the pharmaceutical composition comprises about 10 mg or about 50 mg of the compound of formula (I).

95. The pharmaceutical composition of embodiment 91, wherein the pharmaceutical composition comprises 20-30% w/w of the compound of formula (I).

96. The pharmaceutical composition of embodiment 95, wherein the pharmaceutical composition is in the form of an orally acceptable dosage form and comprises about 10 mg, about 25 mg, about 50 mg, about 100 mg, about 200 mg, or about 300 mg of the compound of formula (I).

97. The pharmaceutical composition of embodiment 96, wherein the pharmaceutical composition comprises about 10 mg or about 50 mg of the compound of formula (I).

98. A pharmaceutical composition prepared by a process comprising:

- mixing a therapeutically effective amount of the crystalline form of any one of embodiments 84-90 with one or more pharmaceutical excipients to afford the pharmaceutical composition.

99. A method of preparing a crystalline form of a compound of formula (I)

(I)

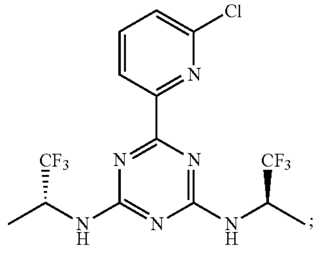

;

comprising:

- dissolving the compound of formula (I) in methyl isobutyl ketone to afford a solution; and
- precipitating the crystalline form.

100. The method of embodiment 99, wherein precipitating the crystalline form comprises adding heptane to the solution.

101. The method of embodiment 99 or 100, wherein said precipitating comprises seeding the solution with crystals of the crystalline form.

102. The method of any one of embodiments 99-101, further comprising isolating the crystalline form.

103. A crystalline form of a compound of formula (I)

(I)

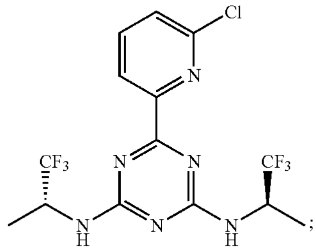

;

wherein the crystalline form is characterized by an X-ray powder diffraction pattern, acquired in reflection mode, comprising at least one peak position, in degrees 2-theta (±0.2 degrees 2-theta), selected from the group consisting of 8.6, 10.5, 18.2, 20.2, 21.1, and 25.9.

104. The crystalline form of embodiment 103, wherein the X-ray powder diffraction pattern comprises at least two peak positions, in degrees 2-theta (±0.2 degrees 2-theta), selected from the group consisting of 8.6, 10.5, 18.2, 20.2, 21.1, and 25.9.

105. The crystalline form of embodiment 103 or 104, wherein the X-ray powder diffraction pattern comprises at least three peak positions, in degrees 2-theta (±0.2 degrees 2-theta), selected from the group consisting of 8.6, 10.5, 18.2, 20.2, 21.1, and 25.9.

106. The crystalline form of any one of embodiments 103-105, wherein the X-ray powder diffraction pattern comprises at least four peak positions, in degrees 2-theta (±0.2 degrees 2-theta), selected from the group consisting of 8.6, 10.5, 18.2, 20.2, 21.1, and 25.9.

107. The crystalline form of any one of embodiments 103-106 wherein the X-ray powder diffraction pattern comprises peak positions, in degrees 2-theta (±0.2 degrees 2-theta), of 8.6 and 21.1, and at least three peak positions select from the group consisting of 8.6, 10.5, 18.2, 20.2, 21.1, and 25.9.

108. The crystalline form of any one of embodiments 103-107, wherein the crystalline form is characterized by a differential scanning calorimetry thermogram comprising an endothermic peak having an onset temperature of 221.3° C. (±2.0° C.).

109. The crystalline form of any one of embodiments 103-108, wherein the crystalline form is a trihydrate.

110. A pharmaceutical composition comprising a therapeutically effective amount of the crystalline form of any one of embodiments 103-109 and one or more pharmaceutical excipients.

111. The pharmaceutical composition of embodiment 110, wherein the pharmaceutical composition comprises 1-10% w/w of the compound of formula (I).

112. The pharmaceutical composition of embodiment 110 or 111, wherein the pharmaceutical composition is in the form of an orally acceptable dosage form and comprises about 10 mg, about 25 mg, about 50 mg, about 100 mg, about 200 mg, or about 300 mg of the compound of formula (I).

113. The pharmaceutical composition of embodiment 112, wherein the pharmaceutical composition comprises about 10 mg or about 50 mg of the compound of formula (I).

114. The pharmaceutical composition of embodiment 110, wherein the pharmaceutical composition comprises 20-30% w/w of the compound of formula (I).

115. The pharmaceutical composition of embodiment 114, wherein the pharmaceutical composition is in the form of an orally acceptable dosage form and comprises about 10 mg, about 25 mg, about 50 mg, about 100 mg, about 200 mg, or about 300 mg of the compound of formula (I).

116. The pharmaceutical composition of embodiment 115, wherein the pharmaceutical composition comprises about 10 mg or about 50 mg of the compound of formula (I).

117. A pharmaceutical composition prepared by a process comprising:

mixing a therapeutically effective amount of the crystalline form of any one of embodiments 103-109 with one or more pharmaceutical excipients to afford the pharmaceutical composition.

118. A method of preparing a crystalline form of a compound of formula (I)

(I)

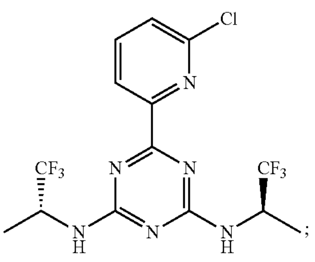

comprising:

dissolving the compound of formula (I) in dioxane to afford a solution; and precipitating the crystalline form.

119. The method of embodiment 118, wherein precipitating the crystalline form comprises adding water to the solution.

120. The method of embodiment 118 or 119, wherein said precipitating comprises seeding the solution with crystals of the crystalline form.

121. The method of any one of embodiments 118-120, further comprising isolating the crystalline form.

122. A crystalline form of a compound of formula (I)

(I)

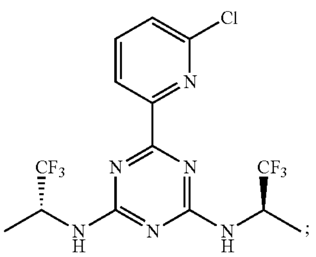

wherein the crystalline form is characterized by an X-ray powder diffraction pattern, acquired in reflection mode, comprising at least one peak position, in degrees 2-theta (±0.2 degrees 2-theta), selected from the group consisting of 8.6, 9.7, 10.5, 15.6, 15.9, 16.7, 17.9, 20.3, 21.2, 24.9, 26.6, and 27.0.

123. The crystalline form of embodiment 122, wherein the X-ray powder diffraction pattern comprises at least two peak positions, in degrees 2-theta (±0.2 degrees 2-theta), selected from the group consisting of 8.6, 9.7, 10.5, 15.6, 15.9, 16.7, 17.9, 20.3, 21.2, 24.9, 26.6, and 27.0.

124. The crystalline form of embodiment 122 or 123, wherein the X-ray powder diffraction pattern comprises at least three peak positions, in degrees 2-theta (±0.2 degrees 2-theta), selected from the group consisting of 8.6, 9.7, 10.5, 15.6, 15.9, 16.7, 17.9, 20.3, 21.2, 24.9, 26.6, and 27.0.

125. The crystalline form of any one of embodiments 122-124 wherein the X-ray powder diffraction pattern comprises at least four peak positions, in degrees 2-theta (±0.2 degrees 2-theta), selected from the group consisting of 8.6, 9.7, 10.5, 15.6, 15.9, 16.7, 17.9, 20.3, 21.2, 24.9, 26.6, and 27.0.

126. The crystalline form of any one of embodiments 122-125 wherein the X-ray powder diffraction pattern comprises peak positions, in degrees 2-theta (±0.2 degrees 2-theta), of 15.9, 16.7, and 21.2, and at least three peak positions select from the group consisting of 8.6, 9.7, 10.5, 15.6, 17.9, 20.3, 24.9, 26.6, and 27.0.

127. The crystalline form of any one of embodiments 122-126, wherein the crystalline form is characterized by a differential scanning calorimetry thermogram comprising an endothermic peak having an onset temperature of 221.3° C. (±2.0° C.).

128. The crystalline form of any one of embodiments 122-127, wherein the crystalline form is a dioxane solvate.

129. A pharmaceutical composition comprising a therapeutically effective amount of the crystalline form of any one of embodiments 122-128 and one or more pharmaceutical excipients.

130. The pharmaceutical composition of embodiment 129, wherein the pharmaceutical composition comprises 1-10% w/w of the compound of formula (I).

131. The pharmaceutical composition of embodiment 129 or 130, wherein the pharmaceutical composition is in the form of an orally acceptable dosage form and comprises about 10 mg, about 25 mg, about 50 mg, about 100 mg, about 200 mg, or about 300 mg of the compound of formula (I).

132. The pharmaceutical composition of embodiment 131, wherein the pharmaceutical composition comprises about 10 mg or about 50 mg the compound of formula (I).

133. The pharmaceutical composition of embodiment 29, wherein the pharmaceutical composition comprises 20-30% w/w of the compound of formula (I).

134. The pharmaceutical composition of embodiment 133, wherein the pharmaceutical composition is in the form of an orally acceptable dosage form and comprises about 10 mg, about 25 mg, about 50 mg, about 100 mg, about 200 mg, or about 300 mg of the compound of formula (I).

135. The pharmaceutical composition of embodiment 134, wherein the pharmaceutical composition comprises about 10 mg or about 50 mg of the compound of formula (I).

136. A pharmaceutical composition prepared by a process comprising:

mixing a therapeutically effective amount of the crystalline form of any one of embodiments 122-128 with one or more pharmaceutical excipients to afford the pharmaceutical composition.

137. An amorphous solid dispersion comprising a compound of formula (I)

(I)

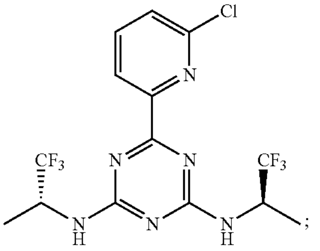

and a polymer.

138. The amorphous solid dispersion of embodiment 137, wherein the polymer is HPMCAS.

139. The amorphous solid dispersion of embodiment 138, wherein the compound of formula (I) and HPMCAS are present in a weight ratio of about 1:1.

140. A method of preparing an amorphous solid dispersion of a compound of formula (I)

(I)

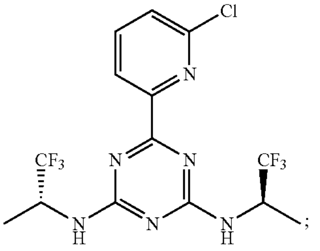

comprising:

mixing the compound of formula (I), a polymer, and a solvent to afford a mixture; and spray-drying the mixture to afford the amorphous solid dispersion.

141. The method of embodiment 140, wherein the compound of formula (I) used in said mixing is in the form of a cocrystal characterized by an X-ray powder diffraction pattern, acquired in reflection mode, comprising at least one peak position, in degrees 2-theta (±0.2 degrees 2-theta), selected from the group consisting of 5.7, 8.4, 11.4, 15.8, 18.1, 19.2, 21.1, 22.5, and 23.0.

142. The method of embodiment 140, wherein the compound of formula (I) used in said mixing is in the form of a cocrystal characterized by an X-ray powder diffraction pattern, acquired in reflection mode, comprising at least one peak position, in degrees 2-theta (±0.2 degrees 2-theta), selected from the group consisting of 5.9, 8.1, 15.0, 15.2, 16.9, 17.8, 18.5, 21.1, 23.4, 26.9, and 28.2.

143. The method of embodiment 140, wherein the compound of formula (I) used in said mixing is in a crystalline form characterized by an X-ray powder diffraction pattern, acquired in reflection mode, comprising at least one peak position, in degrees 2-theta (±0.2 degrees 2-theta), selected from the group consisting of 11.7, 12.8, 14.2, 17.8, 19.8, 20.7, 21.8, 22.2, and 25.0.

144. The method of embodiment 140, wherein the compound of formula (I) used in said mixing is in a crystalline form characterized by an X-ray powder diffraction pattern, acquired in reflection mode, comprising at least one peak position, in degrees 2-theta (±0.2 degrees 2-theta), selected from the group consisting of 11.9, 13.2, 15.5, 17.8, 18.6, 20.8, 23.2, 23.9, and 26.5.

145. The method of embodiment 140, wherein the compound of formula (I) used in said mixing is in a crystalline form characterized by an X-ray powder diffraction pattern, acquired in reflection mode, comprising at least one peak position, in degrees 2-theta (±0.2 degrees 2-theta), selected from the group consisting of 8.6, 10.5, 18.2, 20.2, 21.1, and 25.9.

146. The method of embodiment 140, wherein the compound of formula (I) used in said mixing is in a crystalline form characterized by an X-ray powder diffraction pattern, acquired in reflection mode, comprising at least one peak position, in degrees 2-theta (±0.2 degrees 2-theta), selected from the group consisting of 8.6, 9.7, 10.5, 15.6, 15.9, 16.7, 17.9, 20.3, 21.2, 24.9, 26.6, and 27.0.

147. A pharmaceutical composition comprising a therapeutically effective amount of the amorphous solid dispersion of any one of embodiments 137-139 and one or more pharmaceutical excipients.

148. The pharmaceutical composition of embodiment 147, wherein the pharmaceutical composition comprises 1-10% w/w of the compound of formula (I).

149. The pharmaceutical composition of embodiment 147 or 148, wherein the pharmaceutical composition is in the form of an orally acceptable dosage form and comprises about 10 mg, about 25 mg, about 50 mg, about 100 mg, about 200 mg, or about 300 mg of the compound of formula (I).

150. The pharmaceutical composition of embodiment 149, wherein the pharmaceutical composition comprises about 10 mg or about 50 mg of the compound of formula (I).

151. The pharmaceutical composition of embodiment 147, wherein the pharmaceutical composition comprises 20-30% w/w of the compound of formula (I).

152. The pharmaceutical composition of embodiment 151, wherein the pharmaceutical composition is in the form of an orally acceptable dosage form and comprises about 10 mg, about 25 mg, about 50 mg, about 100 mg, about 200 mg, or about 300 mg of the compound of formula (I).

153. The pharmaceutical composition of embodiment 152, wherein the pharmaceutical composition comprises about 10 mg or about 50 mg of the compound of formula (I).

154. A pharmaceutical composition prepared by a process comprising:

mixing a therapeutically effective amount of the spray-dried dispersion of any one of embodiments 137-139 with one or more pharmaceutical excipients to afford the pharmaceutical composition.

155. A compound that is:

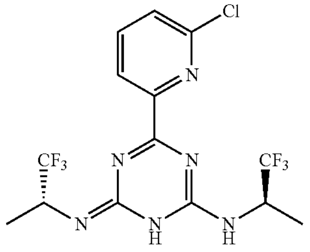 [SMILES: C[C@@H](/N=c1\nc(-c2cccc(Cl)n2)nc(N[C@H](C)C(F)(F)F)[nH]1)C(F)(F)F]

4-(6-chloropyridin-2-yl)-N—((R)-1,1,1-trifluoropropan-2-yl)-6-(((R)-1,1,1-trifluoropropan-2-yl)imino)-1,6-dihydro-1,3,5-triazin-2-amine;

or a pharmaceutically acceptable salt thereof.

156. A compound that is:

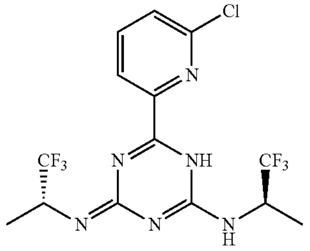 [SMILES: C[C@@H](/N=c1/nc(N[C@H](C)C(F)(F)F)[nH]c(-c2cccc(Cl)n2)n1)C(F)(F)F]

6-(6-chloropyridin-2-yl)-N—((R)-1,1,1-trifluoropropan-2-yl)-4-(((R)-1,1,1-trifluoropropan-2-yl)imino)-1,4-dihydro-1,3,5-triazin-2-amine;

or a pharmaceutically acceptable salt thereof.

157. A compound that is:

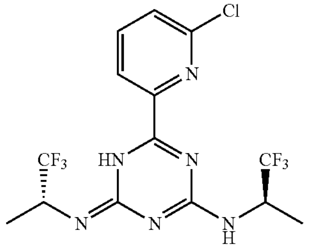 [SMILES: C[C@@H](/N=c1/nc(N[C@H](C)C(F)(F)F)nc(-c2cccc(Cl)n2)[nH]1)C(F)(F)F]

6-(6-chloropyridin-2-yl)-N—((R)-1,1,1-trifluoropropan-2-yl)-4-(((R)-1,1,1-trifluoropropan-2-yl)imino)-4,5-dihydro-1,3,5-triazin-2-amine;

or a pharmaceutically acceptable salt thereof.

158. A compound that is:

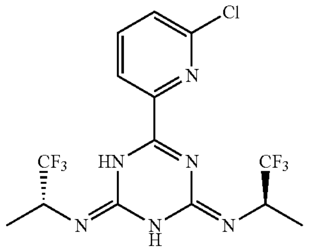 [SMILES: C[C@@H](/N=c1\nc(-c2cccc(Cl)n2)[nH]/c(=N\[C@H](C)C(F)(F)F)[nH]1)C(F)(F)F]

6-(6-chloropyridin-2-yl)-N2,N4-bis((R)-1,1,1-trifluoropropan-2-yl)-1,3,5-triazine-2,4(1H,3H)-diimine;

or a pharmaceutically acceptable salt thereof.

159. A pharmaceutical composition comprising a therapeutically effective amount of the compound of any one of embodiments 114-117, or a pharmaceutically acceptable salt thereof, and one or more pharmaceutical excipients.

160. A method of treating a cancer characterized by the presence of an IDH1 or IDH2 mutation in a patient in need thereof, comprising administering a therapeutically effective amount of the cocrystal of any one of embodiments 1-10 and 37-44, the crystalline form of any one of embodiments 57-62, 84-90, 103-109, and 122-128, the amorphous solid dispersion of any one of embodiments 137-139, the drug substance of any one of embodiments 11-19 and 63-71, the compound or pharmaceutically acceptable salt of any one of embodiments 155-158, or the pharmaceutical composition of any one of embodiments 20-27, 45-52, 72-79, 91-98, 110-117, 129-136, 147-154, and 159, to the patient.

161. The method of embodiment 160, wherein the cancer is characterized by the presence of an IDH1 mutation.

162. The method of embodiment 161, wherein the IDH1 mutation is an R132X mutation.

163. The method of embodiment 161, wherein the IDH1 mutation is an R132H or R132C mutation.

164. The method of any one of embodiments 161-163, wherein the IDH1 mutation results in accumulation of R(−)-2-hydroxyglutarate in the patient.

165. The method of embodiment 160, wherein the cancer is characterized by the presence of an IDH2 mutation.

166. The method of embodiment 165, wherein the IDH2 mutation is an R140X mutation.

167. The method of embodiment 165, wherein the IDH2 mutation is an R1400, R140W, or R140L mutation.

168. The method of embodiment 165, wherein the IDH2 mutation is an R172X mutation.

169. The method of embodiment 165, wherein the IDH2 mutation is an R172K or R172G mutation.

170. The method of any one of embodiments 165-169, wherein the IDH2 mutation results in accumulation of R(−)-2-hydroxyglutarate in the patient.

171. A method of treating a cancer characterized by the presence of an IDH1 mutation and an IDH2 mutation in a patient in need thereof, comprising administering a therapeutically effective amount of the cocrystal of any one of embodiments 1-10 and 37-44, the crystalline form of any one of embodiments 57-62, 84-90, 103-109, and 122-128, the amorphous solid dispersion of any one of embodiments 137-139, the drug substance of any one of embodiments 11-19 and 63-71, the compound or pharmaceutically acceptable salt of any one of embodiments 155-158, or the pharmaceutical composition of any one of embodiments 20-27, 45-52, 72-79, 91-98, 110-117, 129-136, 147-154, and 159, to the patient.

172. The method of any one of embodiments 160-171, wherein the cancer is selected from glioma, acute myelogenous leukemia, sarcoma, melanoma, non-small cell lung cancer (NSCLC), cholangiocarcinomas, chondrosarcoma, myelodysplastic syndromes (MDS), myeloproliferative neoplasm (MPN), colon cancer, and angio-immunoblastic non-Hodgkin's lymphoma (NHL).

173. The method of any one of embodiments 160-172, wherein the cancer is glioma.

174. The method of embodiment 173, wherein the glioma is a low grade glioma or a secondary high grade glioma.

175. The method of embodiment 173 or 174, wherein the glioma is a secondary high grade glioma, and the secondary high grade glioma is glioblastoma.
176. The method of any one of embodiments 160-175, wherein the cancer is refractory or relapsed.
177. The method of any one of embodiment 160-175, wherein the cancer is newly diagnosed or previously untreated.
178. The method of any one of embodiments 160-177, further comprising co-administering an additional therapy to the patient.
179. The method of any one of embodiments 160-178, wherein the patient was previously administered a cancer therapy for the cancer.
180. The method of any one of embodiments 160-179, wherein the cocrystal, crystalline form, amorphous solid dispersion, drug substance, compound or pharmaceutically acceptable salt, or pharmaceutical composition is administered in an amount of about 10 mg, about 25 mg, about 50 mg, about 100 mg, about 200 mg, or about 300 mg per day, based on the amount of the compound of formula (I).
181. The method of any one of embodiments 160-179, wherein the cocrystal, crystalline form, amorphous solid dispersion, drug substance, compound or pharmaceutically acceptable salt, or pharmaceutical composition is administered in an amount of about 10 mg or about 50 mg per day, based on the amount of the compound of formula (I).
182. The method of any one of embodiments 160-179, wherein the cocrystal, crystalline form, amorphous solid dispersion, drug substance, compound or pharmaceutically acceptable salt, or pharmaceutical composition is administered in an amount of about 10 mg, about 25 mg, about 50 mg, about 100 mg, about 200 mg, or about 300 mg, twice per day, based on the amount of the compound of formula (I).
183. The method of any one of embodiments 160-179, wherein the cocrystal, crystalline form, amorphous solid dispersion, drug substance, compound or pharmaceutically acceptable salt, or pharmaceutical composition is administered in an amount of about 10 mg or about 50 mg, twice per day, based on the amount of the compound of formula (I).
184. A compound selected from the group consisting of:
(R)-6-(6-chloropyridin-2-yl)-$N^2$-(1,1,1-trifluoropropan-2-yl)-1,3,5-triazine-2,4-diamine;
(R)-6-(6-chloropyridin-2-yl)-$N^2$-ethyl-$N^4$-(1,1,1-trifluoropropan-2-yl)-1,3,5-triazine-2,4-diamine;
(R)-6-(6-chloropyridin-2-yl)-$N^2$-isopropyl-$N^4$-(1,1,1-trifluoropropan-2-yl)-1,3,5-triazine-2,4-diamine;
(R)-4-(6-chloropyridin-2-yl)-6-((1,1,1-trifluoropropan-2-yl)amino)-1,3,5-triazin-2-ol;
(R)-4-chloro-6-(6-chloropyridin-2-yl)-N-(1,1,1-trifluoropropan-2-yl)-1,3,5-triazin-2-amine; and
6-(4,6-bis(((R)-1,1,1-trifluoropropan-2-yl)amino)-1,3,5-triazin-2-yl)pyridin-2-ol.

EXAMPLES

General Experimental Notes

In the following examples, except where otherwise noted, the reagents (chemicals) were purchased from commercial sources (such as Alfa, Acros, Sigma Aldrich, TCI and Shanghai Chemical Reagent Company), and used without further purification.

Instrumentation and Methods

X-Ray Powder Diffraction (XRPD) Analysis. XRPD analysis was conducted on either a PANalytical Empyrean X-ray powder diffractometer with a 12-auto sample stage or a Bruker D8 Advance X-ray powder diffractometer.

The parameters used for XRPD analysis on the PANalytical Empyrean diffractometer are provided in Table 2.

TABLE 2

XRPD Parameters (PANalytical Empyrean diffractometer)

| Parameter | Value |
|---|---|
| X-Ray wavelength | Cu, kα,<br>Kα1 (Å): 1.540598, Kα2 (Å): 1.544426<br>Kα2/Kα1 intensity ratio: 0.50 |
| X-Ray tube setting | 45 kV, 40 mA |
| Divergence slit | Automatic |
| Scan mode | Continuous |
| Scan range (°2 Theta) | 3°-40° |
| Step Size (°2 Theta) | 0.0170 |
| Scan Speed (°2 Theta/minute) | About 10 |

The parameters used for XRPD analysis on the Bruker D8 Advance diffractometer are provided in Table 3.

TABLE 3

XRPD Parameters (Bruker D8 Advance diffractometer)

| Parameter | Value |
|---|---|
| X-Ray Generator | Cu, k-Alpha1, (λ = 1.54060 Å) |
| Tube Current (mA) | 40 |
| Primary Soller Slit (deg) | 2.5 |
| Detector Slit (mm) | 10.5 |
| Scan axis | 2-Theta/Theta |
| Scan Speed (deg/min) | 10 |
| Tube Voltage (kV) | 40 |
| Divergence Slit (mm) | 0.60 |
| Secondary Soller Slit (deg) | 2.5 |
| Antiscatterin Slit (mm) | 7.1 |
| Step size (deg) | 0.02 |
| Scanning Scope (deg) | 4-40 |

$^1H$ and $^{13}C$ NMR Analysis. Unless otherwise specified, $^1H$ and $^{13}C$ Liquid NMR spectra were collected on a Bruker 400 MHz NMR Spectrometer.

Dynamic Vapor Sorption (DVS) Analysis. DVS was measured via a SMS (Surface Measurement Systems) DVS Intrinsic. The relative humidity at 25° C. were calibrated against deliquescence point of LiCl, $Mg(NO_3)_2$ and KCl. The parameters used for DVS analysis are listed in Table 4.

TABLE 4

DVS Analysis Parameters

| Parameter | Value |
|---|---|
| Temperature | 25° C. |
| Sample size | 10-20 mg |
| Gas and flow rate | $N_2$, 200 mL/min |
| dm/dt | 0.002%/min |
| Minimum dm/dt stability duration | 10 minutes |
| Maximum equilibrium time | 180 minutes |
| Relative humidity range | 95%-0%-95% |

High Performance Liquid Chromatography (HPLC) Analysis—Method 1. A gradient reversed-phase HPLC procedure identified herein as HPLC Method 1 was performed under the conditions described in Table 5.

TABLE 5

| HPLC Method 1 Conditions | |
|---|---|
| Column | Inertsil ODS-3, 4.6 mm × 250 mm, 5 μm |
| Column temperature | 35° C. |
| Mobile Phase A | 0.05% $H_3PO_4$ in water, v/v |
| Mobile Phase B | Acetonitrile/Methanol: 90/10, v/v with 0.05% $H_3PO_4$ |
| Diluent | Acetonitrile/Water = 80/20 (v/v) |
| Flow Rate | 1.0 mL/min |
| Detection | 220 nm |
| Injection volume | 5 μL |
| Run time | 40 minutes |
| Gradient Program | Analysis was conducted over a gradient elution program employing Mobile Phase A (5-60%) and Mobile Phase B (40-95%). |

High Performance Liquid Chromatography (HPLC) Analysis—Method 2. An isocratic normal phase HPLC procedure identified herein as HPLC Method 2 was performed under the conditions described in Table 6.

TABLE 6

| HPLC Method 2 Conditions | |
|---|---|
| Column | Chiralpak AD-H, 250 × 4.6 mm 5 μm column |
| Column temperature | 40° C. |
| Mobile phase | n-Hexane:Isopropanol: 95.5 (v/v) |
| Diluent | Isopropanol |
| Flow rate | 0.8 mL/min |
| Detection | 220 mn |
| Injection volume | 4 μL |
| Rise time | 25 minutes |

Example 1

Preparation of 6-(6-chloropyridin-2-yl)-$N^2$,$N^4$-bis((R)-1,1,1-trifluoropropan-2-yl)-1,3,5-triazine-2,4-diamine (Compound 1)

Compound 1

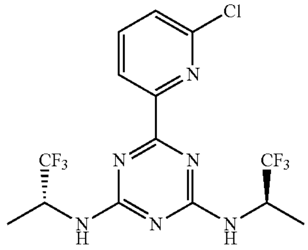

A synthesis of 6-(6-chloropyridin-2-yl)-$N^2$,$N^4$-bis((R)-1,1,1-trifluoropropan-2-yl)-1,3,5-triazine-2,4-diamine, which is referred to in the Examples as Compound 1, is described in paragraphs [1032]-[1036] of U.S. Publication No. 2015/0018328 A1, which paragraphs are incorporated herein by reference.

Under some conditions, Compound 1 exists at least in part in one or more tautomeric forms, including without limitation one or more of the following:

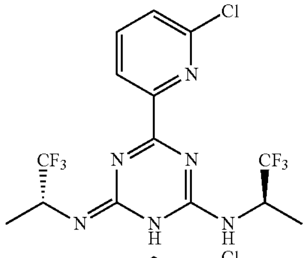

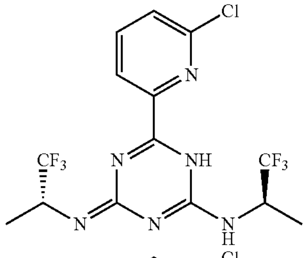

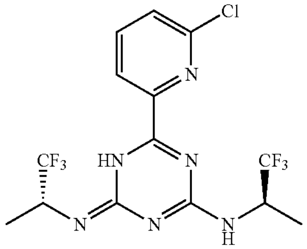

As used in the Examples, the term "Compound 1" shall be understood to refer to 6-(6-chloropyridin-2-yl)-$N^2$,$N^4$-bis((R)-1,1,1-trifluoropropan-2-yl)-1,3,5-triazine-2,4-diamine or any tautomer(s) thereof. The double bond geometries of the foregoing tautomers were not determined, and therefore the chemical structures representing the foregoing tautomers are not intended to imply a particular double bond geometry.

The existence of one or more tautomers was determined by solution phase $^1H$, $^{13}C$, and $^{15}N$ NMR spectroscopy. NMR spectra were collected on a Varian Unity Inova 500 MHz NMR spectrometer equipped with a pentaprobe and a broadband probe. Samples of Compound 1 were dissolved in $CD_3OD$ or DMSO-d6 and the $^1H$ and $^{13}C$ NMR chemical shifts were referenced to the corresponding solvent peaks. The $^{15}N$ NMR chemical shifts were set using the vendor's "setref" macro.

Figure 2:
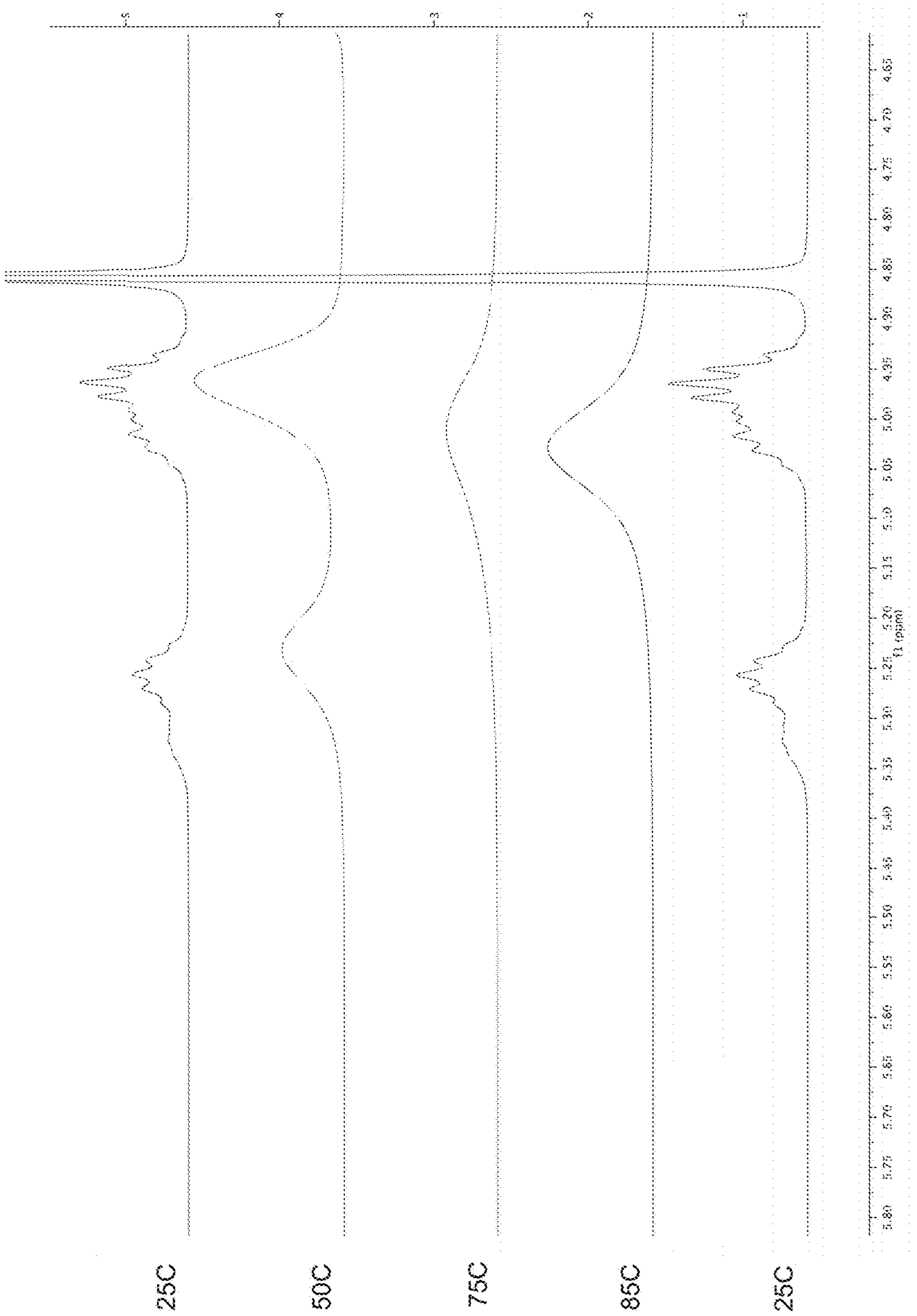
FIG. 2 depicts portions of one-dimensional $^{1}H$ NMR spectra of Compound 1 in CDOD, taken over a range of temperatures from 25° C. to 85° C.

One-dimensional $^1H$ NMR spectra of Compound 1 in CDMOD, taken over a range of temperatures from 25° C. to 85° C., are shown in FIGS. 1 and 2. The $^1H$ NMR spectra included multiple resonances in the methine region (4.90 to 5.40 ppm), which coalesced at elevated temperature (e.g., 85° C.), consistent with the existence of tautomerism.

Figure 3:
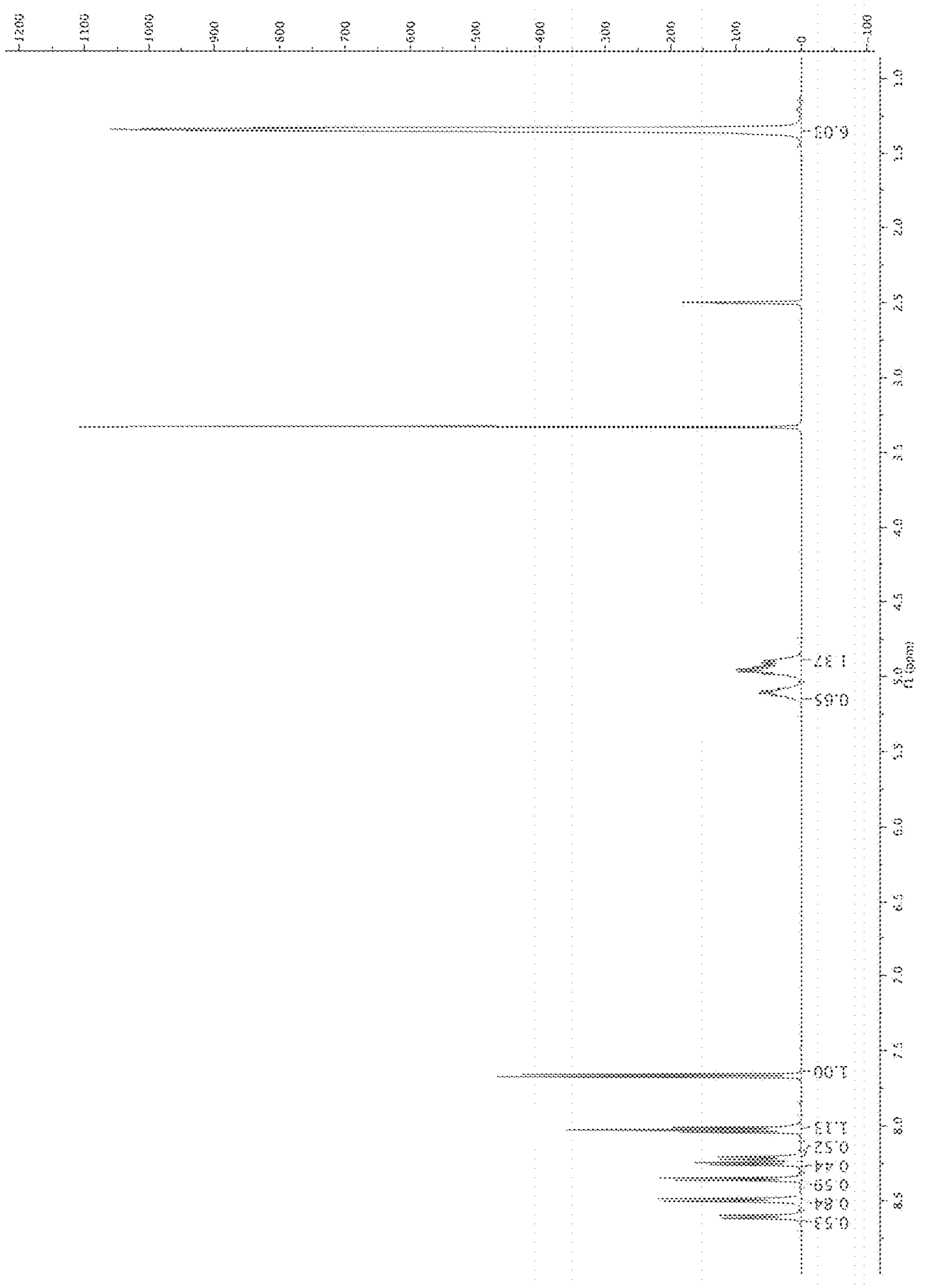
FIG. 3 depicts a one-dimensional $^{1}H$ NMR spectrum of Compound 1 in DMSO-d6.

The one-dimensional $^1H$ NMR spectrum of Compound 1 in DMSO-d6 (FIG. 3) also includes multiple —NH (8.21, 8.49, and 8.60 ppm), aromatic (8.25 and 8.35 ppm), and methine (4.94 and 5.11 ppm) resonances that would have been expected to appear as single resonances in the absence of tautomerism.

Figure 4:
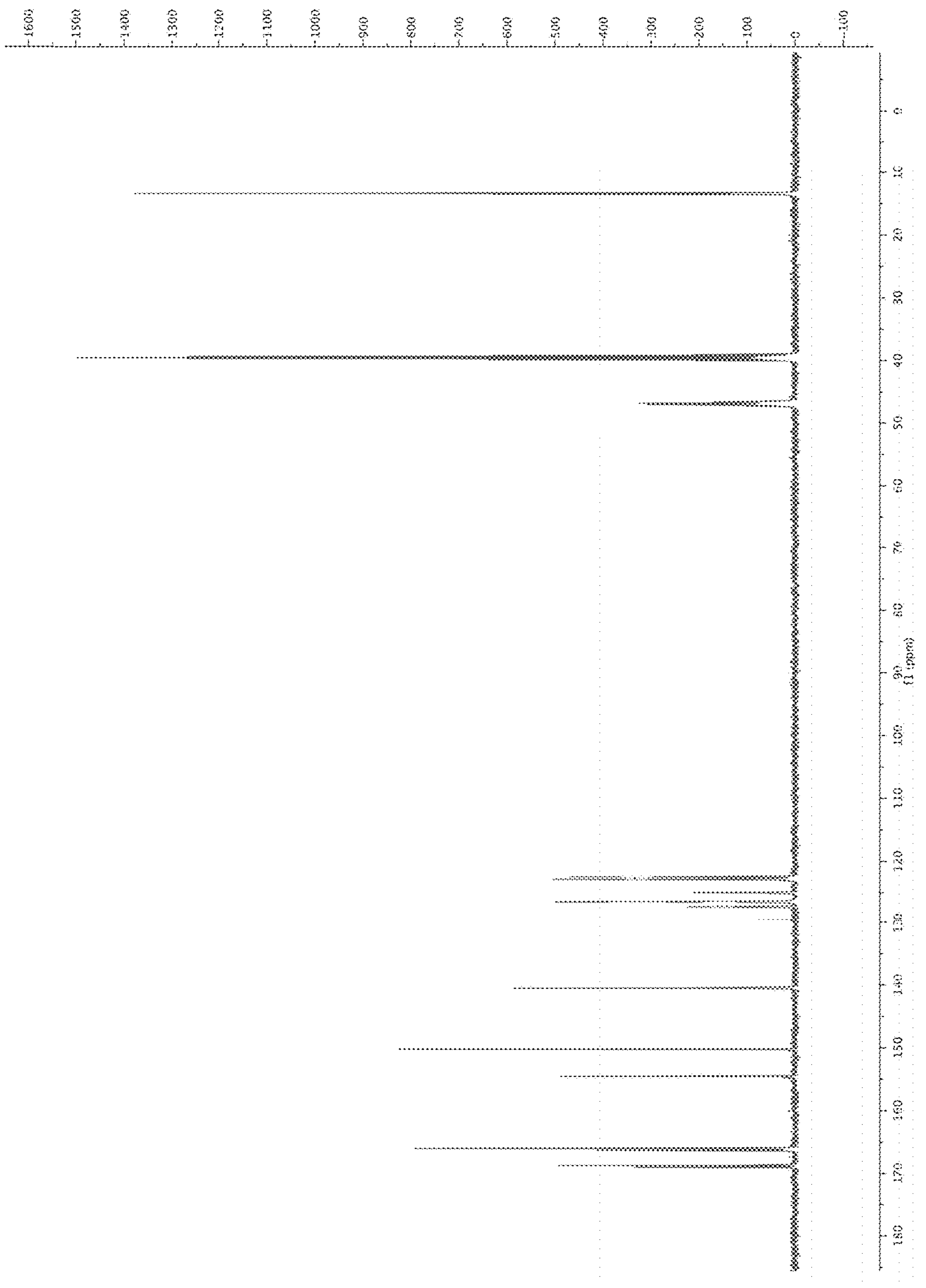
FIG. 4 depicts a one-dimensional $^{13}C$ NMR spectrum of Compound 1 in DMSO-d6.

The one-dimensional $^{13}C$ NMR spectrum of Compound 1 in DMSO-d6 (FIG. 4) also includes multiple resonances that would have been expected to appear as single resonances in the absence of tautomerism. For example, the spectrum includes two resonances corresponding to the methine carbons (46.8 and 47.1 ppm).

Figure 5:
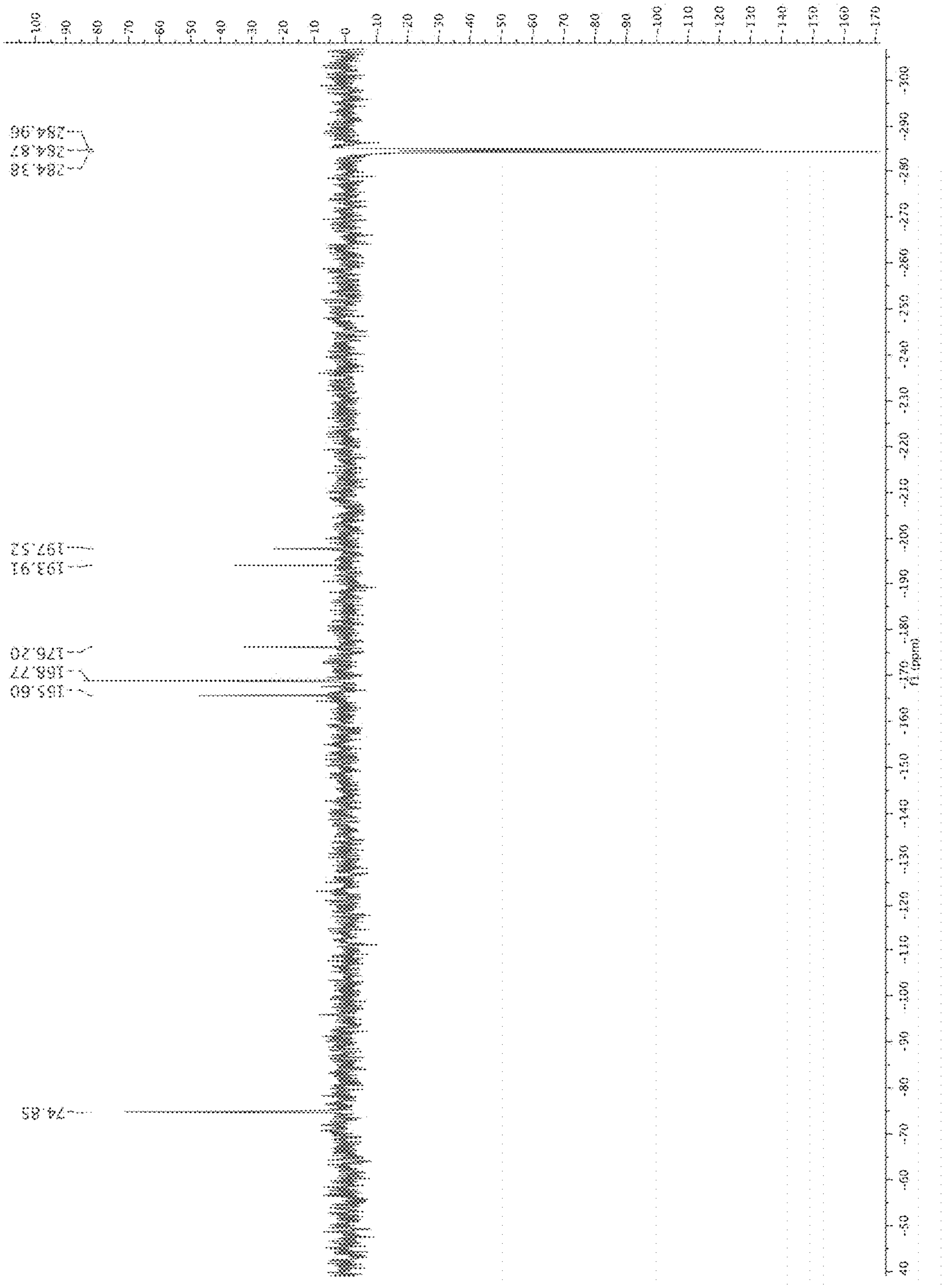
FIG. 5 depicts a one-dimensional NOE enhanced $^{15}N$ NMR spectrum of Compound 1 in DMSO-d6.

The one-dimensional NOE enhanced $^{15}N$ NMR spectrum of Compound 1 in DMSO-d6 (FIG. 5) also includes multiple resonances that would have been expected to appear as single resonances in the absence of tautomerism. For example, the spectrum includes three resonances corresponding to —NH groups (−285.0, −284.9, and −284.4 ppm).

Example 2

Preparation of (R)-4-chloro-6-(6-chloropyridin-2-yl)-N-(1,1,1-trifluoropropan-2-yl)-1,3,5-triazin-2-amine (Compound 2)

Compound 2

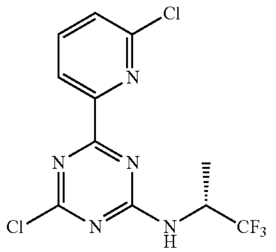

A 3 L three-neck round bottom flask was charged 2,4-dichloro-6-(6-chloropyridin-2-yl)-1,3,5-triazine (120 g, 458.9 mmol), a synthesis of which is described in paragraph [1034] of U.S. Publication No. 2015/0018328 A1, (R)-1,1,1-trifluoropropan-2-amine hydrochloride (72 g, 481.5 mmol), and 1,4-dioxane (960 mL). To the mixture was added N,N-diisopropylethylamine (DIPEA) (303 mL, 1.735 mol) drop wise below 30° C., and the resulting mixture was stirred at 45° C. for 2 h. The reaction mixture was concentrated under vacuum. To the residue was added water (1 L) and ethyl acetate (1 L). The layers were separated, and the organic layer was washed with water (1 L×2), dried over anhydrous sodium sulfate, and concentrated under vacuum. The residual material was purified by silica gel chromatography to afford (R)-4-chloro-6-(6-chloropyridin-2-yl)-N-(1,1,1-trifluoropropan-2-yl)-1,3,5-triazin-2-amine (Compound 2, 135 g) in 87% yield. LC-MS (Chromolith SpeedROD, RP-18e, 50*4.6 mm column eluting water/CH3CN over 5 minutes) found (M+1)=338. $^1$H NMR (CDC) δ 8.38-8.28 (m, 1H), 7.80-7.75 (m, 1H), 7.48-7.46 (m, 1H), 6.05-5.73 (m, 1H), 5.09-4.87 (m, 1H), 1.43-1.38 (m, 3H) ppm.

Example 3

Preparation of (R)-6-(6-chloropyridin-2-yl)-$N^2$-(1,1,1-trifluoropropan-2-yl)-1,3,5-triazine-2,4-diamine (Compound 3)

Compound 3

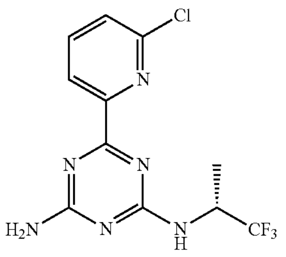

To a mixture of (R)-4-chloro-6-(6-chloropyridin-2-yl)-N-(1,1,1-trifluoropropan-2-yl)-1,3,5-triazin-2-amine (Compound 2, 20 g, 59.2 mmol) in tetrahydrofuran (THF) (100 mL) was added ammonium hydroxide ($NH_4OH$) (40 mL). The reaction mixture was stirred at 25° C. for 16h. To the mixture was added water (100 mL) and ethyl acetate (100 mL). The layers were separated, and the organic layer was washed with water (100 mL), dried over anhydrous sodium sulfate and concentrated under vacuum. The residual material was recrystallized from ethanol (36 mL) and n-heptanes (36 mL) to afford (R)-6-(6-chloropyridin-2-yl)-$N^2$-(1,1,1-trifluoropropan-2-yl)-1,3,5-triazine-2,4-diamine (Compound 3, 10.2 g) as a white solid in 54% yield. LC-MS (Chromolith SpeedROD, RP-18e, 50*4.6 mm column eluting water/CH3CN over 5 minutes) found (M+1)=319. $^1$H NMR (DMSO-$d_6$) δ 8.33-8.00 (m, 3H), 7.65 (d, 1H), 7.40-7.21 (m, 2H), 5.13-4.86 (m, 1H), 1.33 (d, 3H) ppm.

Example 4

Preparation of (R)-4-(6-chloropyridin-2-yl)-6-((1,1,1-trifluoropropan-2-yl)amino)-1,3,5-triazin-2-ol (Compound 4)

Compound 4

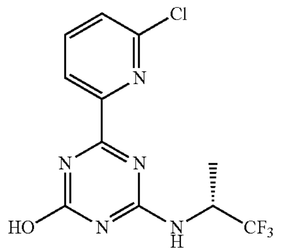

To a 1 L three-neck round bottom flask was charged (R)-4-chloro-6-(6-chloropyridin-2-yl)-N-(1,1,1-trifluoropropan-2-yl)-1,3,5-triazin-2-amine (Compound 2, 20 g, 59.2 mmol), N-methyl-2-pyrrolidone (NMP) (200 mL), sodium acetate (24 g, 292.6 mmol) and acetic acid (7.2 g, 119.9 mmol) at 25° C. The reaction mixture was heated at 100° C. for 4 h. The reaction mixture was cooled to room temperature, and water (1 L) and dichloromethane (DCM) (400 mL) were added. The layers were separated, and the organic layer was washed with water (200 mL×2), dried over anhydrous sodium sulfate and concentrated under vacuum. The residual was purified by silica gel chromatography and then triturated in ethyl acetate (30 mL) to afford (R)-4-(6-chloropyridin-2-yl)-6-((1,1,1-trifluoropropan-2-yl)amino)-1,3,5-triazin-2-ol (Compound 4, 10.4 g) as a white solid in 55% yield. LC-MS (Chromolith SpeedROD, RP-18e, 50*4.6 mm column eluting water/CH3CN over 5 minutes) found (M+1)=320. $^1$H NMR (DMSO-$d_6$) δ 11.85 (br. s, 1H), 8.78-8.13 (m, 3H), 7.84 (d, 1H), 5.16-4.86 (m, 1H), 1.34 (d, 3H) ppm.

Example 5

Preparation of (R)-6-(6-chloropyridin-2-yl)-$N^2$-isopropyl-$N^4$-(1,1,1-trifluoropropan-2-yl)-1,3,5-triazine-2,4-diamine Compound 5)

Compound 5

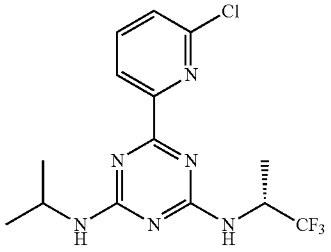

To a mixture of (R)-4-chloro-6-(6-chloropyridin-2-yl)-N-(1,1,1-trifluoropropan-2-yl)-1,3,5-triazin-2-amine (Compound 2, 30 g, 88.7 mmol) in tetrahydrofuran (THF) (100 mL) was added isopropylamine (15.3 mL, 186.4 mmol). The reaction mixture was stirred at 15-20° C. overnight and was then concentrated under vacuum. The residual material was recrystallized from ethyl acetate (70 mL) and n-heptane (140 mL) to afford (R)-6-(6-chloropyridin-2-yl)-$N^2$-isopropyl-$N^4$-(1,1,1-trifluoropropan-2-yl)-1,3,5-triazine-2,4-diamine (Compound 5, 20.4 g) as a white solid in 64% yield. LC-MS (Chromolith SpeedROD, RP-18e, 50*4.6 mm column eluting water/CH3CN over 5 minutes) found (M+1)=361. $^1$H NMR ($CDCl_3$) δ 8.25-8.19 (m, 1H), 7.72-7.68 (m, 1H), 7.38 (d, 1H), 5.39-5.33 (m, 2H), 5.03-4.86 (m, 1H), 4.15-4.08 (m, 1H), 1.35-1.29 (m, 3H), 1.19-1.17 (m, 6H) ppm.

Example 6

Preparation of (R)-6-(6-chloropyridin-2-yl)-$N^2$-ethyl-$N^4$-(1,1,1-trifluoropropan-2-yl)-1,3,5-triazine-2,4-diamine (Compound 6)

Compound 6

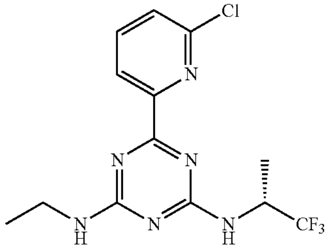

To a mixture of (R)-4-chloro-6-(6-chloropyridin-2-yl)-N-(1,1,1-trifluoropropan-2-yl)-1,3,5-triazin-2-amine (Compound 2, 30 g, 88.7 mmol) in tetrahydrofuran (THF) (100 mL) was added ethylamine (12 g, 65-70% in water). The reaction mixture was stirred at 15-20° C. overnight and was then concentrated under vacuum. The residual material was recrystallized from ethyl acetate (70 mL) and n-heptane (140 mL) to afford (R)-6-(6-chloropyridin-2-yl)-$N^2$-ethyl-$N^4$-(1,1,1-trifluoropropan-2-yl)-1,3,5-triazine-2,4-diamine (Compound 6, 20.2 g) as a white solid in 65% yield. LC-MS (Chromolith SpeedROD, RP-18e, 50*4.6 mm column eluting water/CH3CN over 5 minutes) found (M+1)=347. $^1$H NMR ($CDCl_3$) δ 8.25-8.19 (m, 1H), 7.72-7.68 (m, 1H), 7.38 (d, 1H), 5.52-5.16 (m, 2H), 4.94-4.88 (m, 1H), 3.54-3.35 (m, 2H), 1.35-1.29 (m, 3H), 1.20-1.14 (m, 3H) ppm.

Example 7

Preparation of 6-(4,6-bis(((R)-1,1,1-trifluoropropan-2-yl)amino)-1,3,5-triazin-2-yl)pyridin-2-ol (Compound 7)

Compound 7

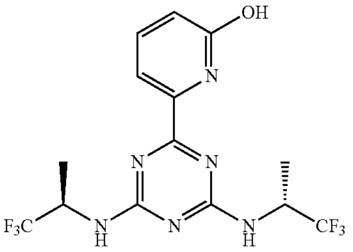

To a solution of sodium methoxide ($CH_3ONa$) (150 mL, 30 wt % in methanol) was added 6-(6-chloropyridin-2-yl)-$N^2$,$N^4$-bis((R)-1,1,1-trifluoropropan-2-yl)-1,3,5-triazine-2,4-diamine (Compound 1, 30 g, 72.3 mmol) in portions at 15-20° C. The reaction mixture was heated to reflux and stirred for 4 h. The reaction mixture was then cooled to room temperature and poured into ice-water (300 mL) below 10° C. To the reaction mixture was added dichloromethane (DCM) (500 mL). The layers were separated, and the organic layer was washed with water (200 mL×2), dried over anhydrous sodium sulfate and concentrated in vacuum to afford 6-(6-methoxypyridin-2-yl)-$N^2$,$N^4$-bis((R)-1,1,1-trifluoropropan-2-yl)-1,3,5-triazine-2,4-diamine (27 g) as a white solid in 90% yield. $^1$H NMR (DMSO-$d_6$) δ 8.31-8.12 (m, 2H), 7.92-7.83 (m, 2H), 6.99-6.97 (m, 1H), 5.10-4.93 (m, 2H), 3.94 (s, 3H), 1.35 (m, 6H) ppm.

A solution of 6-(6-methoxypyridin-2-yl)-$N^2$,$N^4$-bis((R)-1,1,1-trifluoropropan-2-yl)-1,3,5-triazine-2,4-diamine (20 g, 48.7 mmol) in hydrogen bromide (HBr) (200 mL, 40 wt % aqueous solution) was stirred at 100° C. for 4 h. The reaction mixture was cooled to room temperature, water (1 L) was added, and sodium hydroxide (1 N aqueous solution) was added to adjust pH to 7. The resulting slurry was filtered, and the solids were dissolved in ethyl acetate (200 mL). The organic layer was washed with water (200 mL×2), dried over anhydrous sodium sulfate and concentrated under vacuum to afford 6-(4,6-bis(((R)-1,1,1-trifluoropropan-2-yl)amino)-1,3,5-triazin-2-yl)pyridin-2-ol (Compound 7, 18 g) as a white solid in 93% yield. LC-MS (Chromolith SpeedROD, RP-18e, 50*4.6 mm column eluting water/CH3CN over 5 minutes) found (M+1)=397. $^1$H NMR (DMSO-d6) δ 11.32 (br. s, 1H), 8.48-8.00 (m, 2H), 7.63-7.56 (m, 1H), 7.33-7.18 (m, 1H), 6.62-6.58 (m, 1H), 5.66-5.45 (m, 1H), 5.00-4.87 (m, 1H), 1.30 (m, 6H) ppm.

Example 8

Preparation of 6-(6-chloropyridin-2-yl)-$N^2$-((R)-1,1,1-trifluoropropan-2-yl)-$N^4$-((S)-1,1,1-trifluoropropan-2-yl)-1,3,5-triazine-2,4-diamine (Compound 8)

Compound 8

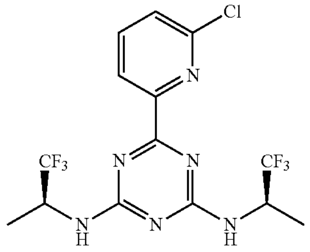

A synthesis of 6-(6-chloropyridin-2-yl)-$N^2$-((R)-1,1,1-trifluoropropan-2-yl)-$N^4$-((S)-1,1,1-trifluoropropan-2-yl)-1,3,5-triazine-2,4-diamine, which is referred to in the Examples as Compound 8, is described in paragraphs [1032]-[1034], [1037], and [1040]-[1041] of U.S. Publication No. 2015/0018328 A1, which paragraphs are incorporated herein by reference.

Example 9

Preparation of 6-(6-chloropyridin-2-yl)-$N^2$,$N^4$-bis((S)-1,1,1-trifluoropropan-2-yl)-1,3,5-triazine-2,4-diamine (Compound 9)

Compound 9

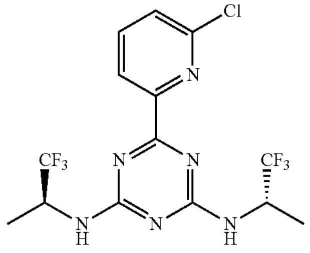

A synthesis of 6-(6-chloropyridin-2-yl)-$N^2$,$N^4$-bis((S)-1,1,1-trifluoropropan-2-yl)-1,3,5-triazine-2,4-diamine, which is referred to in the Examples as Compound 9, is described in paragraphs [1032]-[1034] and [1037]-[1039] of U.S. Publication No. 2015/0018328 A1, which paragraphs are incorporated herein by reference.

Example 10

Alternate Preparation of 6-(6-chloropyridin-2-yl)-$N^2$,$N^4$-bis((R)-1,1,1-trifluoropropan-2-yl)-1,3,5-triazine-2,4-diamine (Compound 1)

Compound 1

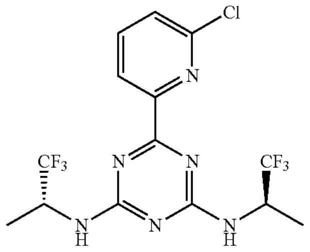

An alternate preparation of Compound 1 is described in Scheme 1.

Scheme 1. Alternate Preparation of Compound 1

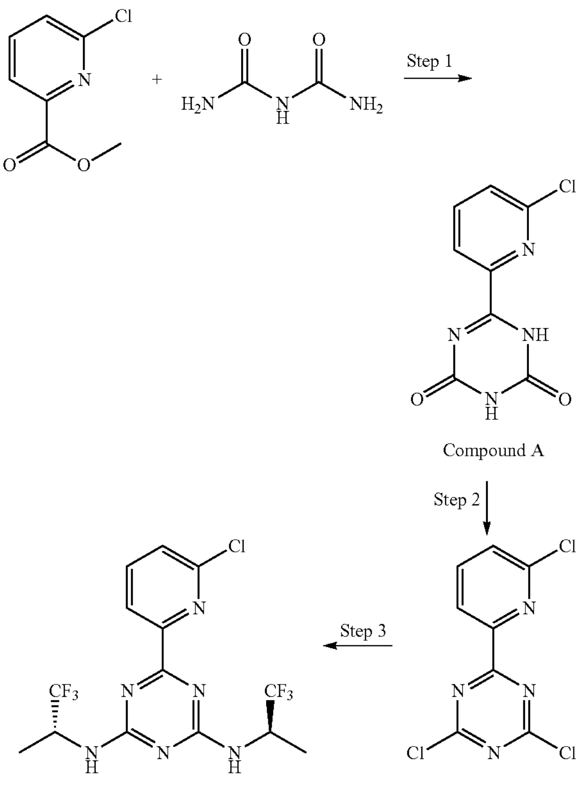

Compound A

Compound 1

Compound B

Step 1: Preparation of 6-(6-chloropyridin-2-yl)-1,3,5-triazine-2,4(1H,3H)-dione (Compound A)

A 2000 L reactor was charged with ethanol (344 kg), methyl 6-chloropicolinate (20.1 kg, 117.1 mol), and biuret (2-imidodicarbonic diamide) (14.85 kg, 140.5 mol). The resulting mixture was warmed to 30-35° C. and stirred at this temperature for 30-60 min, at which time trimethyl orthoformate (15.4 kg, 140.5 mol) and trifluoroacetic acid (1.4 kg, 12.3 mol) were added. The resulting mixture was warmed to 50-55° C., stirred at this temperature for 2 hours, and then cooled to 25-30° C. Water (200 kg) was added, and the pH was adjusted to ≤1 by addition of HCl (35% aqueous). The mixture was stirred at 30-35° C. for 2-4 hours and was then filtered. The wet cake was washed with 60% aqueous ethanol (185 kg), and transferred back to the reactor. Dichloromethane (213 kg) was added, and the resulting mixture was stirred at 25-30° C. for 2-3 hours and then filtered. The wet cake was washed with dichloromethane (40 kg) and dried under vacuum at 45-50° C. for 40-80 hours to afford crude Compound A (11.7 kg).

The crude Compound A (11.5 kg) and DMSO (250 kg) were added to a 2000 L reactor, and the resulting mixture was stirred at 25-30° C. for 2-4 hours, and then filtered. The wet cake was washed with water (38 kg), and the cake was then transferred back to the reactor. Water (227 kg) was added to the reactor, and the resulting mixture was stirred at 25-30° C. for 30-60 min and then filtered. The wet cake was washed with water (50 kg) and dried under vacuum at 45-50° C. for 30-60 hours to afford Compound A (9.05 kg).

Step 2: Preparation of 2,4-dichloro-6-(6-chloropyridin-2-yl)-1,3,5-triazine (Compound B)

A 250 L reactor was charged with Compound A (8.9 kg, 39.7 mol), benzyltriethylammonium chloride (19.0 kg, 79.4 mol), and $POCl_3$ (37.0 kg, 238.2 mol). The resulting mixture was stirred at 95-105° C. for 18-24 hours, cooled to 30-40° C., and concentrated under reduced pressure to 18-36 L. Ethyl acetate (3×53.0 kg) was added, and the resulting solution was concentrated under reduced pressure to 18-36 L. Additional ethyl acetate (112.0 kg) was added, and the resulting mixture was cooled to 10-20° C.

A 1000 L reactor was charged with $Na_2HPO_4$ (6.6 kg), $NaH_2PO_4 \cdot 2H_2O$ (20.0 kg), and process water (98.0 kg), and the mixture was cooled to 0-15° C. The solution in the 250 L reactor was transferred to the 1000 L reactor. Ethyl acetate (26 kg) was charged to the 250 L reactor and transferred over to the 1000 L reactor. The resulting solution was stirred at 15-25° C. for 2-4 hours and was then allowed to stand for 30-60 min. The layers were separated, and the organic layer was washed three times with aqueous sodium chloride. Ethyl acetate (133.0 kg) was added to the organic layer, and the resulting solution was transferred to a separate reactor through a cartridge filter. The solution was concentrated under reduced pressure to 1-2 volumes, additional ethyl acetate (54.0 kg) was added, and the solution again was concentrated under reduced pressure to 1-2 volumes. N-heptane (2×50.0 kg) was added over 2-3 hours, and the resulting mixture was stirred for 1-2 hours and then concentrated under reduced pressure to 3-5 volumes after each addition of n-heptane. The mixture was then filtered, and the wet cake was added back into the reactor, slurried with n-heptane (40.0 kg), and filtered. The wet cake was dried in the filter at 20-30° C. for 10-15 hours to afford Compound B (9.4 kg).

Step 3: Preparation of 6-(6-chloropyridin-2-yl)-$N^2$, $N^4$-bis((R)-1,1,1-trifluoropropan-2-yl)-1,3,5-triazine-2,4-diamine (Compound 1)

A 300 L reactor was charged with Compound B (7.3 kg, 27.9 mol), (R)-1,1,1-trifluoropropan-2-amine hydrochloride (9.7 kg, 64.2 mol), and N-methyl-2-pyrrolidone (44.4 kg). The reaction mixture was cooled to 10-25° C., and diisopropylethylamine (17.0 kg, 128.4 mol) was added over about 1 hour. The mixture was stirred for about 10 minutes at 10-20° C., for about 1-2 hours at 45-55° C., and for about 20 hours at 95-105° C., and was then cooled to 45-55° C. Process water (4 kg) was added dropwise over about 1 hour, and the resulting solution was transferred to a 500 L reactor, washing with N-methyl-2-pyrrolidone (2 kg). Additional process water (34.0 kg) was added dropwise over about 3 hours at 45-55° C., and the resulting mixture was stirred for about 3.5 hours at 20-30° C. Additional process water (7.4 kg) was added, and the resulting mixture was centrifuged, washing with process water (9 kg). The wet cake was slurried with process water (89 kg), and the resulting slurry was centrifuged, washing with process water (21 kg). The wet cake was transferred back to the 500 L reactor, and acetonitrile (2×133 kg) was added. The resulting solution was concentrated under reduced pressure to 3-5 volumes, and carbon (1.1 kg) and diatomite (6.0 kg) were added. The mixture was filtered, washing with acetonitrile (37 kg), and the filtrate was transferred to a 100 L reactor through a cartridge filter. The solution was concentrated under reduced pressure to 5-5.5 volumes, and purified water (55 kg) was added dropwise over 2-3 hours via a cartridge filter. The mixture was stirred for 2-5 hours at 20-30° C., and additional purified water (4 kg) was added dropwise over 1 hour via the cartridge filter. The mixture was filtered, washing with acetonitrile/water (15 kg, 1:1), and the wet cake was dried for 20-80 hours at 50-60° to afford Compound 1 (8.38 kg).

Example 11

Preparation and Characterization of Citric Acid Cocrystal Type A of Compound 1

A 20 mL vial was charged with 1.02 g of Compound 1 and 508.0 mg of citric acid monohydrate, and acetonitrile (20 mL) was added. The resulting solution was stirred at room temperature (20-25° C.) for 24 hr, during which time a precipitate was formed. The precipitate was collected by filtration through a büchner funnel, and the solids were dried at room temperature for 15.5 hr to afford citric acid cocrystal Type A of Compound 1. The cocrystal was analyzed by XRPD, $^1H$ NMR, DSC, TGA, and DVS analysis.

Figure 6:
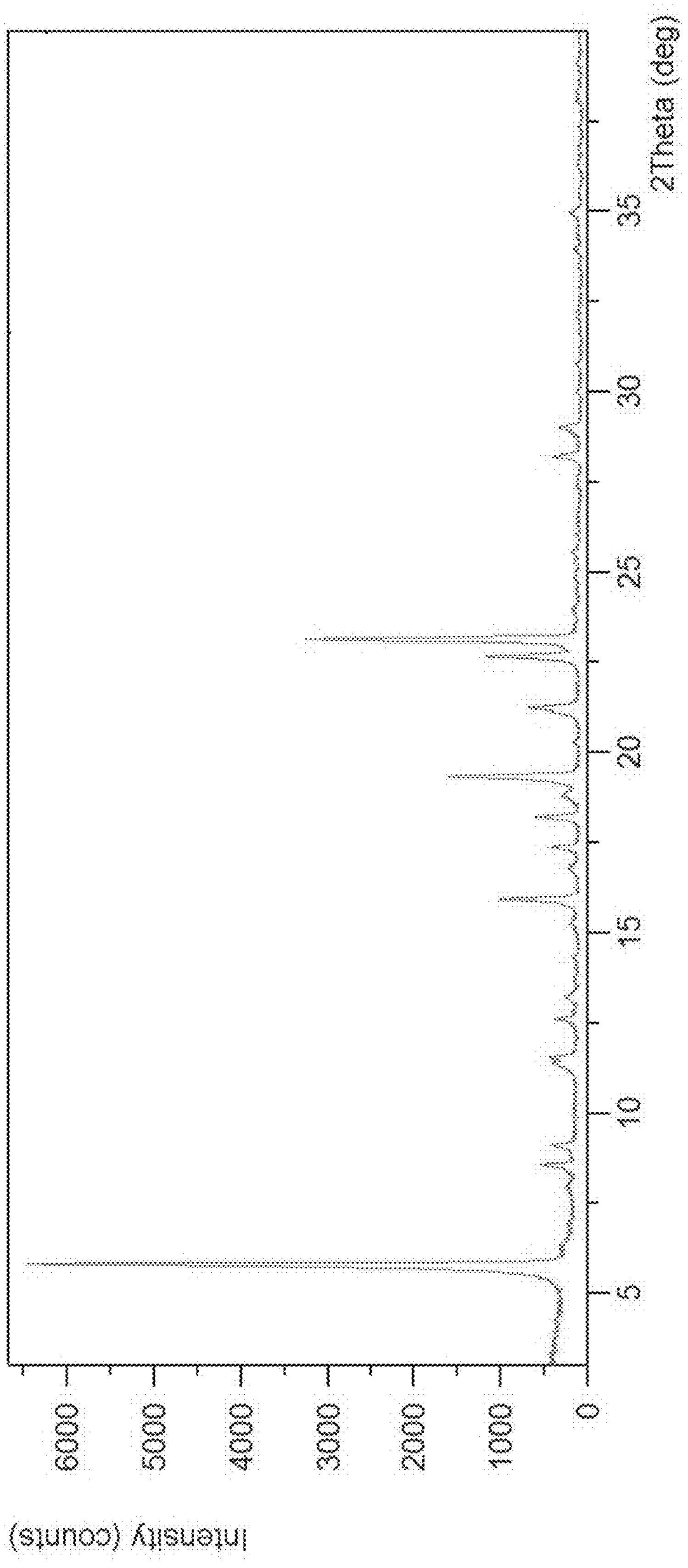
FIG. 6 depicts an X-Ray Powder Diffraction (XRPD) pattern of the Citric Acid Cocrystal Type A of the compound of formula (I), prepared as described in Example 11.

The XRPD pattern of the cocrystal, acquired on a PANalytical Empyrean diffractometer in reflection mode, is shown in FIG. 6. The peak positions, peak heights, and relative intensities of the peaks in the XRPD pattern are listed in Table 7.

TABLE 7

XRPD Peaks of Citric Acid Cocrystal Type A

| Position [°2 Theta] | Height [counts] | Relative Intensity [%] |
|---|---|---|
| 3.3 | 320.80 | 5.09 |
| 5.8 | 6307.39 | 100.00 |
| 8.0 | 147.68 | 2.34 |
| 8.6 | 424.08 | 6.72 |
| 9.1 | 322.42 | 5.11 |
| 11.3 | 289.23 | 4.59 |
| 11.5 | 340.65 | 5.40 |
| 12.6 | 294.33 | 4.67 |
| 13.2 | 169.35 | 2.68 |
| 14.3 | 101.97 | 1.62 |
| 15.2 | 124.86 | 1.98 |
| 15.9 | 923.05 | 14.63 |
| 16.8 | 140.87 | 2.23 |
| 17.4 | 297.53 | 4.72 |
| 18.2 | 531.02 | 8.42 |
| 18.8 | 198.90 | 3.15 |
| 19.3 | 1544.98 | 24.49 |
| 20.2 | 80.24 | 1.27 |

TABLE 7-continued

| XRPD Peaks of Citric Acid Cocrystal Type A | | |
|---|---|---|
| Position [°2 Theta] | Height [counts] | Relative Intensity [%] |
| 21.2 | 609.69 | 9.67 |
| 22.6 | 1088.07 | 17.25 |
| 23.1 | 3138.13 | 49.75 |
| 23.9 | 86.31 | 1.37 |
| 25.3 | 86.80 | 1.38 |
| 25.5 | 95.20 | 1.51 |
| 27.5 | 38.04 | 0.60 |
| 28.2 | 320.14 | 5.08 |
| 29.0 | 248.48 | 3.94 |
| 30.7 | 45.88 | 0.73 |
| 32.0 | 19.96 | 0.32 |
| 34.0 | 72.44 | 1.15 |
| 34.9 | 123.55 | 1.96 |
| 36.2 | 42.49 | 0.67 |
| 38.3 | 75.74 | 1.20 |
| 39.1 | 49.74 | 0.79 |

Figure 7:
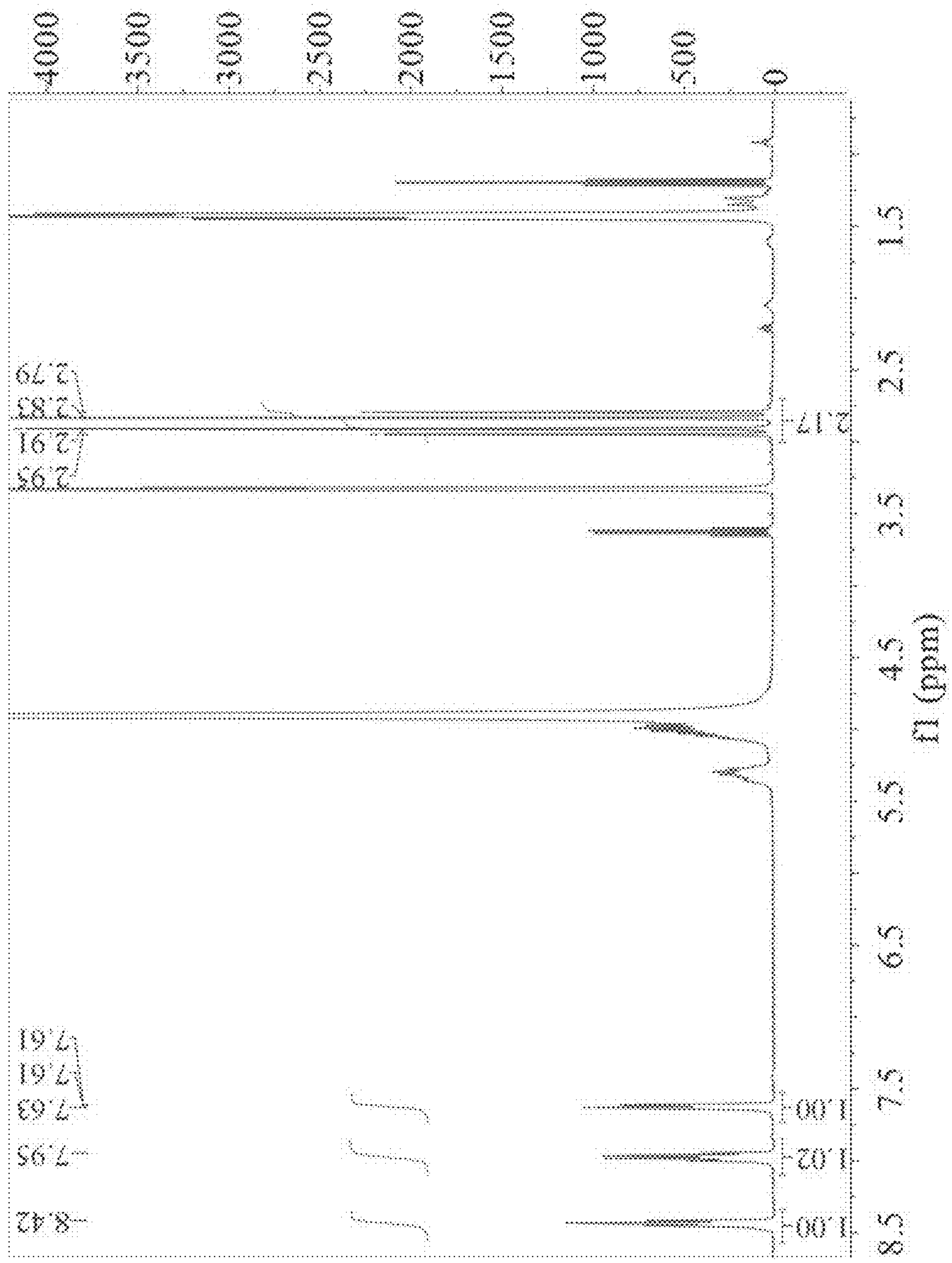
FIG. 7 depicts a $^{1}H$ Nuclear Magnetic Resonance (NMR) spectrum of the Citric Acid Cocrystal Type A of the compound of formula (I), prepared as described in Example 11.

The $^1H$ NMR spectrum of the cocrystal, taken in CD30D, is shown in FIG. 7. The peak integrations of the $^1H$ NMR spectrum revealed a molar ratio of 1:0.5 between Compound 1 and citric acid. Partial $^1H$ NMR (CD30D) δ 8.46-8.42 (m, 1H), 8.00-7.95 (m, 1H), 7.63-7.61 (m, 1H), 2.93 (d, J=16 Hz, 1H), 2.81 (d, J=16 Hz, 1H) ppm.

Figure 8:
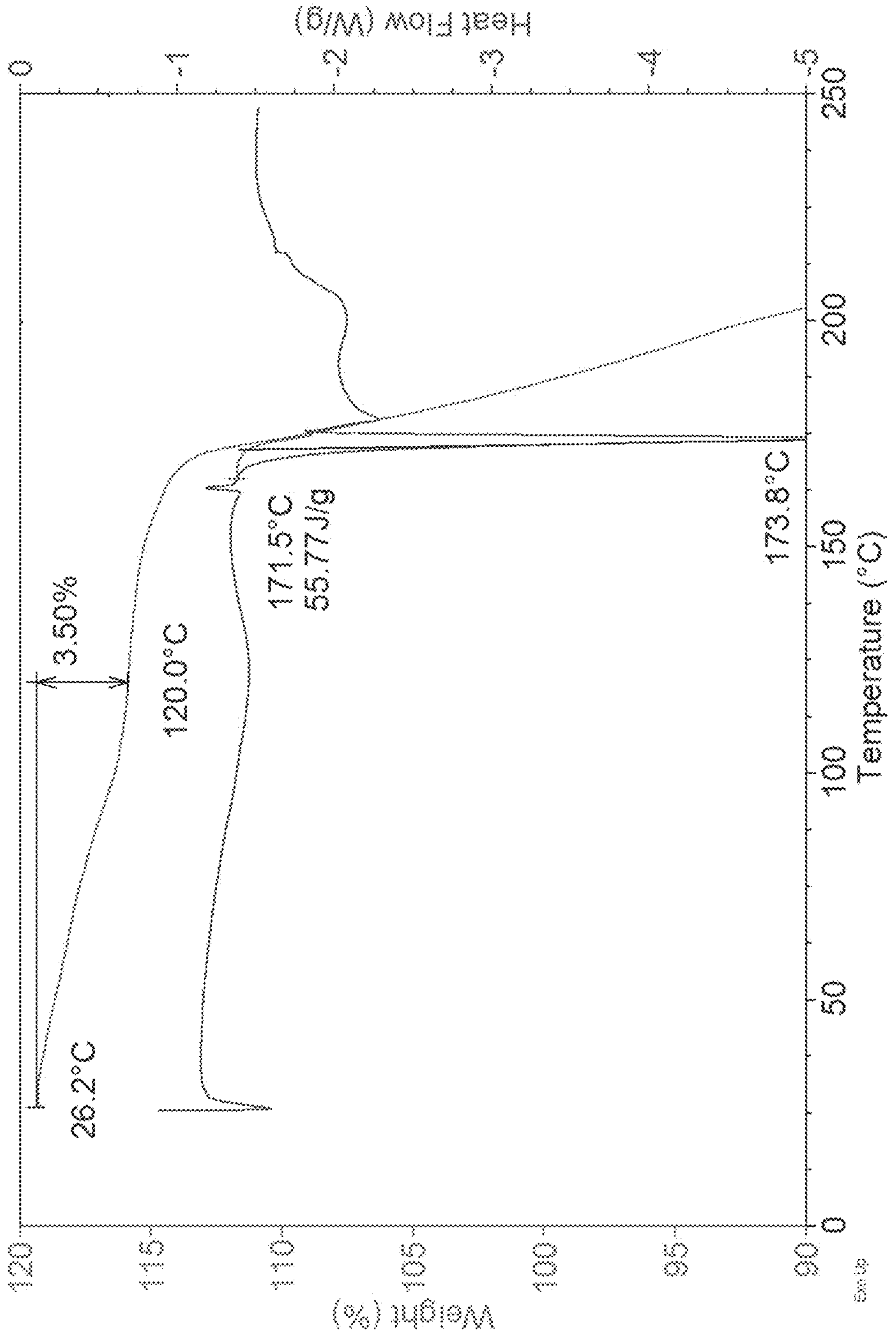
FIG. 8 depicts Differential Scanning Calorimetry (DSC) and Thermogravimetric Analysis (TGA) thermograms of the Citric Acid Cocrystal Type A of the compound of formula (I), prepared as described in Example 11.

The DSC and TGA thermograms of the cocrystal are shown in FIG. 8. DSC analysis was performed with a TA instruments 02000 DSC in crimped Aluminum pan. The temperature and heat flow were calibrated against indium melting. DSC analysis was performed over a temperature range from room temperature to the desired temperature at a ramp rate of 10° C. per minute, with N2 as the purge gas. TGA was conducted at 10° C./min ramping from RT to desired temperature in open Aluminum pan using a TA Instruments Q5000 TGA, with N2 as the purge gas. The DSC thermogram comprises an endothermic peak having an onset temperature of 171.5° C. The TGA thermogram indicates a 3.5% weight loss up to 120° C.

Figure 9:
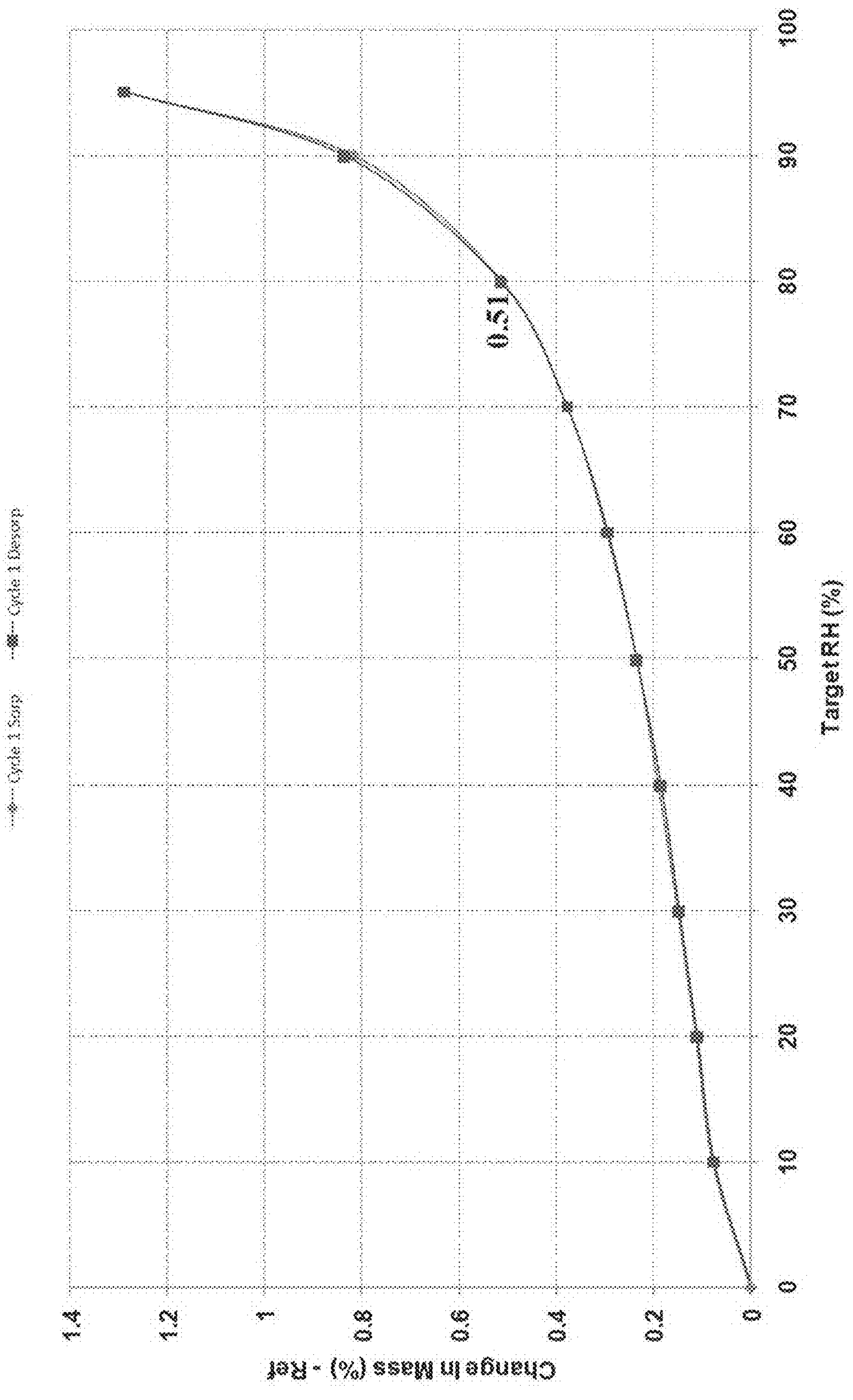
FIG. 9 depicts a Dynamic Vapor Sorption (DVS) isotherm plot of the Citric Acid Cocrystal Type A of the compound of formula (I), prepared as described in Example 11.

The hygroscopicity of the cocrystal was determined by DVS analysis at 25° C., over a range of 0-95% relative humidity. The DVS isotherm plot is shown in FIG. 9 and indicates a 0.5% water uptake at 80% relative humidity, revealing that the citric acid cocyrstal is slightly hygroscopic. XRPD analysis of the material remaining after DVS analysis confirmed that no form change had occurred.

Example 12

Single Crystal X-Ray Diffraction Analysis of Citric Acid Cocrystal Type A of Compound 1

Single crystals of the citric acid cocrystal Type A suitable for structure determination were obtained by slow cooling of a solution of Compound 1 and anhydrous citric acid in n-butanol/heptanes (1/3, v/v). The experiment details were as follows: 12.5 mg of Compound 1 and 6.1 mg of anhydrous citric acid were weighed into a 3 mL vial. 1.2 mL of solvent (n-butanol/heptanes, 1/3 v/v) was added to the vial, and the mixture was equilibrated at 45° C. to form a suspension, which was filtered (0.45 μm PTFE membrane) into two 3-mL vials. Seeds of the citric acid cocrystal Type A were added to the saturated solutions, which were then cooled from 45° C. to 5° C. at the speed of 0.01° C./min (for 4000 min). After five days, needle-like crystals of the citric acid cocrystal Type A were obtained.

X-ray intensity data were collected at 290(2) K using a Bruker D8 ADVANCE diffractometer (Mo Kα radiation, λ=0.71073 Å). Direct methods structure solution, difference Fourier calculations and full-matrix least-squares refinement against F2 were performed with SHELXTL (Sheldrick G M. A short history of SHELX. *Acta Crystallogr A,* 2008, 64:112-122) and OLEX2 (O. V. Dolomanov, L. J. Bourhis, R. J. Gildea, J. A. K. Howard and H. Puschmann. "OLEX2: a complete structure solution, refinement and analysis program". *J. Appl. Cryst.* 2009, 42, 339-341). Molecular graphics were created by Diamond (Brandenburg, K. *DIAMOND,* 1999, Crystal Impact GbR, Bonn, Germany) and Mercury (Macrae, C. F., Edgington, P. R., McCabe, P., Pidcock, E., Shields, G. P., Taylor, R., Towler, M. & van de Streek, J. *J. Appl. Cryst.* 2006, 39, 453-457).

Figure 10:
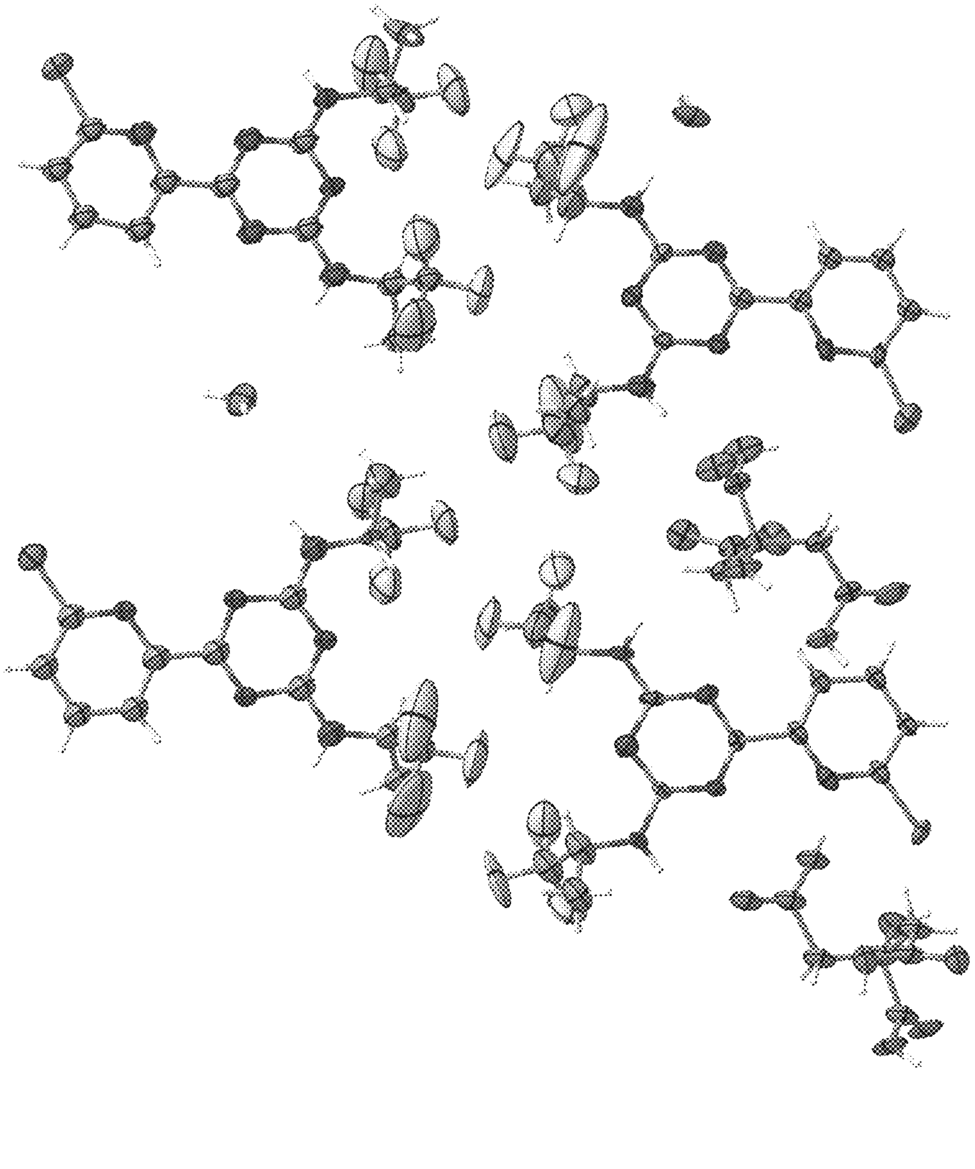
FIG. 10 depicts an Oak Ridge Thermal Ellipsoid Plot (ORTEP) of a single crystal of the Citric Acid Cocrystal Type A of the compound of formula (I), prepared as described in Example 12.
Figure 11:
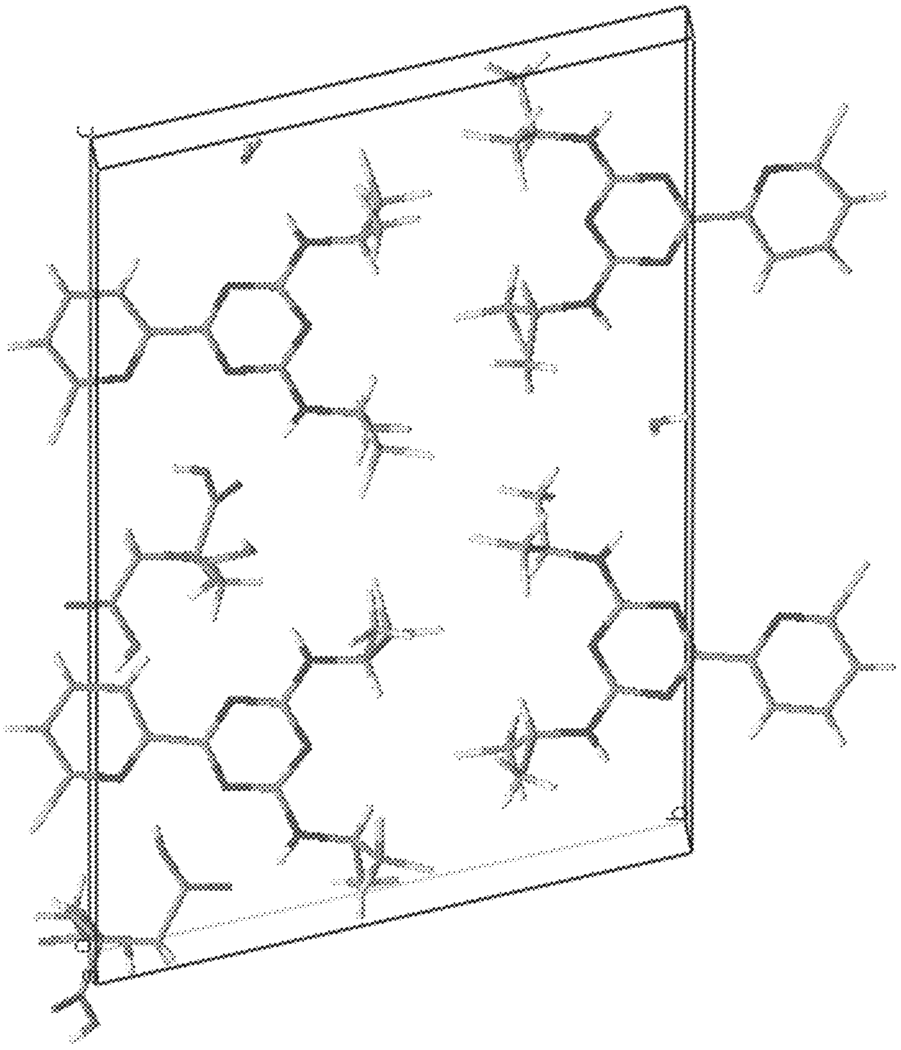
FIG. 11 depicts a unit cell diagram of a single crystal of the Citric Acid Cocrystal Type A of the compound of formula (I), prepared as described in Example 12.

The single crystal structure of the citric acid cocrystal Type A was successfully solved. The crystal data and structure refinement are listed in Table 8. An ORTEP drawing of the crystal structure is shown in FIG. 10, and the unit cell is shown in FIG. 11. In the crystal structure, the molar ratio of Compound 1:citric acid:H2O is 2:1:1. There are four molecules of Compound 1, two citric acid molecules and two water molecules per unit cell.

TABLE 8

| Crystal Data and Structure Refinement for Citric Acid Cocrystal Type A Single Crystal | | |
|---|---|---|
| Identification code | CP8338A | |
| Empirical formula | $C_{34}H_{36}Cl_2F_{12}N_{12}O_8$ | |
| Formula weight | 1039.65 | |
| Temperature | 290(2) K | |
| Wavelength | 0.71073 Å | |
| Crystal system, space group | Triclinic | P1 |
| Unit cell dimensions | a = 6.8548(10) Å | α = 76.223(4) deg. |
| | b = 16.148(2) Å | β = 89.131(4) deg. |
| | c = 21.388(3) Å | γ = 79.087(4) deg. |
| Volume | 2256.7(6) $Å^3$ | |
| Z, Calculated density | 2 | 1.530 $Mg/m^3$ |
| Absorption coefficient | 0.255 $mm^{-1}$ | |
| F(000) | 1060 | |
| Crystal size | 0.23 × 0.16 × 0.13 $mm^3$ | |
| Theta range for data collection | 2.59-25.06 deg. | |
| Limiting indices | $-8 \leq h \leq 8$<br>$-19 \leq s \leq 19$<br>$-25 \leq 1 \leq 25$ | |
| Reflections collected/unique | 46324/14971 [R(int) = 0.0442] | |
| Completeness | 97.9% | |
| Refinement method | Full-matrix least-squares on $F^2$ | |
| Data/restraints/parameters | 14971/52/881 | |
| Goodness-of-fit on $F^2$ | 1.153 | |
| Final R indices [I > 2sigma(I)] | $R_1$ = 0.1214 | $wR_2$ = 0.2825 |
| Largest diff. peak and hole | 0.845 and −0.834 e · $Å^{-3}$ | |
| Absolute structure parameter | 0.40(14) | |

Example 13

Preparation and Characterization of Maleic Acid Cocrystal Type A of Compound 1

Compound 1 (100.4 mg) and maleic acid (28.3 mg) were dissolved in acetone (2.0 mL), and the resulting solution was stirred at room temperature for one day, during which time a precipitate was formed. The precipitate was isolated and air dried at room temperature to afford maleic acid cocrystal Type A of Compound 1. The cocrystal was analyzed by XRPD, $^1H$ NMR, DSC, TGA, and DVS analysis.

Figure 12:
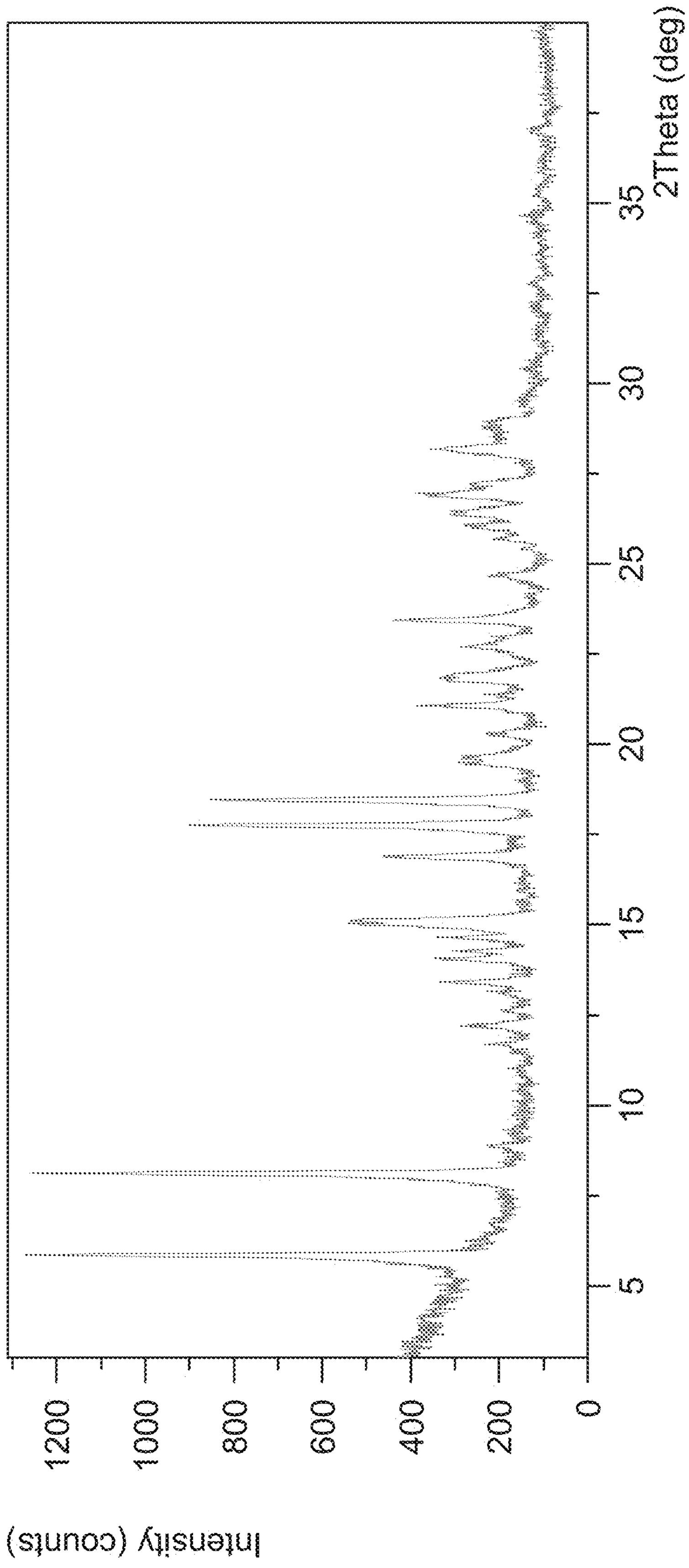
FIG. 12 depicts an X-Ray Powder Diffraction (XRPD) pattern of the Maleic Acid Cocrystal Type A of the compound of formula (I), prepared as described in Example 13.

The XRPD pattern of the cocrystal, acquired on a PANalytical Empyrean diffractometer in reflection mode, is shown in FIG. 12. The peak positions, peak heights, and relative intensities of the peaks in the XRPD pattern are listed in Table 9.

TABLE 9

XRPD Peaks of Maleic Acid Cocrystal Type A

| Position [°2 Theta] | Height [counts] | Relative Intensity [%] |
|---|---|---|
| 5.9 | 1016.70 | 96.62 |
| 8.1 | 1052.24 | 100.00 |
| 8.8 | 50.23 | 4.77 |
| 12.2 | 128.67 | 12.23 |
| 13.4 | 177.56 | 16.87 |
| 14.1 | 187.79 | 17.85 |
| 14.6 | 145.97 | 13.87 |
| 15.0 | 365.04 | 34.69 |
| 15.2 | 384.90 | 36.58 |
| 16.9 | 314.16 | 29.86 |
| 17.8 | 750.78 | 71.35 |
| 18.5 | 694.00 | 65.96 |
| 19.5 | 136.27 | 12.95 |
| 20.3 | 85.97 | 8.17 |
| 21.1 | 228.41 | 21.71 |
| 21.8 | 191.44 | 18.19 |
| 22.7 | 145.37 | 13.82 |
| 23.4 | 294.84 | 28.02 |
| 24.7 | 89.70 | 8.52 |
| 26.1 | 146.52 | 13.93 |
| 26.4 | 180.26 | 17.13 |
| 26.9 | 230.07 | 21.87 |
| 28.2 | 218.34 | 20.75 |
| 29.0 | 98.38 | 9.35 |
| 36.9 | 26.92 | 2.56 |

Figure 13:
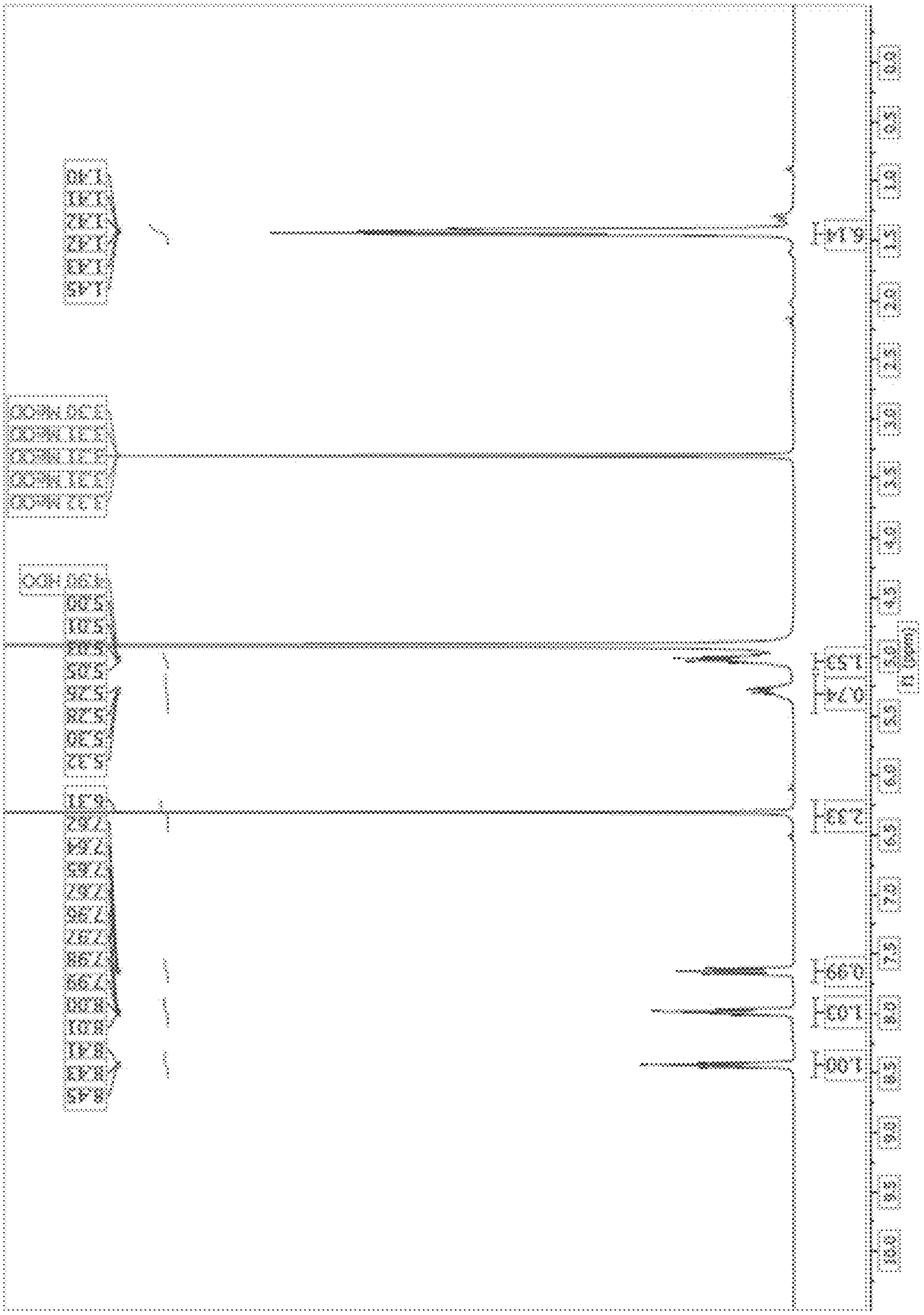
FIG. 13 depicts a $^{1}H$ Nuclear Magnetic Resonance (NMR) spectrum of the Maleic Acid Cocrystal Type A of the compound of formula (I), prepared as described in Example 13.

The $^1H$ NMR spectrum of the cocrystal, taken in $CD_3OD$, is shown in FIG. 13. The peak integrations of the $^1H$ NMR spectrum revealed a molar ratio of about 1:1.1 between Compound 1 and maleic acid, suggesting that the ratio of Compound 1 to maleic acid in the cocrystal is 1:1. Partial $^1H$ NMR ($CD_3OD$) δ 8.45-8.41 (m, 1H), 8.01-7.96 (m, 1H), 7.67-7.62 (m, 1H), 6.31 (s, 2H).

Figure 14:
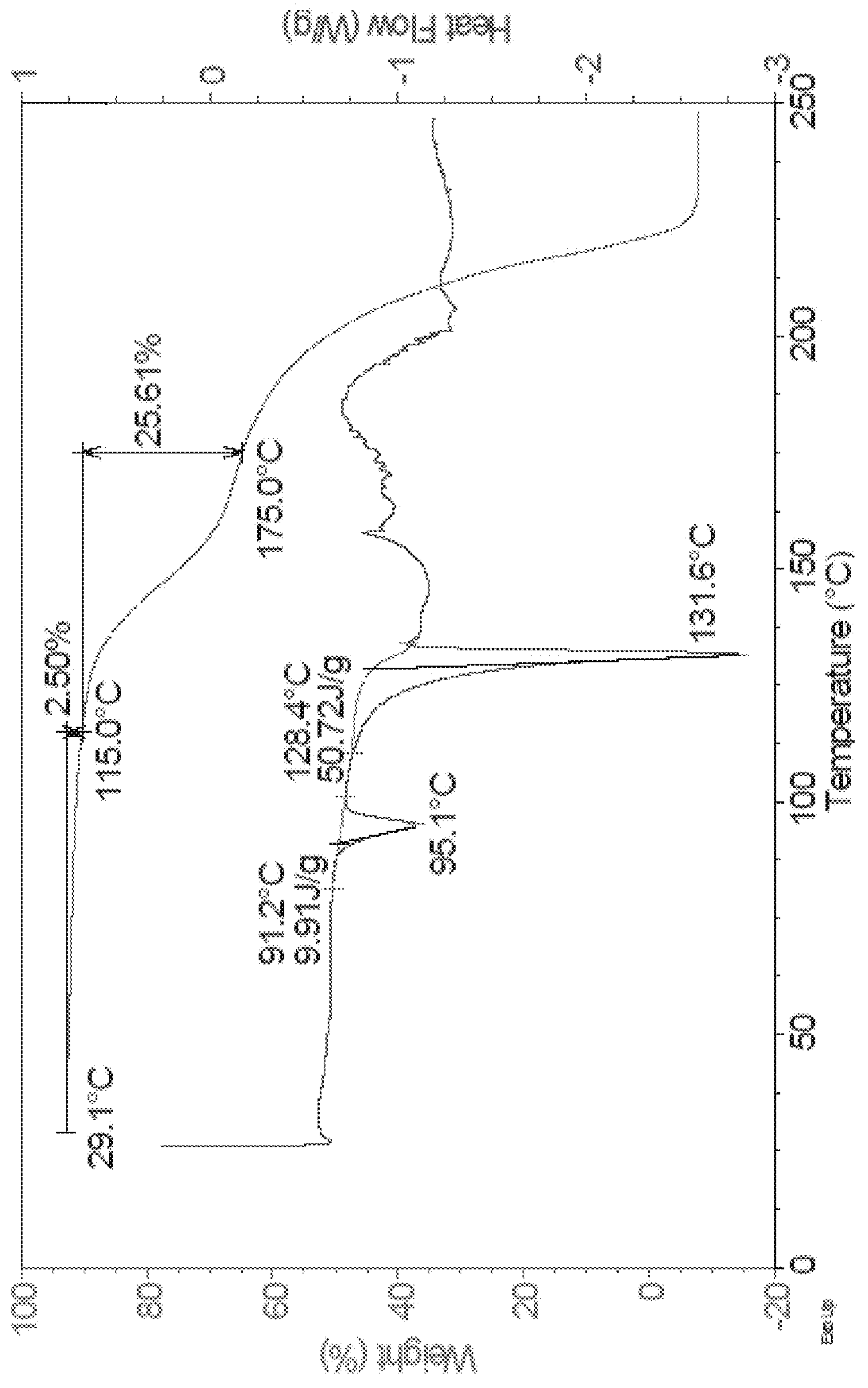
FIG. 14 depicts Differential Scanning Calorimetry (DSC) and Thermogravimetric Analysis (TGA) thermograms of the Maleic Acid Cocrystal Type A of the compound of formula (I), prepared as described in Example 13.

The DSC and TGA thermograms of the cocrystal are shown in FIG. 14. DSC analysis was performed with a TA instruments 02000 DSC in crimped Aluminum pan. The temperature and heat flow were calibrated against indium melting. DSC analysis was performed over a temperature range from room temperature to the desired temperature and a ramp rate of 10° C. per minute, with $N_2$ as the purge gas. TGA was conducted at 10° C./min ramping from RT to desired temperature in open Aluminum pan using a TA Instruments Q5000 TGA, with N2 as the purge gas. The DSC thermogram comprises two endothermic peaks having onset temperatures of 91.2° C. and 128.4° C. The TGA thermogram indicates a 2.5% weight loss up to 115° C.

Figure 15:
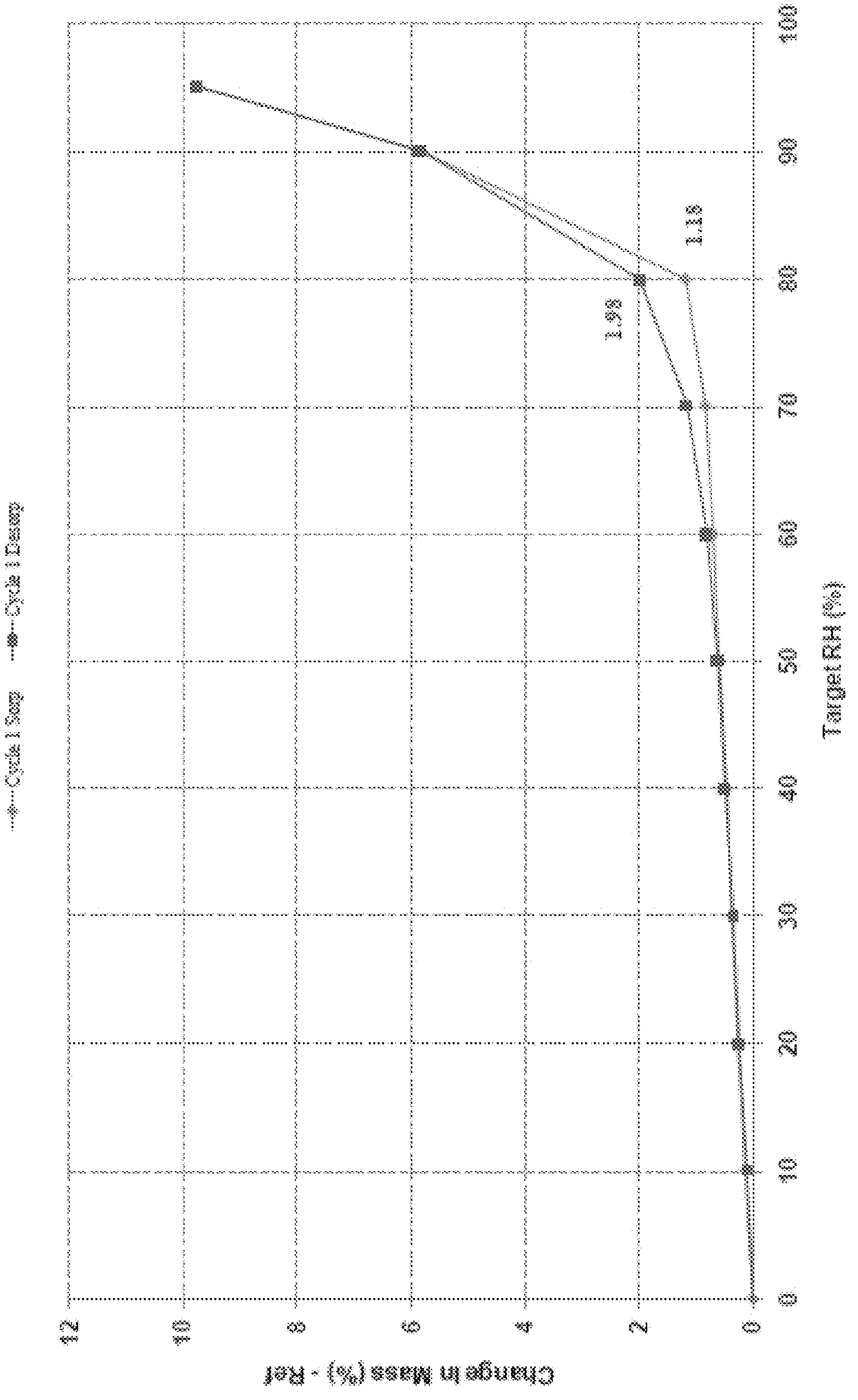
FIG. 15 depicts a Dynamic Vapor Sorption (DVS) isotherm plot of the Maleic Acid Cocrystal Type A of the compound of formula (I), prepared as described in Example 13.

The hygroscopicity of the cocrystal was determined by DVS analysis at 25° C., over a range of 0-95% relative humidity. The DVS isotherm plot is shown in FIG. 15 and indicates a 2.0% water uptake at 80% relative humidity, revealing that the maleic acid cocrystal is slightly hygroscopic. XRPD analysis of the material remaining after DVS analysis confirmed that no form change had occurred.

Example 14

Preparation and Characterization of Citric Acid Cocrystal Type A of Compound 1

A 100 L reactor was charged with 1.5 kg (7.9 mol) of anhydrous citric acid and 31.0 kg of acetone. The mixture was agitated at 20-30° C. until the citric acid dissolved completely (~30-90 min), and the resulting solution was transferred to a 500 L reactor. The 100 L reactor was washed with an additional 5.0 kg of acetone, which was then added to the 500 L reactor. Compound 1 (6.73 kg, 16.2 mol), prepared as described in Example 10, was added to the reactor, and the mixture was agitated at 20-30° C. until Compound 1 had dissolved completely (~1 h). After stirring for an additional 1-2 hours at 20-30° C., 75.0 g of purified water was added to the reactor. N-heptane (13.0 kg) was added to the reactor over a period of 1 hour, and then seed crystals of the citric acid cocrystal Type A (46 g) were added. The mixture was stirred for 1-2 hours at 20-30° C., and then additional n-heptane (104.0 kg) was added over a period of 2-4 hours.

The resulting mixture was stirred for an additional 2-3 hours at 20-30° C., and then the reactor was cooled to 10-20° C. The mixture was wet milled (7900 rpm) at 10-20° C. The mixture was filtered, and the filter cake was washed with 7 kg of an acetone/n-heptane solution (7 volumes/25 volumes) and then dried for 10-20 hours at ≤30° C. to afford 7.15 kg of the citric acid cocrystal Type A. The isolated cocrystal was characterized by elemental analysis, $^1H$ NMR analysis, $^{13}C$ NMR analysis, FTIR analysis, UV/visible spectroscopy, XRPD analysis, DSC analysis, TGA analysis, and HPLC analysis.

The results of elemental analysis of the cocrystal are reported in Table 10. The measured elemental composition is consistent with the theoretical composition as determined from the chemical formula $C_{34}H_3Cl_2F_{12}N_{12}O_8$, based on a 2:1:1 molar ratio of Compound 1:citric acid:$H_2O$.

TABLE 10

Elemental Analysis of Citric Acid Cocrystal Type A

| Element | Theoretical | Observed |
|---|---|---|
| Carbon | 39.28% | 39.10% |
| Hydrogen | 3.49% | 3.54% |
| Nitrogen | 16.17% | 15.64% |

Figure 16:
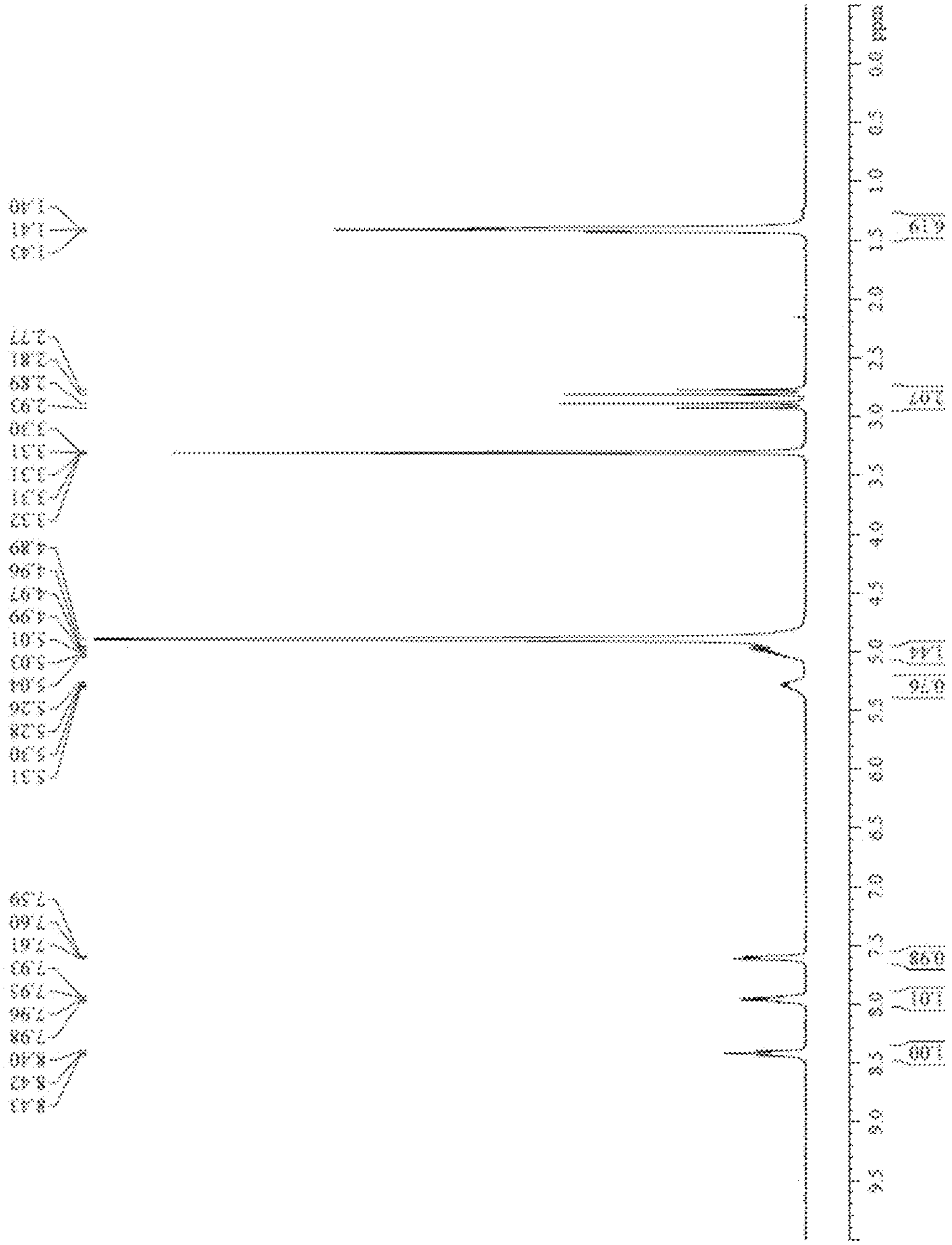
FIG. 16 depicts a $^{1}H$ NMR spectrum of the Citric Acid Cocrystal Type A of the compound of formula (I), prepared as described in Example 14.
Figure 17:
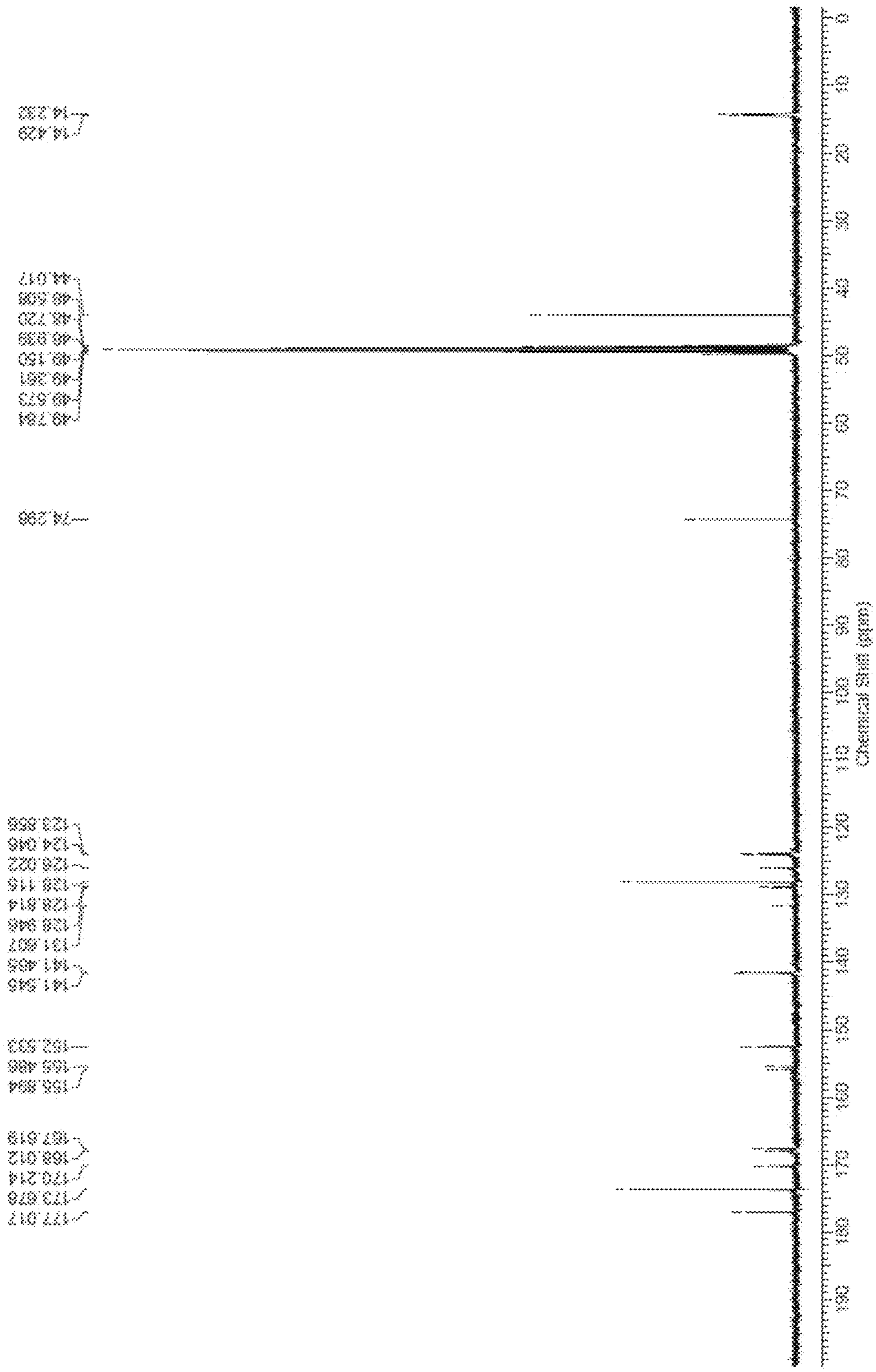
FIG. 17 depicts a $^{13}C$ NMR spectrum of the Citric Acid Cocrystal Type A of the compound of formula (I), prepared as described in Example 14.

The $^1H$ and $^{13}C$ NMR spectra of the cocrystal, taken in $CD_3OD$, are shown in FIGS. 16 and 17, respectively. The peak integrations of the $^1H$ NMR spectrum revealed a molar ratio of 1:0.5 between Compound 1 and citric acid. Partial $^1H$ NMR ($CD_3OD$) δ 8.43-8.40 (m, 1H), 7.98-7.93 (m, 1H), 7.61-7.59 (m, 1H), 2.91 (d, J=16 Hz, 1H), 2.79 (d, J=16 Hz, 1H) ppm.

Figure 18:
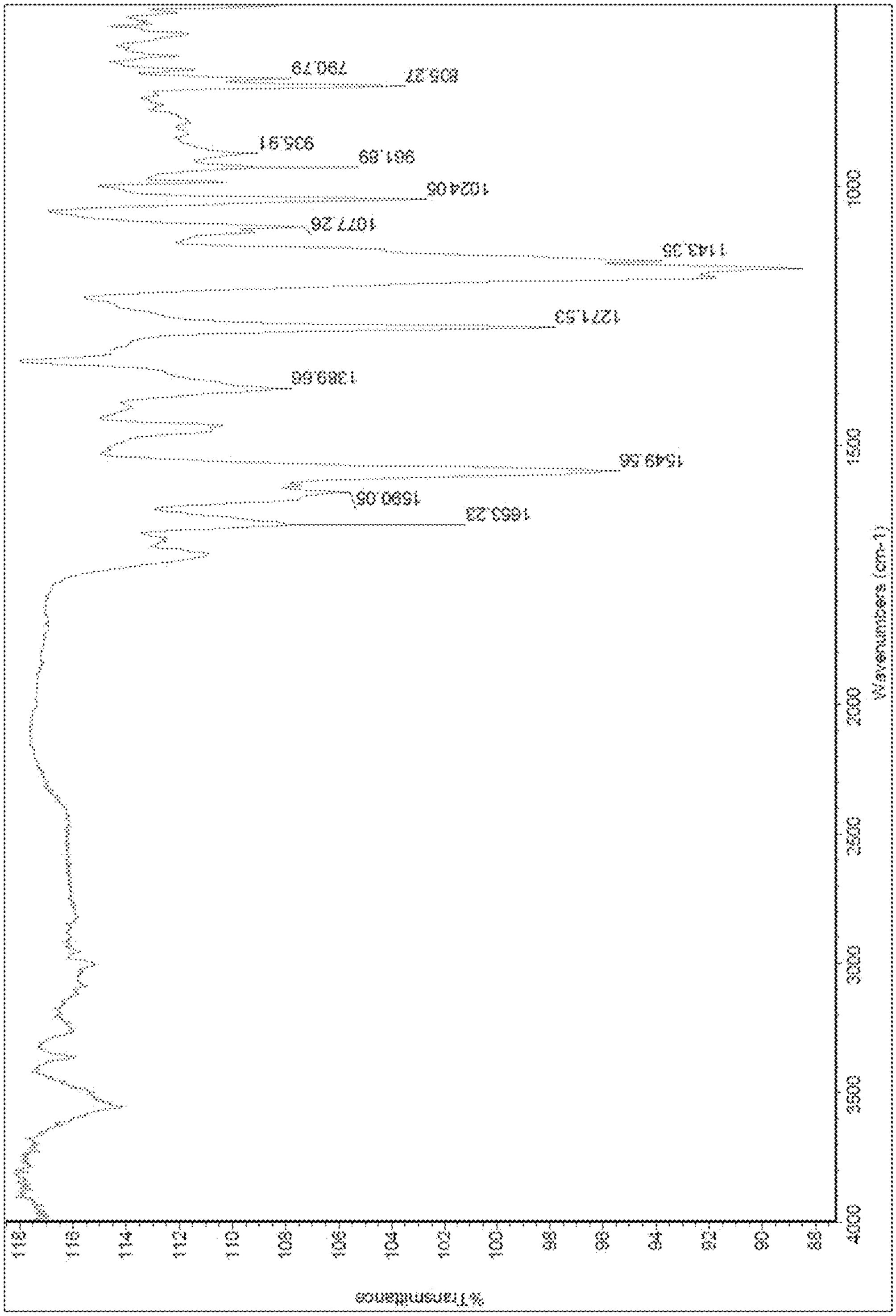
FIG. 18 depicts a Fourier Transform Infrared (FTIR) spectrum of the Citric Acid Cocrystal Type A of the compound of formula (I), prepared as described in Example 14.

The FTIR spectrum of the cocrystal, obtained on a Nicolet IS FTIR Spectrometer, is shown in FIG. 18. The FTIR spectrum was obtained on the solid material using an attenuated total reflection accessory. The spectrum included bands at 1653, 1590, 1549, 1271, and 1143 $cm^{-1}$.

The UV/visible spectrum of the cocrystal, acquired on an Agilent 8453 spectrophotometer at a concentration of 5.2 μg/mL in acetonitrile, is shown in FIG. 19. The spectrum has absorption bands with maxima at 204 nm, 216 nm, and 281 nm.

Figure 20:
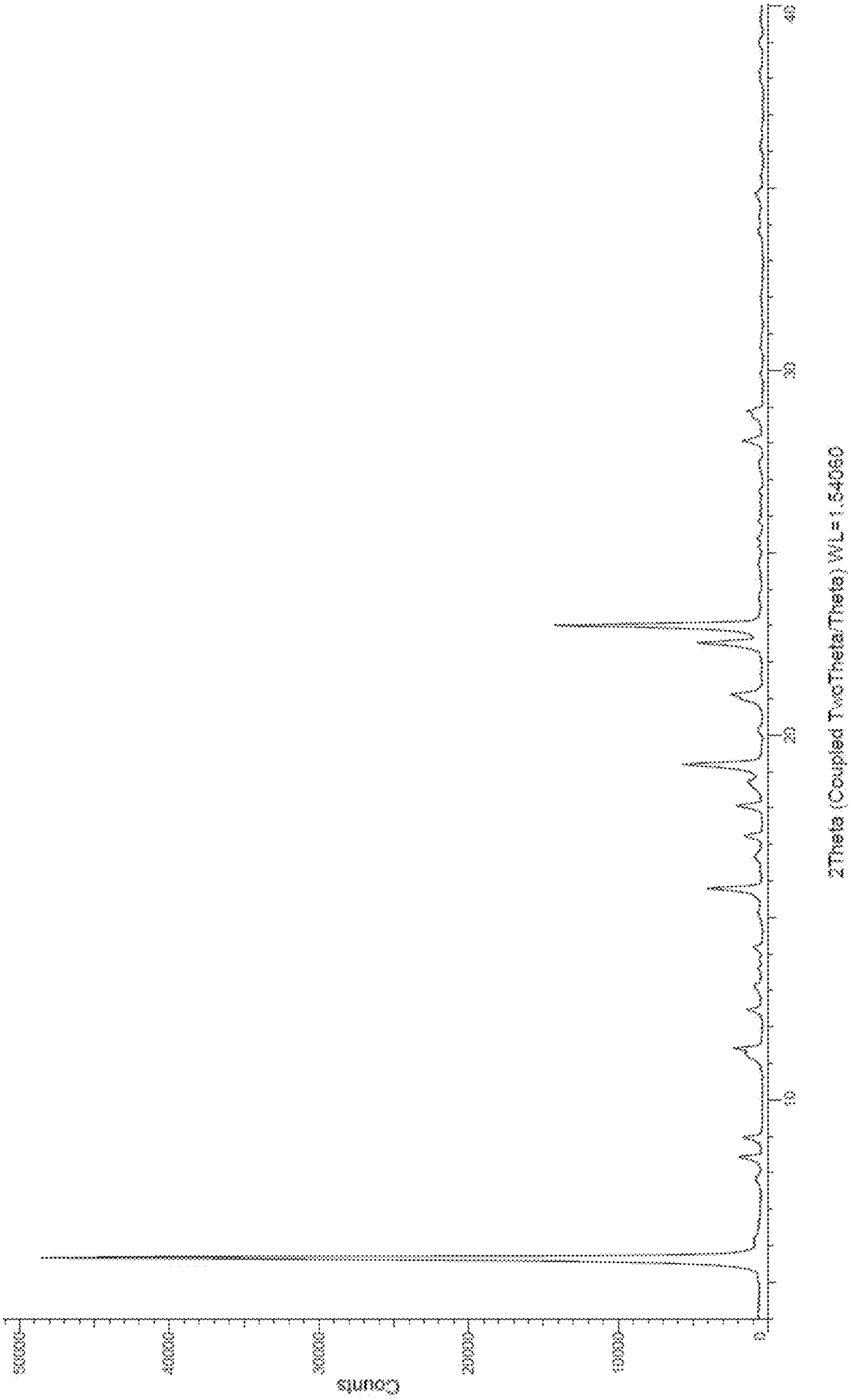
FIG. 20 depicts an XRPD pattern of the Citric Acid Cocrystal Type A of the compound of formula (I), prepared as described in Example 14.

The XRPD pattern of the cocrystal, acquired at room temperature in reflection mode on a Bruker 08 Advance diffractometer, is shown in FIG. 20. The peak positions, peak heights, and relative intensities of the peaks in the XRPD pattern are listed in Table 11.

TABLE 11

XRPD Peaks of Citric Acid Cocrystal Type A

| Position [°2 Theta] | Height [counts] | Relative Intensity [%] |
|---|---|---|
| 5.7 | 41917 | 100.0 |
| 6.1 | 355 | 0.8 |
| 7.8 | 323 | 0.8 |
| 8.4 | 1348 | 3.2 |
| 9.0 | 1084 | 2.6 |
| 11.3 | 1059 | 2.5 |
| 11.4 | 1144 | 2.7 |
| 12.5 | 983 | 2.3 |
| 13.1 | 477 | 1.1 |
| 13.6 | 249 | 0.6 |
| 13.8 | 173 | 0.4 |
| 14.2 | 579 | 1.4 |
| 15.1 | 317 | 0.8 |
| 15.8 | 3288 | 7.8 |
| 16.3 | 90.6 | 0.2 |
| 16.7 | 441 | 1.1 |
| 17.2 | 1104 | 2.6 |
| 18.1 | 1502 | 3.6 |
| 18.7 | 866 | 2.1 |
| 19.2 | 4667 | 11.1 |
| 20.1 | 300 | 0.7 |
| 21.1 | 1689 | 4.0 |
| 21.7 | 97.3 | 0.2 |
| 22.5 | 4164 | 9.9 |
| 23.0 | 12972 | 30.9 |
| 23.8 | 174 | 0.4 |
| 24.7 | 212 | 0.5 |
| 24.7 | 173 | 0.4 |
| 25.2 | 140 | 0.3 |
| 25.4 | 308 | 0.7 |
| 25.9 | 242 | 0.6 |
| 26.4 | 159 | 0.4 |
| 26.7 | 223 | 0.5 |
| 27.4 | 217 | 0.5 |
| 28.1 | 1306 | 3.1 |
| 28.8 | 777 | 1.9 |
| 29.9 | 164 | 0.4 |
| 30.6 | 190 | 0.5 |
| 30.9 | 74.2 | 0.2 |
| 31.5 | 66.7 | 0.2 |
| 32.0 | 89.3 | 0.2 |
| 33.8 | 250 | 0.6 |
| 34.2 | 203 | 0.5 |
| 34.8 | 423 | 1.0 |
| 35.3 | 96.6 | 0.2 |
| 36.2 | 216 | 0.5 |
| 36.6 | 107 | 0.3 |
| 37.2 | 53.6 | 0.1 |
| 38.0 | 145 | 0.3 |
| 38.1 | 212 | 0.5 |
| 39.0 | 242 | 0.6 |
| 39.6 | 89.9 | 0.2 |

Figure 21:
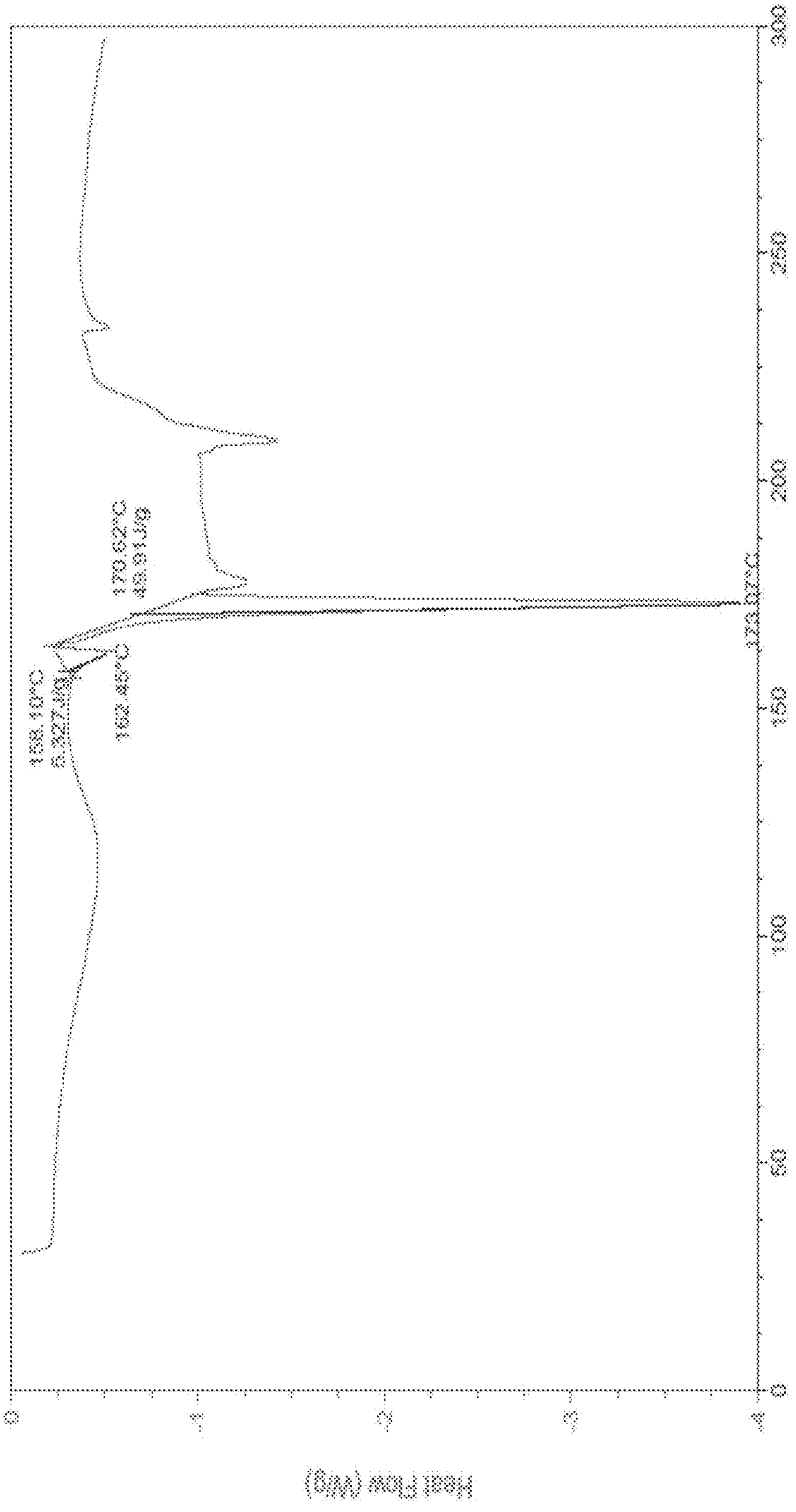
FIG. 21 depicts a DSC thermogram of the Citric Acid Cocrystal Type A of the compound of formula (I), prepared as described in Example 14.

The DSC thermogram of the cocrystal is shown in FIG. 21. DSC analysis was performed on a TA 020 DSC instrument, with a ramp rate of 10.0° C./minute and using N2 as the purge gas. The thermogram comprises an endothermic peak having an onset temperature of 170.6° C. and a peak temperature of 173.0° C.

The TGA curve of the cocrystal is shown in FIG. 22. TGA was performed on a TA Q5000 IR TGA system at a ramp rate of 10° C./minute and using N2 as the purge gas. The cocrystal exhibited a 1.692% weight loss up to 136.06° C. Rapid weight loss was observed above approximately 165° C., which is believed to result from decomposition.

The purity profile of the cocrystal was determined by HPLC analysis (Method 1). The concentrations (w/w %) of Compounds 2-7 and total impurities are reported in Table 12. The concentrations (w/w %) were determined by HPLC peak area, based on the assumption that Compounds 1-7 have a relative response factor of 1. The concentration (w/w %) of each compound reported in Table 12 reflects the HPLC peak area attributed to the compound, as a percentage of the total peak area attributable to Compounds 1 and any organic impurities. The concentration (w/w %) of total impurities reported in Table 12 reflects the total HPLC peak area attributed to organic impurities (Compounds 2-7), as a percentage of the total peak area attributable to Compound 1 and any organic impurities. The stereoisomers of Compound 1 (Compounds 8 and 9) co-elute with Compound 1 under the conditions of HPLC Method 1 and therefore are not included in the concentration of total impurities.

TABLE 12

Batch Analysis of Citric Acid Cocrystal by HPLC Method 1

| Compound | Result (w/w %) |
|---|---|
| Compound 3 | Not Detected |
| Compound 4 | <0.05% |
| Compound 6 | <0.05% |
| Compound 5 | 0.12% |
| Compound 7 | <0.05% |
| Compound 2 | <0.05% |
| Total Impurities | 0.12% |

The stereochemical purity of the cocrystal was determined by HPLC analysis (Method 2). The concentrations (w/w %) of Compounds 8 and 9 are reported in Table 13. The concentrations (w/w %) were determined by HPLC peak area, based on the assumption that Compounds 1, 8, and 9 have a relative response factor of 1. The concentrations (w/w %) of Compounds 8 and 9 reported in Table 13 reflect the HPLC peak area attributed to the compound, as a percentage of the total peak area attributable to Compounds 1, 8, and 9.

TABLE 13

Batch Analysis of Citric Acid Cocrystal by HPLC Method 2

| Compound | Result (w/w %) |
|---|---|
| Compound 8 | 0.33% |
| Compound 9 | <0.05% |

Example 15

Preparation of Citric Acid Cocrystal Type A of Compound 1

A 30 L reactor (Reactor 1) was charged with 1.2 kg of Compound 1 (2.9 mol) and 1.87 kg of acetone, and the resulting mixture was stirred for 0.5 hours at 25-28° C. A second reactor (Reactor 2) was charged with 297.9 g of citric acid monohydrate (1.42 mol) and 674 g of acetone, and the resulting mixture was stirred for 0.5 hours at 25-28° C. Half of the contents of Reactor 2 were transferred to Reactor 1 at 37-43° C., and then seed crystals of citric acid cocrystal Type A (6 g) were added to Reactor 1. The resulting mixture in Reactor 1 was stirred for 1.5 hours at 37-43° C. The remaining contents of Reactor 2 were transferred to Reactor 1 over a period of 0.5-1.5 hours at 37-43° C., and then n-heptane (6690 g) were added to Reactor 1 over a period of 2.5 hours at 37-43° C. Reactor 1 was cooled to 8-12° C. over a period of 2.5 hours, and stirring was continued for 1-3 hours at 8-12° C.

The reaction mixture in Reactor 1 was then filtered under nitrogen gas, and the filter cake was washed with 2800 mL of an acetone/n-heptane solution (1/3 v/v). The filter cake was dried under vacuum for 16-48 hours at 25-30° C. to afford 1430 g of the citric acid cocrystal Type A as a white solid.

Example 16

Preparation and Characterization of Free Form Type A of Compound 1

Compound 1 (450.0 g), prepared as described in Example 10, was dissolved in 1.0 L of ethyl acetate at 70-80° C. 4.0 L of n-heptane was added drop wise into the solution at 70-80° C. over 2 h. The mixture was cooled to 0-10° C. over 3 h and was then stirred for 16 h at 0-10° C. The resulting suspension was filtered, and the wet cake was dried at 40-45° C. for 16 h to afford a 400 g dry cake of the crystalline free form Type A. The isolated crystalline material was characterized by elemental analysis XRPD analysis, DSC analysis, TGA analysis, and HPLC analysis.

The results of elemental analysis are reported in Table 14. The measured elemental composition is consistent with the theoretical composition as determined from the chemical formula $C_{14}H_{13}ClF_6N_6$.

TABLE 14

Elemental Analysis of Free Form Type A

| Element | Observed |
|---|---|
| Carbon | 40.42 |
| Hydrogen | 3.322 |
| Nitrogen | 19.70 |

Figure 23:
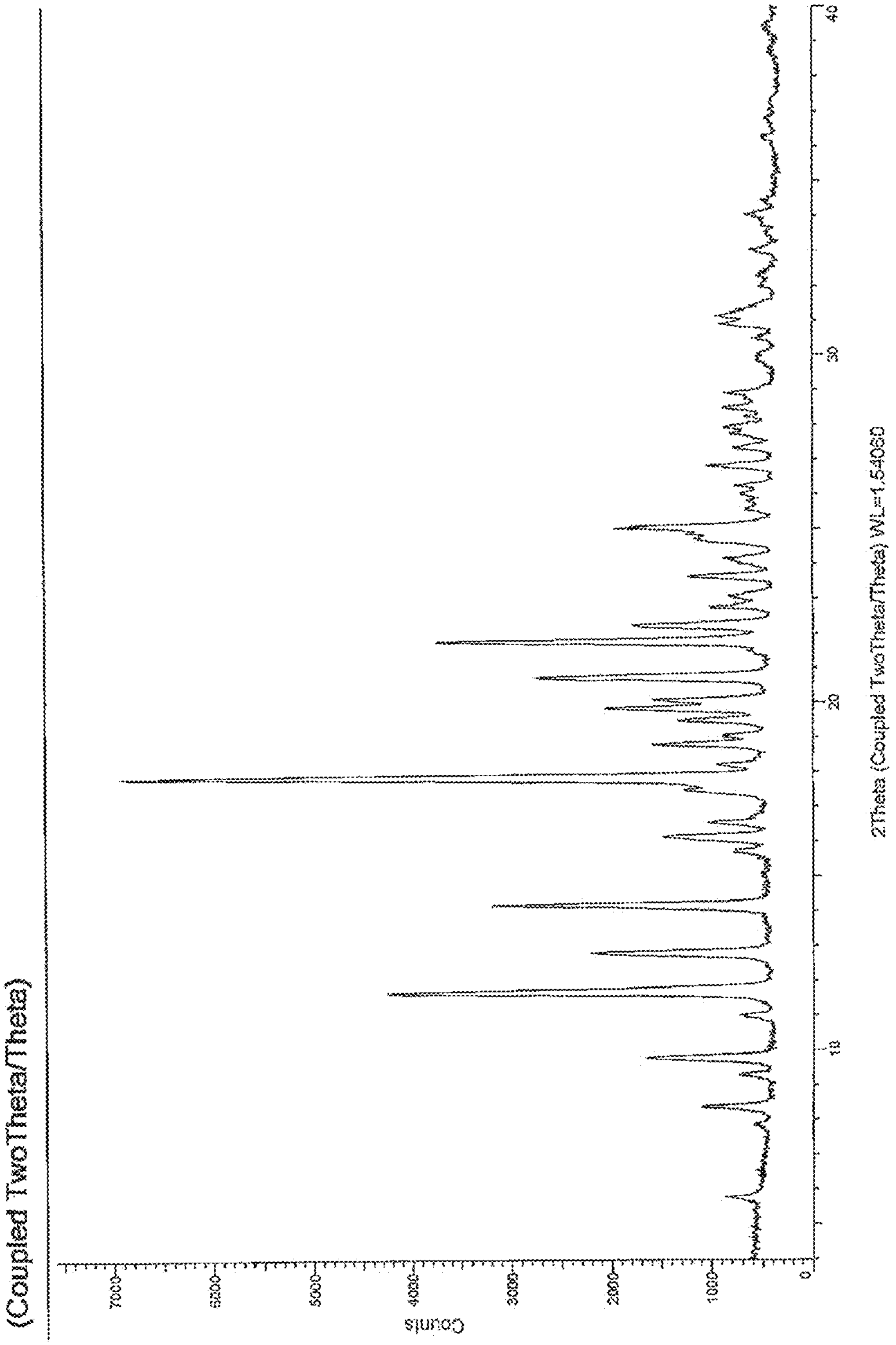
FIG. 23 depicts an XRPD pattern of the Free Form Type A of the compound of formula (I), prepared as described in Example 17.

The XRPD pattern of free form type A, acquired at room temperature in reflection mode on a Bruker 08 Advance diffractometer, is shown in FIG. 23. The peak positions, peak heights, and relative intensities of the peaks in the XRPD pattern are listed in Table 15.

TABLE 15

XRPD Peaks of Free Form Type A

| Position [°2 Theta] | Height [counts] | Relative Intensity [%] |
|---|---|---|
| 5.8 | 268 | 4.2 |
| 7.8 | 124 | 2.0 |
| 8.4 | 642 | 10.1 |
| 9.3 | 298 | 4.7 |
| 9.8 | 1213 | 19.1 |
| 11.0 | 247 | 3.9 |
| 11.7 | 3674 | 58.0 |
| 12.8 | 1736 | 27.4 |
| 14.2 | 2609 | 41.2 |
| 15.7 | 309 | 4.9 |
| 16.1 | 943 | 14.9 |
| 16.5 | 538 | 8.5 |
| 17.5 | 609 | 9.6 |
| 17.8 | 6336 | 100.0 |
| 18.2 | 379 | 6.0 |
| 18.8 | 1056 | 16.7 |
| 19.0 | 325 | 5.1 |
| 19.5 | 817 | 12.9 |
| 19.8 | 1553 | 24.5 |
| 20.0 | 926 | 14.6 |
| 20.7 | 2288 | 36.1 |
| 21.8 | 3273 | 51.7 |
| 22.2 | 1281 | 20.2 |
| 22.8 | 500 | 7.9 |
| 23.1 | 381 | 6.0 |
| 23.6 | 804 | 12.7 |
| 24.1 | 337 | 5.3 |
| 24.7 | 707 | 11.2 |
| 25.0 | 1517 | 23.9 |
| 25.6 | 209 | 3.3 |
| 26.0 | 282 | 4.4 |
| 26.2 | 243 | 3.8 |
| 26.8 | 592 | 9.3 |
| 27.4 | 305 | 4.8 |
| 27.8 | 290 | 4.6 |
| 27.9 | 383 | 6.0 |
| 28.2 | 249 | 3.9 |
| 28.5 | 455 | 7.2 |
| 28.9 | 373 | 5.9 |
| 29.9 | 137 | 2.2 |
| 30.5 | 106 | 1.7 |
| 31.0 | 408 | 6.4 |
| 31.1 | 518 | 8.2 |
| 32.1 | 105 | 1.7 |
| 32.3 | 158 | 2.5 |
| 33.0 | 186 | 2.9 |
| 33.5 | 66 | 1.0 |
| 33.9 | 118 | 1.9 |
| 34.0 | 275 | 4.3 |
| 34.4 | 78 | 1.2 |
| 35.1 | 54 | 0.9 |
| 36.3 | 122 | 1.9 |
| 36.8 | 103 | 1.6 |
| 37.3 | 56 | 0.9 |
| 38.8 | 58 | 0.9 |
| 39.4 | 86 | 1.4 |
| 39.4 | 76 | 1.2 |

Figure 24:
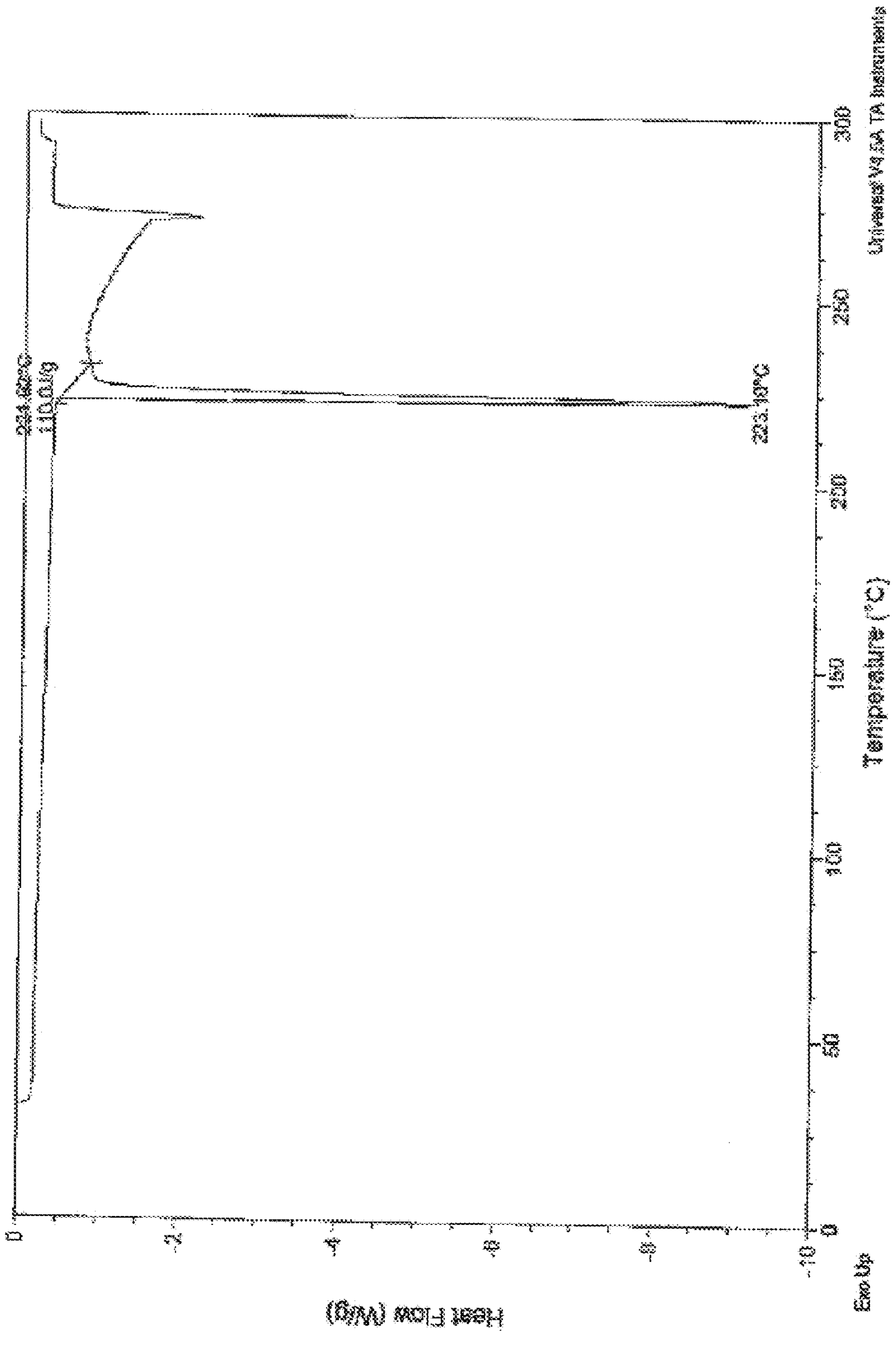
FIG. 24 depicts a DSC thermogram of the Free Form Type A of the compound of formula (I), prepared as described in Example 17.

The DSC thermogram of the free form type A is shown in FIG. 24. DSC analysis was performed on a TA 020 DSC instrument, with a ramp rate of 10.0° C./minute and using N2 as the purge gas. The thermogram comprises an endothermic peak having an onset temperature of 221.9° C. and a peak temperature of 223.1° C.

Figure 25:
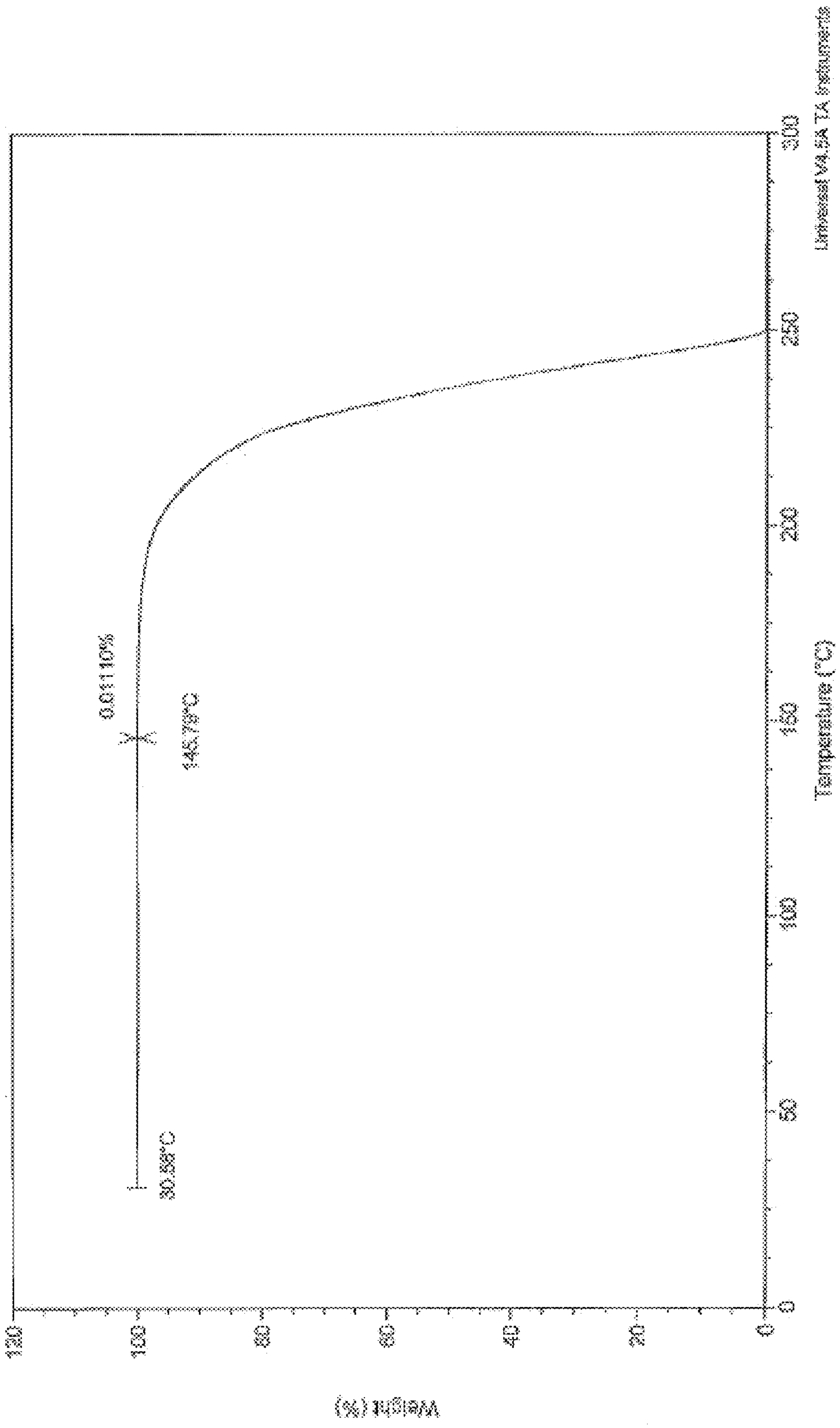
FIG. 25 depicts a TGA thermogram of the Free Form Type A of the compound of formula (I), prepared as described in Example 17.

The TGA curve of the free form type A is shown in FIG. 25. TGA was performed on a TA Q5000 IR TGA system at a ramp rate of 10° C./minute and using N2 as the purge gas. The curve reflects a 0.011% loss of weight.

The purity profile of the free form type A was determined by HPLC analysis (Method 1). The concentrations (w/w %) of Compounds 2-7, and total impurities are reported in Table 16. The concentrations (w/w %) were determined by HPLC peak area, based on the assumption that Compounds 1-7 have a relative response factor of 1. The concentration (w/w %) of each compound reported in Table 16 reflects the HPLC peak area attributed to the compound, as a percentage of the total peak area attributable to Compound 1 and any organic impurities. The concentration (w/w %) of total impurities reported in Table 16 reflects the total HPLC peak area attributed to organic impurities (Compounds 2-7), as a percentage of the total peak area attributable to Compound 1 and any organic impurities. The stereoisomers of Compound 1 (Compounds 8 and 9) co-elute with Compound 1 under the conditions of HPLC Method 1 and therefore are not included in the concentration of total impurities.

TABLE 16

| Batch Analysis of Free Form Type A by HPLC Method 1 | |
|---|---|
| Compound | Result (w/w %) |
| Compound 3 | |
| Compound 4 | |
| Compound 6 | 0.05% |
| Compound 5 | 0.12% |
| Compound 7 | |
| Compound 2 | 0.10% |
| Total Impurities | 0.27% |

The stereochemical purity of the free form type A was determined by HPLC analysis (Method 2). The concentrations (w/w %) of Compounds 8 and 9 are reported in Table 17. The concentrations (w/w %) were determined by HPLC peak area, based on the assumption that Compounds 1, 8, and 9 have a relative response factor of 1. The concentrations of Compounds 8 and 9 reported in Table 17 reflect the HPLC peak area attributed to the compound, as a percentage of the total peak area attributable to Compounds 1, 8, and 9.

TABLE 17

| Batch Analysis of Free Form Type A by HPLC Method 2 | |
|---|---|
| Compound | Result (w/w %) |
| Compound 8 | 0.33% |
| Compound 9 | Not Detected |

Example 17

Single Crystal X-Ray Diffraction Analysis of Free Form Type A of Compound 1

Single colourless needle-shaped crystals of Compound 1 were recrystallised from a mixture of dichloromethane and toluene by slow evaporation.

A suitable crystal (0.55×0.17×0.11 mm3) was selected and mounted on a nylon loop with paratone oil. Data were collected using a Bruker APEX-II CCD diffractometer equipped with an Oxford Cryosystems low-temperature apparatus operating at T=173(2) K.

Data were measured using w and (p scans of 1.00° per frame for 30.00 s using CuKα radiation (sealed tube, 40 kV, 30 mA). The total number of runs and images was based on the strategy calculation from the program COSMO (BRUKER, V1.61, 2009). The actually achieve resolution was Θ=72.008.

Cell parameters were retrieved using the SAINT (Bruker, V8.34A, 2013) software and refined using SAINT (Bruker, V8.34A, 2013) on 9424 reflections, 34 of the observed reflections.

Data reduction was performed using the SAINT (Bruker, V8.34A, 2013) software which corrects for Lorentz polarisation. The final completeness is 100.00 out to 72.008 in Θ. The absorption coefficient (MU) of this material is 2.490 and the minimum and maximum transmissions are 0.5542 and 0.7536.

The structure was solved by Direct Methods using the ShelXS (Sheldrick G M. A short history of SHELX. *Acta Crystallogr A,* 2008, 64: 112-122) structure solution program and refined by Least Squares using version 2014/6 of XL (Sheldrick G M. A short history of SHELX. *Acta Crystallogr A,* 2008, 64:112-122).

The structure was solved in the space group C2221 (#20). All non-hydrogen atoms were refined anisotropically. Hydrogen atom positions were calculated geometrically and refined using the riding model except for those that reside on hetero atoms. These were found by difference Fourier methods and refined isotropically. Structure refined by least squares method on F2, ShelXL-97, incorporated in Olex2 (O. V. Dolomanov, L. J. Bourhis, R. J. Gildea, J. A. K. Howard and H. Puschmann. "OLEX2: a complete structure solution, refinement and analysis program". *J. Appl. Cryst.* 2009, 42, 339-341). All H atoms were placed in calculated positions and refined using a riding model.

The Flack parameter was refined to 0.025(5), confirming the absolute stereochemistry. Determination of absolute structure using Bayesian statistics on Bijvoet differences using the program within PLATON (A. L. Spek, Single-crystal structure validation with the program PLATON, J. Appl. Cryst., (2003), 36, 7-13) also report that we have the correct enantiomer based on this comparison.

Figure 26:
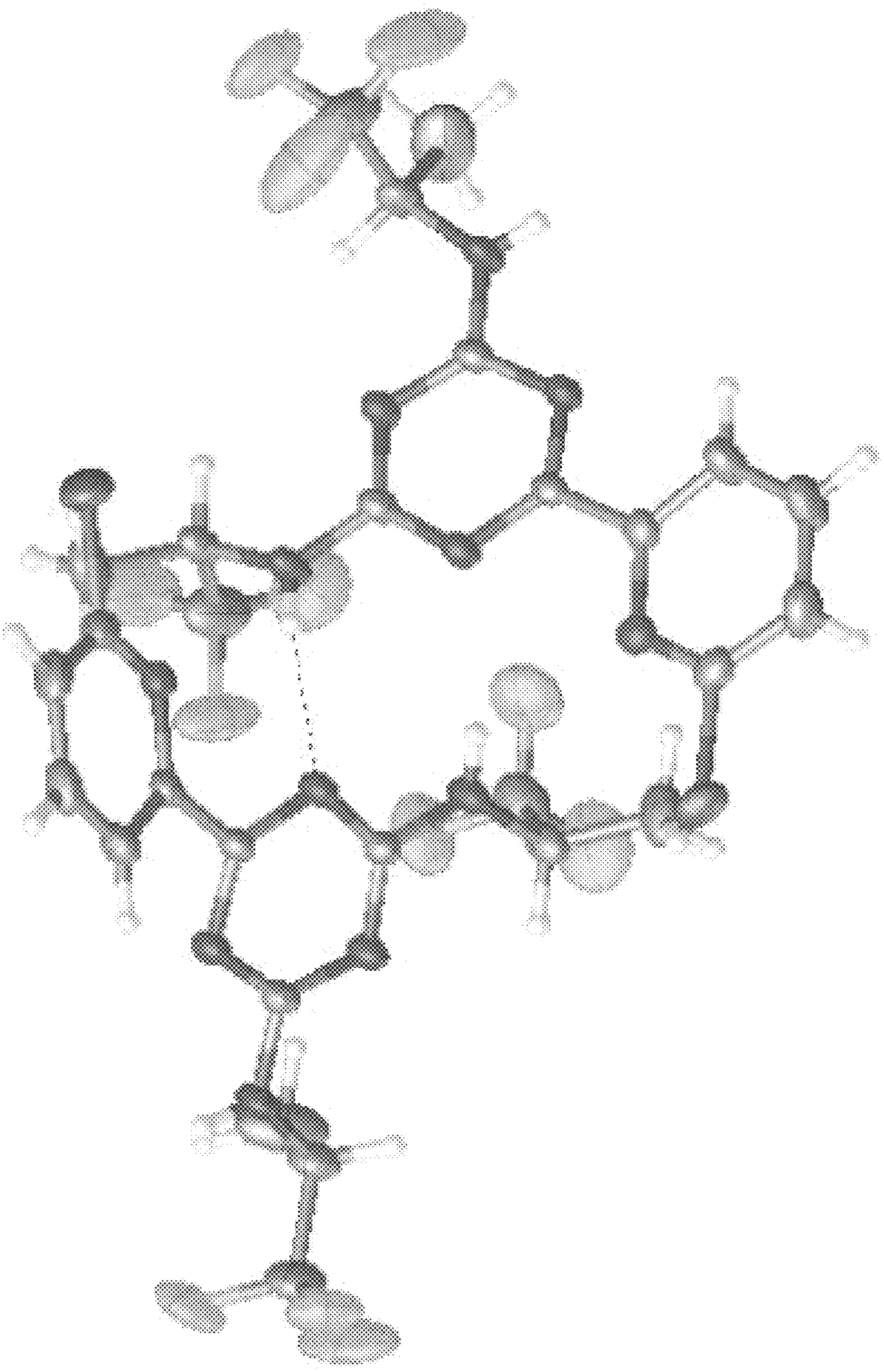
FIG. 26 depicts an Oak Ridge Thermal Ellipsoid Plot (ORTEP) of a single crystal of the Free Form Type A of the compound of formula (I), prepared as described in Example 18.
Figure 27:
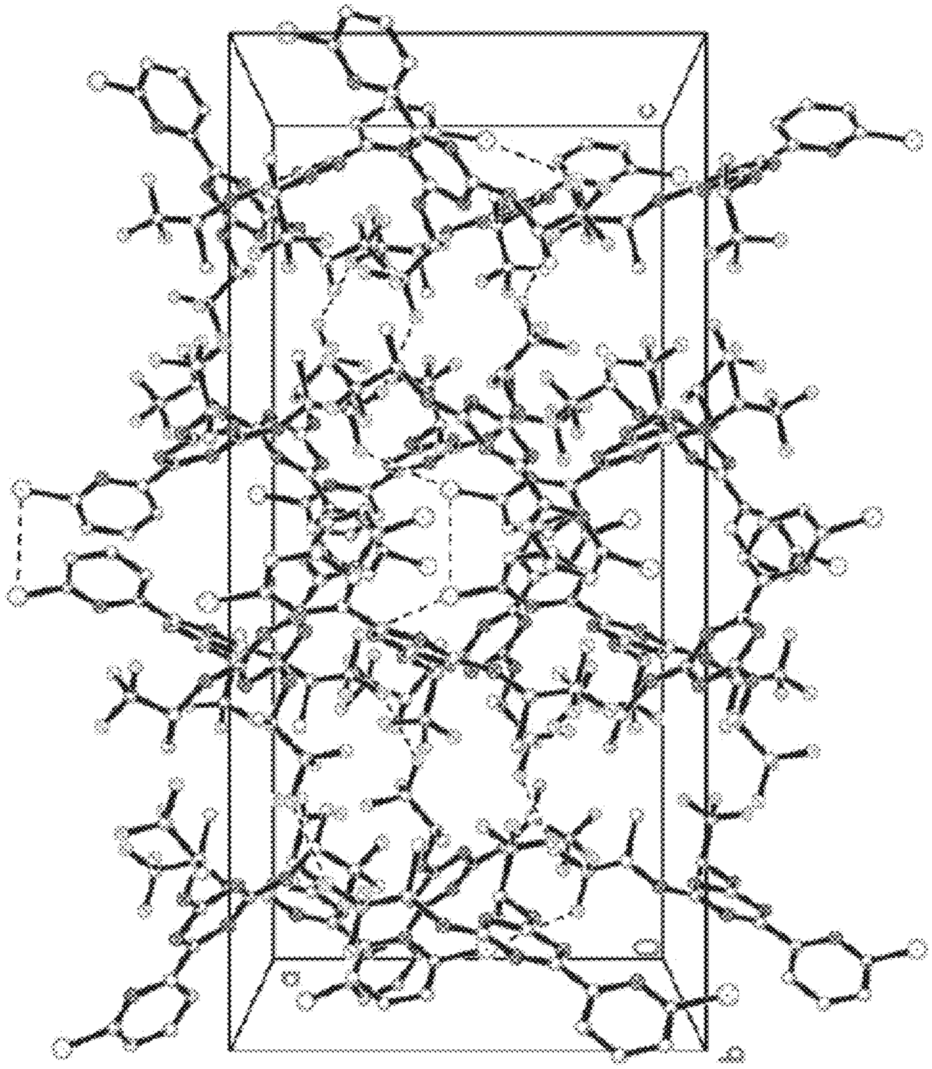
FIG. 27 depicts a unit cell diagram of a single crystal of the Free Form Type A of the compound of formula (I), prepared as described in Example 18.

The crystal data are listed in Table 18. An ORTEP drawing of the crystal structure is shown in FIG. 26, and the unit cell is shown in FIG. 27. A simulated powder diffraction pattern based on the single crystal intensity data was consistent with the XRPD pattern of free form type A, as described in Example 17.

TABLE 18

| Crystal Data Free Form Type A Single Crystal | |
|---|---|
| Formula | $C_{28}H_{26}Cl_2F_{12}N_{12}$ |
| Formula Weight | 829.51 |
| Crystal System | Orthorhombic |
| Space Group | $C222_1$ (#20) |
| Unit Cell Dimensions | a = 13.6484(3) Å |
| | b = 18.6176(4) Å |
| | c = 29.1682(6) Å |
| | $\alpha = \beta = \gamma = 90°$ |
| Volume | 7411.7(3) $Å^3$ |
| Temperature | 173(2) K |
| Z | 8 |
| Z' | 1 |
| $\mu$ ($CuK_\alpha$) | 2.490 $mm^{-1}$ |
| Reflections Measured | 27896 |
| Independent Reflections | 7202 |
| $wR_2$ (all data) | 0.0859 |
| $R_1$ | 0.0334 |

Example 18

Preparation and Characterization of Free Form Type B of Compound 1

A 20 mL vial was charged with 100 mg of Compound 1 (Free Form Type A) and 1 mL of methyl isobutyl ketone to form a solution. Heptane (15 mL) was added dropwise, and the mixture was stirred at room temperature for 90 minutes, during which time a precipitate formed. The precipitate was isolated and dried to afford Free Form Type B of Compound 1. Free Form Type B was analyzed by XRPD, DSC, and TGA analysis.

Figure 28:
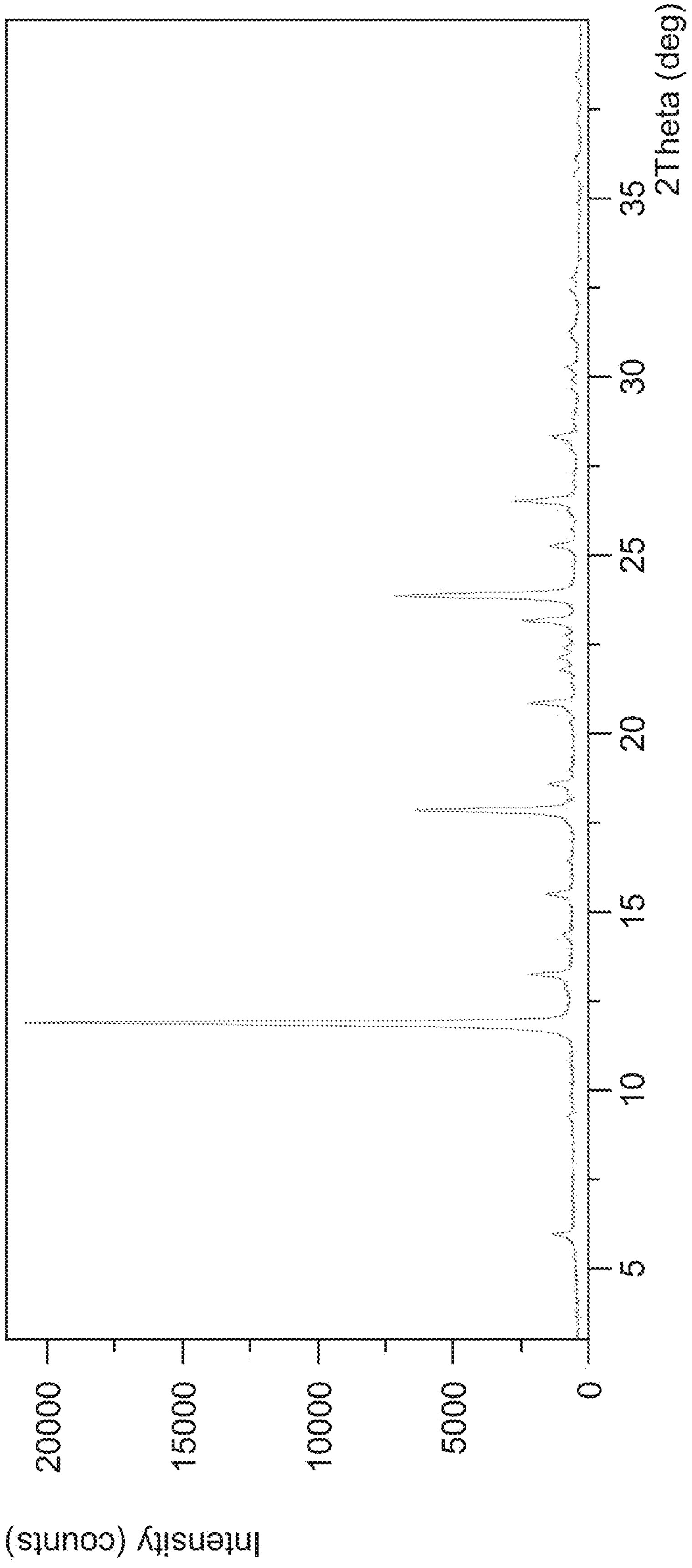
FIG. 28 depicts an XRPD pattern of the Free Form Type B of the compound of formula (I), prepared as described in Example 19.

The XRPD pattern of Free Form Type B, acquired on a PANalytical Empyrean diffractometer in reflection mode, is shown in FIG. 28. The peak positions, peak heights, and relative intensities of the peaks in the XRPD pattern are listed in Table 19.

TABLE 19

XRPD Peaks of Free Form Type B

| Position [°2 Theta] | Height [counts] | Relative Intensity [%] |
|---|---|---|
| 6.0 | 852 | 4.3 |
| 9.3 | 140 | 0.7 |
| 11.9 | 19684 | 100.0 |
| 12.8 | 386 | 2.0 |
| 13.2 | 1609 | 8.2 |
| 14.4 | 437 | 2.2 |
| 15.5 | 1060 | 5.4 |
| 16.4 | 229 | 1.2 |
| 17.8 | 5904 | 30.0 |
| 18.6 | 1016 | 5.2 |
| 19.0 | 218 | 1.1 |
| 20.3 | 212 | 1.1 |
| 20.8 | 1684 | 8.6 |
| 21.8 | 601 | 3.1 |
| 22.1 | 686 | 3.5 |
| 22.4 | 498 | 2.5 |
| 22.8 | 408 | 2.1 |
| 23.2 | 2007 | 10.2 |
| 23.9 | 6622 | 33.6 |
| 25.2 | 966 | 4.9 |
| 25.8 | 257 | 1.3 |
| 26.2 | 392 | 2.0 |
| 26.5 | 2280 | 11.6 |
| 28.3 | 962 | 4.9 |
| 29.7 | 283 | 1.4 |
| 29.9 | 233 | 1.2 |
| 30.2 | 435 | 2.2 |
| 31.3 | 382 | 1.9 |
| 32.4 | 305 | 1.65 |
| 32.7 | 244 | 1.2 |

Figure 29:
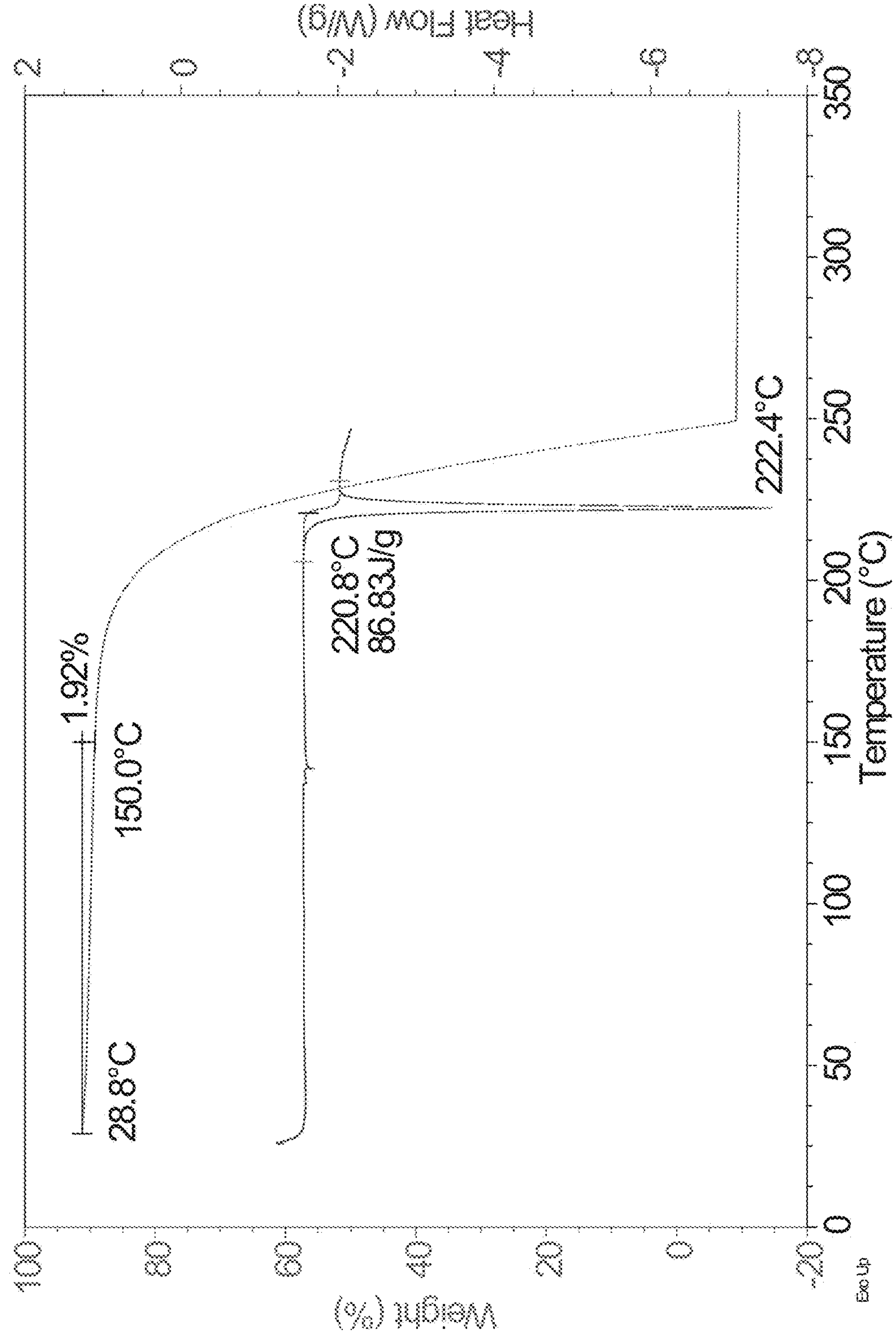
FIG. 29 depicts DSC and TGA thermograms of the Free Form Type B of the compound of formula (I), prepared as described in Example 19.

The DSC and TGA thermograms of Free Form Type B are shown in FIG. 29. DSC analysis was performed with a TA instruments 02000 DSC in crimped Aluminum pan. DSC analysis was performed over a temperature range from room temperature to 300° C. at a ramp rate of 10° C. per minute, with N2 as the purge gas. TGA was conducted at 10° C./min ramping from RT to 350 CC in open Platinum pan using a TA Instruments Q5000 TGA, with N2 as the purge gas. The DSC thermogram comprises an endothermic peak having an onset temperature of 221.5 CC. The TGA thermogram indicates a 2.3% weight loss up to 150 CC.

Example 19

Single Crystal X-Ray Diffraction Analysis of Free Form Type B of Compound 1

Single crystals suitable for structure determination were obtained by vapor diffusion in THF/heptane (1/3, v/v) co-solvents system. Free Form Type A of Compound 1 (21.0 mg) was weighed into a 3-mL vial with addition of 0.5 mL THF/heptane (1/3, v/v) co-solvents. The solution was filtered with a nylon filter (0.45 μm) and collected into three 4-mL vials. Seeds of Free form Type B were added into the vials. The vials were placed into a 20-mL vial (with 4 mL heptane as anti-solvent), and the 20-mL vial was capped. The vials were kept at room temperature, and the heptane was allowed to diffuse into the THF/heptane solution. After three days, plate-like crystals of Free Form Type B were obtained.

X-ray intensity data from a prism-like crystal were collected at 290(2) K using a Bruker D8 ADVANCE diffractometer (Mo Kα radiation, λ=0.71073 Å). An XRPD pattern of an authentic sample of Free Form Type B was collected with an XPERT-3 Empyrean system at RT.

Direct methods structure solution, difference Fourier calculations and full-matrix least-squares refinement against F2 were performed with SHELXTL (Sheldrick G M. A short history of SHELX. *Acta Crystallogr A,* 2008, 64:112-122) and OLEX2 (O. V. Dolomanov, L. J. Bourhis, R. J. Gildea, J. A. K. Howard and H. Puschmann. "OLEX2: a complete structure solution, refinement and analysis program". *J. Appl. Cryst.* 2009, 42, 339-341). Molecular graphics were created by Diamond (Brandenburg, K. *DIAMOND,* 1999, Crystal Impact GbR, Bonn, Germany) and Mercury (Macrae, C. F., Edgington, P. R., McCabe, P., Pidcock, E., Shields, G. P., Taylor, R., Towler, M. & van de_Streek, J. *J. Appl. Cryst.* 2006, 39, 453-457). A simulated XRPD diagram was performed by Mercury (Macrae, C. F., Edgington, P. R., McCabe, P., Pidcock, E., Shields, G. P., Taylor, R., Towler, M. & van de Streek, J. *J. Appl. Cryst.* 2006, 39, 453-457).

Figure 30:
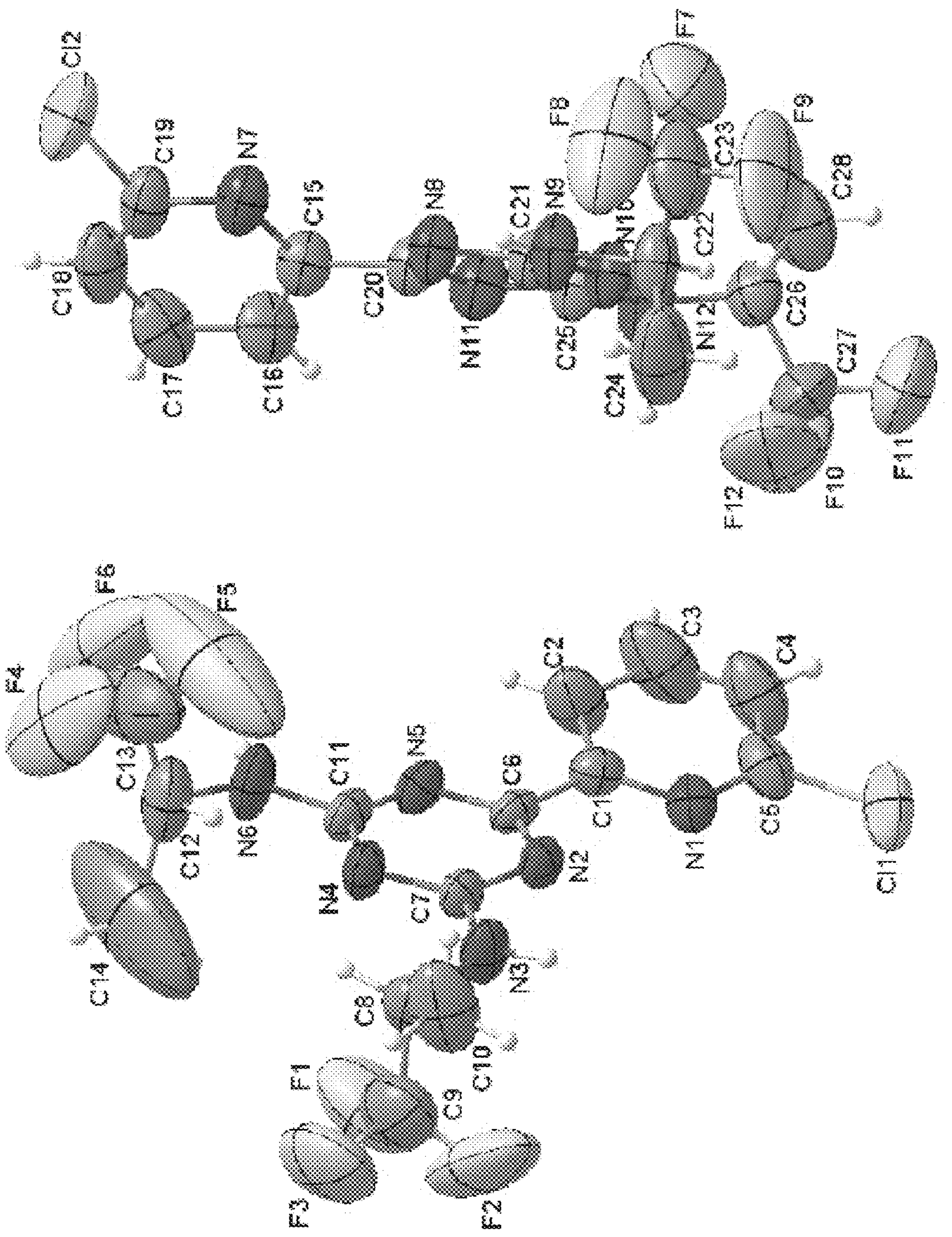
FIG. 30 depicts an Oak Ridge Thermal Ellipsoid Plot (ORTEP) of a single crystal of the Free Form Type B of the compound of formula (I), prepared as described in Example 20.
Figure 31:
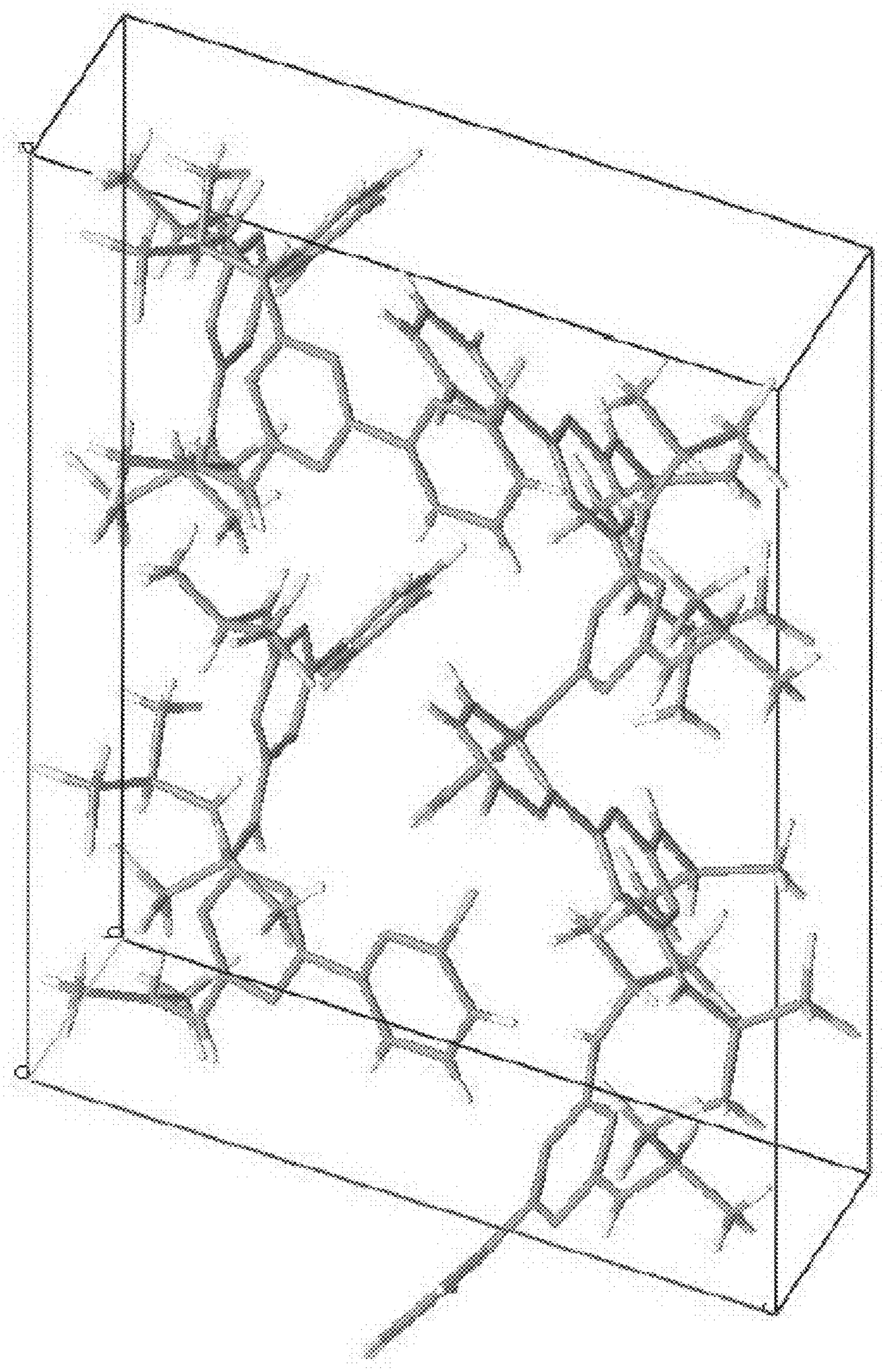
FIG. 31 depicts a unit cell diagram of a single crystal of the Free Form Type B of the compound of formula (I), prepared as described in Example 20.

The single crystal structure of Free Form Type B was successfully determined. Free Form Type B was confirmed to be an anhydrate and to have eight molecules of Compound 1 per unit cell. The details of crystal data and structure refinement are listed in Table 20. An ORTEP drawing of the crystal structure is shown in FIG. 30, and the unit cell is shown in FIG. 31. A simulated XRPD pattern based on the single crystal data and an experimental XRPD pattern obtained from an authentic sample of Free Form Type B were in good agreement.

TABLE 20

Crystal Data and Structure Refinement for Free Form Type B Single Crystal

| | |
|---|---|
| Empirical formula | $C_{14}H_{13}ClF_6N_6$ |
| Formula weight | 414.75 |
| Temperature | 295(2) K |
| Wavelength | 0.71073 Å |
| Crystal system, space group | Monoclinic, C2 |
| Unit cell dimensions | a = 18.712(5) Å |
| | b = 13.629(4) Å |
| | c = 15.527(4) Å |
| | α = 90 deg |
| | β = 106.006(7) deg |
| | γ = 90 deg |
| Volume | 3806.3(17) $Å^3$ |
| Z, Calculated density | 8, 1.448 $Mg/m^3$ |
| Absorption coefficient | 0.268 $mm^{-1}$ |
| F(000) | 1680 |
| Crystal size | 0.23 × 0.20 × 0.06 $mm^3$ |
| Theta range for data collection | 2.30-27.61 deg. |
| Limiting indices | $-24 \le h \le 24$ |
| | $-17 \le k \le 17$ |
| | $-20 \le l \le 20$ |
| Reflections collected/unique | 29267/8664 [R(int) = 0.0270] |
| Completeness | 98.8% |
| Refinement method | Full-matrix least-squares on $F^2$ |
| Data/restraints/parameters | 8664/1/491 |
| Goodness-of-fit on $F^2$ | 1.045 |
| Final R indices [I > 2sigma(I)] | $R_1$ = 0.0798, wR2 = 0.2317 |
| Largest diff, peak and hole | 0.746 and −0.365 e · $Å^{-3}$ |
| Absolute structure parameter | 0.06(9) |

Example 20

Preparation and Characterization of Free Form Type C of Compound 1

A 20 mL vial was charged with 150 mg of Compound 1 (Free Form Type A) and 1.5 mL of 1,4-dioxane to form a solution. Water (2.25 ml) was added dropwise, and the resulting suspension was stirred at room temperature for 3 days. The solid material was isolated and dried to afford Free Form Type C of Compound 1. Free Form Type C was analyzed by XRPD, DSC, and TGA analysis.

Figure 32:
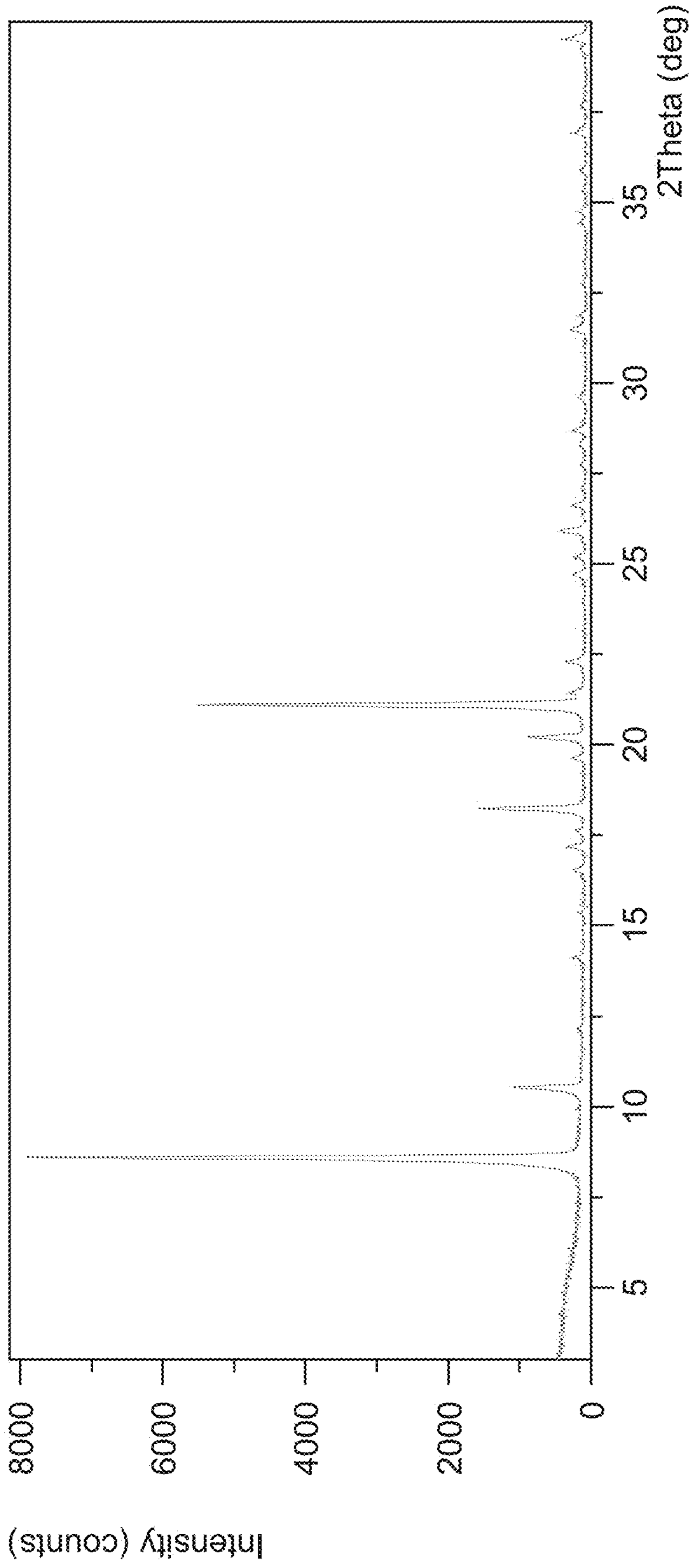
FIG. 32 depicts an XRPD pattern of the Free Form Type C of the compound of formula (I), prepared as described in Example 21.

The XRPD pattern of Free Form Type C, acquired on a PANalytical Empyrean diffractometer in reflection mode, is shown in FIG. 32. The peak positions, peak heights, and relative intensities of the peaks in the XRPD pattern are listed in Table 21.

TABLE 21

XRPD Peaks of Free Form Type C

| Position [°2 Theta] | Height [counts] | Relative Intensity [%] |
|---|---|---|
| 8.6 | 7658 | 100.0 |
| 10.5 | 973 | 12.7 |
| 12.1 | 49 | 0.6 |
| 14.1 | 126 | 1.7 |
| 16.5 | 137 | 1.8 |
| 17.9 | 214 | 2.8 |
| 17.6 | 92 | 1.2 |
| 18.2 | 1444 | 18.9 |
| 19.6 | 158 | 2.1 |
| 20.2 | 782 | 10.2 |
| 21.1 | 5298 | 69.2 |
| 21.5 | 205 | 2.7 |
| 22.3 | 254 | 3.3 |
| 24.7 | 151 | 2.0 |
| 25.2 | 146 | 1.9 |
| 25.9 | 368 | 4.8 |
| 26.6 | 177 | 2.3 |
| 27.1 | 36 | 0.5 |
| 27.7 | 60 | 0.8 |
| 28.3 | 74 | 1.0 |
| 28.7 | 178 | 2.3 |
| 29.6 | 71 | 0.9 |
| 31.5 | 211 | 2.8 |
| 31.9 | 105 | 1.4 |
| 32.8 | 39 | 0.5 |
| 34.4 | 65 | 0.9 |
| 34.7 | 101 | 1.3 |
| 35.3 | 35 | 0.5 |
| 35.9 | 52 | 0.7 |
| 37.0 | 135 | 1.8 |
| 37.7 | 65 | 0.9 |
| 39.5 | 300 | 3.9 |

Figure 33:
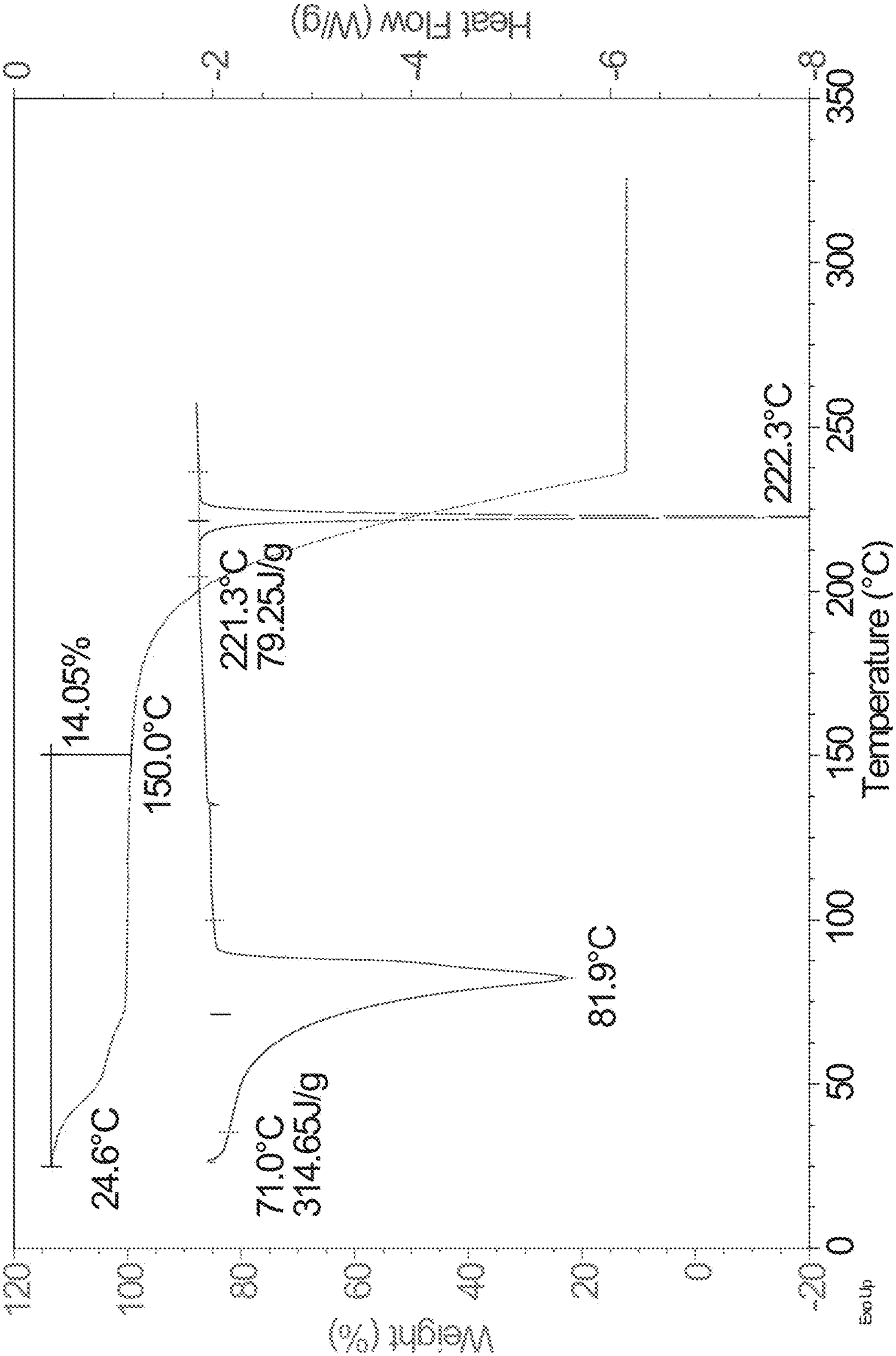
FIG. 33 depicts DSC and TGA thermograms of the Free Form Type C of the compound of formula (I), prepared as described in Example 21.

The DSC and TGA thermograms of Free Form Type C are shown in FIG. 33. DSC analysis was performed with a TA instruments 02000 DSC in crimped Aluminum pan. DSC analysis was performed over a temperature range from room temperature to 300° C. at a ramp rate of 10° C. per minute, with N2 as the purge gas. TGA was conducted at 10° C./min ramping from RT to 350° C. in open Platinum pan using a TA Instruments Q5000 TGA, with N2 as the purge gas. The DSC thermogram comprises endothermic peaks at 81.9° C. (peak temperature) and 221.3° C. (onset temperature). The TGA thermogram indicates a 14.1% weight loss up to 150° C.

Example 21

Single Crystal X-Ray Diffraction Analysis of Free Form Type C of Compound 1

Single crystals suitable for structure determination were obtained by slow evaporation in ACN/$H_2O$ (4/1, v/v). Free Form Type A of Compound 1 (4.2 mg) and citric acid (2.1 mg) were weighed into a 3-mL vial, and 0.5 mL ACN/$H_2O$ (4/1, v/v) was added. The solution was filtered to a single crystal vial, and the solvent was allowed to evaporate. After seven days, lath crystals of Free Form Type C were obtained.

X-ray intensity data from a prism-like crystal were collected at 290(2) K using a Bruker D8 ADVANCE diffractometer (Mo Kα radiation, λ=0.71073 Å). An XRPD pattern of an authentic sample of Free Form Type C was collected with an XPERT-3 Empyrean system at RT.

Direct methods structure solution, difference Fourier calculations and full-matrix least-squares refinement against F2 were performed with SHELXTL (Sheldrick G M. A short history of SHELX. *Acta CrystallogrA,* 2008, 64:112-122) and OLEX2 (O. V. Dolomanov, L. J. Bourhis, R. J. Gildea, J. A. K. Howard and H. Puschmann. "OLEX2: a complete structure solution, refinement and analysis program". *J. Appl. Cryst.* 2009, 42, 339-341). Molecular graphics were created by Diamond (Brandenburg, K. *DIAMOND,* 1999, Crystal Impact GbR, Bonn, Germany) and Mercury (Macrae, C. F., Edgington, P. R., McCabe, P., Pidcock, E., Shields, G. P., Taylor, R., Towler, M. & van de_Streek, J. *J. Appl. Cryst.* 2006, 39, 453-457). A simulated XRPD diagram was performed by Mercury (Macrae, C. F., Edgington, P. R., McCabe, P., Pidcock, E., Shields, G. P., Taylor, R., Towler, M. & van de Streek, J. *J. Appl. Cryst.* 2006, 39, 453-457).

Figure 34:
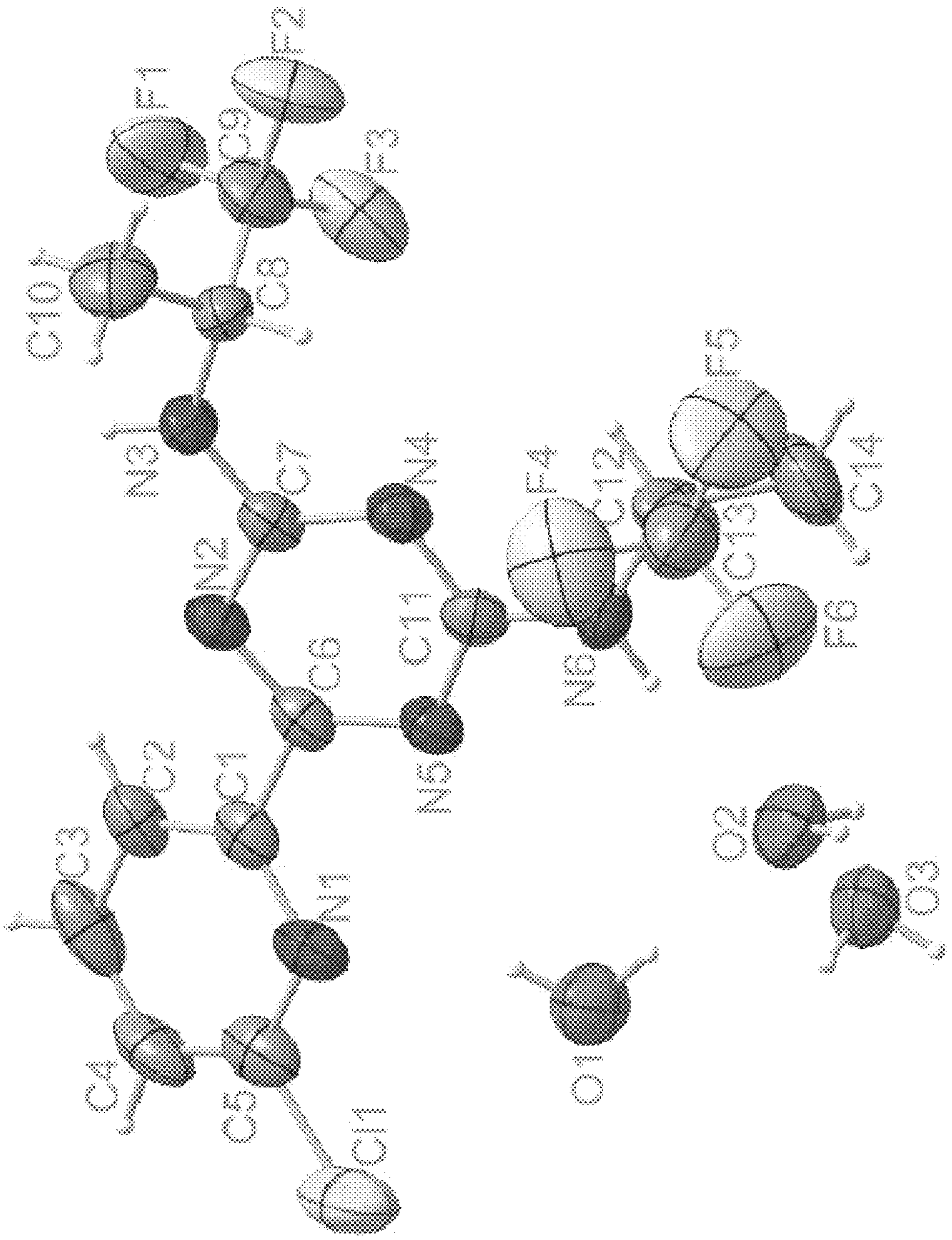
FIG. 34 depicts an Oak Ridge Thermal Ellipsoid Plot (ORTEP) of a single crystal of the Free Form Type C of the compound of formula (I), prepared as described in Example 22.
Figure 35:
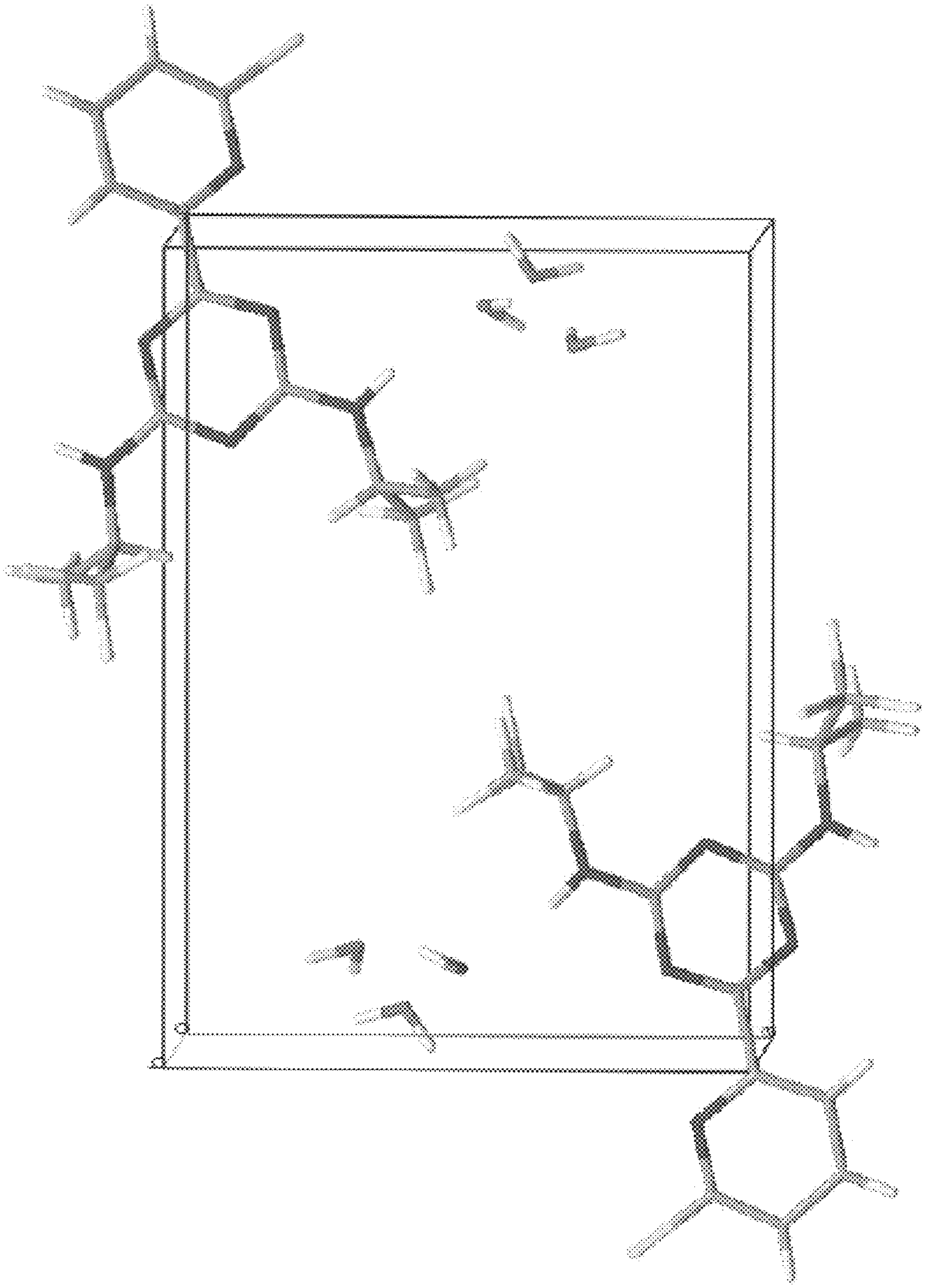
FIG. 35 depicts a unit cell diagram of a single crystal of the Free Form Type C of the compound of formula (I), prepared as described in Example 22.

The single crystal structure of Free Form Type C was successfully determined. Free Form Type C was confirmed to be a trihydrate having two molecules of Compound 1 and six molecules of water per unit cell. The details of crystal data and structure refinement are listed in Table 22. An ORTEP drawing of the crystal structure is shown in FIG. 34, and the unit cell is shown in FIG. 35. A simulated XRPD pattern based on the single crystal data and an experimental XRPD pattern obtained from an authentic sample of Free Form Type C were in good agreement.

TABLE 22

Crystal Data and Structure Refinement for Free Form Type C Single Crystal

| | | |
|---|---|---|
| Empirical formula | $C_{14}H_{19}ClF_6N_6O_3$ | |
| Formula weight | 468.80 | |
| Temperature | 290(2) K | |
| Wavelength | 0.71073 Å | |
| Crystal system, space group | Monoclinic | $P2_1$ |
| Unit cell dimensions | a = 10.407(7) Å | α = 90 deg. |
| | b = 6.961(5) Å | β = 90.089(17) deg. |
| | c = 14.575(10) Å | γ = 90 deg |
| Volume | 1055.9(12) $Å^3$ | |
| Z, Calculated density | 2 | 1.474 $Mg/m^3$ |
| Absorption coefficient | 0.260 $mm^{-1}$ | |
| F(000) | 480 | |
| Crystal size | 0.30 × 0.20 × 0.13 $mm^3$ | |
| Theta range for data collection | 2.40-24.04 deg. | |
| Limiting indices | $-11 \le h \le 10$ | |
| | $-7 \le k \le 7$ | |
| | $-16 \le l \le 15$ | |
| Reflections collected/unique | 5180/2117 [R(int) = 0.0323] | |
| Completeness | 70.8% | |
| Refinement method | Full-matrix least-squares on $F^2$ | |
| Data/restraints/parameters | 2117/2/275 | |
| Goodness-of-fit on $F^2$ | 1.025 | |
| Final R indices [I > 2sigma(I)] | $R_1$ = 0.0520 | $wR_2$ = 0.1354 |
| Largest diff. peak and hole | 0.665 and −0.269 e · $Å^{-3}$ | |
| Absolute structure parameter | −0.03(19) | |

Example 22

Preparation and Characterization of Free Form Type D of Compound 1

Free Form Type A of Compound 1 (135.0 mg) was suspended in 2.0 mL of 1,4-dioxane/heptane (4:1, v/v). The suspension was stirred at room temperature for 17 days, and the solid material was separated and air dried to afford Free Form Type 0 of Compound 1. Free Form Type 0 was analyzed by XRPD, $^1$H NMR, DSC, and TGA analysis.

Figure 36:
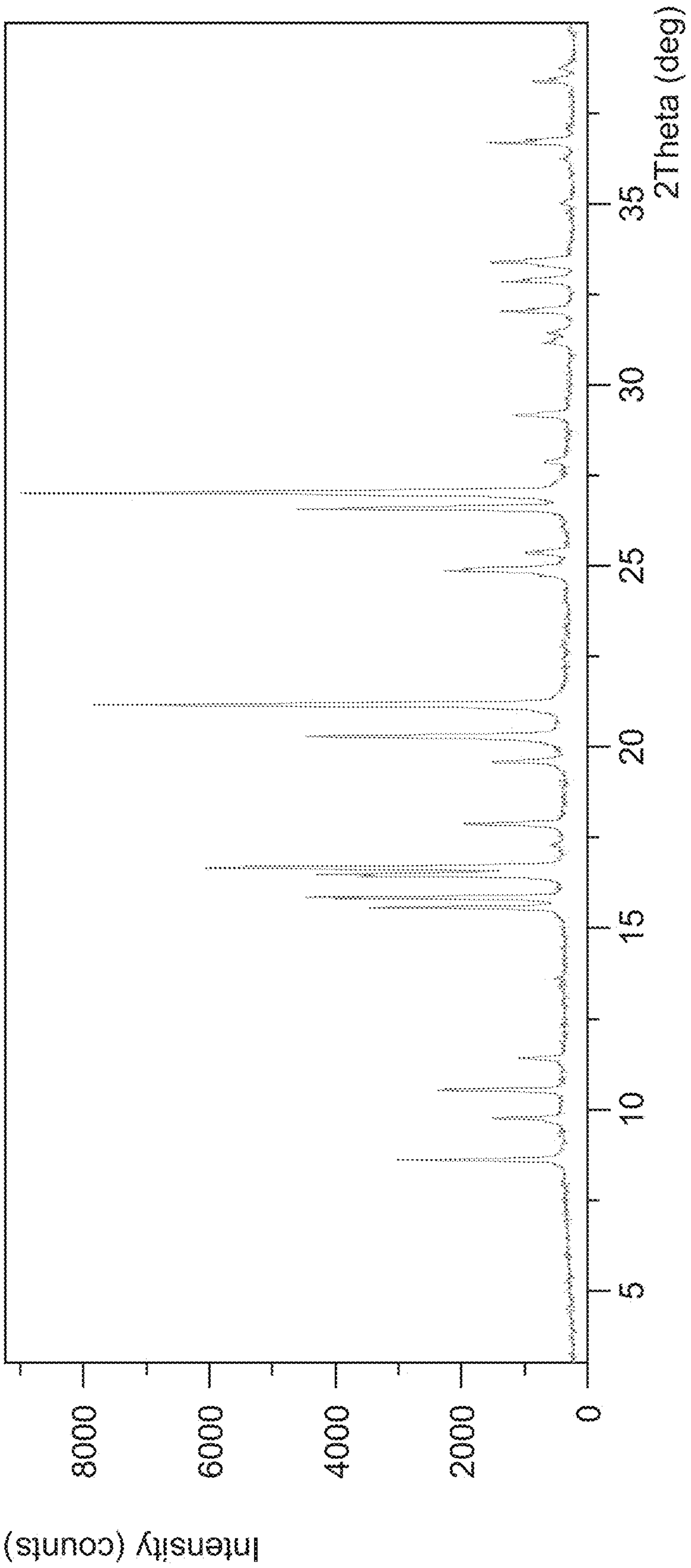
FIG. 36 depicts an XRPD pattern of the Free Form Type D of the compound of formula (I), prepared as described in Example 23.

The XRPD pattern of Free Form Type 0, acquired on a PANalytical Empyrean diffractometer in reflection mode, is shown in FIG. 36. The peak positions, peak heights, and relative intensities of the peaks in the XRPD pattern are listed in Table 23.

TABLE 23

XRPD Peaks of Free Form Type D

| Position [°2 Theta] | Height [counts] | Relative Intensity [%] |
|---|---|---|
| 8.6 | 1993 | 25.8 |
| 9.7 | 836 | 10.8 |
| 10.5 | 1821 | 23.5 |
| 11.4 | 610 | 7.9 |
| 13.6 | 112 | 1.5 |
| 15.6 | 2085 | 26.9 |
| 15.9 | 3906 | 50.5 |
| 16.7 | 5647 | 72.9 |
| 17.3 | 193 | 2.5 |
| 17.9 | 1637 | 21.2 |
| 19.6 | 1050 | 13.6 |
| 20.3 | 4116 | 53.2 |
| 21.2 | 6939 | 89.6 |
| 24.9 | 1743 | 22.5 |
| 25.4 | 672 | 8.7 |
| 26.6 | 3977 | 51.4 |
| 27.0 | 7741 | 100.0 |
| 27.9 | 421 | 5.4 |
| 29.2 | 884 | 11.4 |
| 31.2 | 400 | 5.2 |
| 31.4 | 373 | 4.8 |
| 32.0 | 1087 | 14.0 |
| 32.9 | 875 | 11.3 |
| 33.4 | 1256 | 16.2 |
| 35.0 | 181 | 2.3 |
| 36.2 | 168 | 2.2 |
| 36.7 | 1232 | 15.9 |
| 38.4 | 438 | 5.7 |
| 38.7 | 205 | 2.7 |

Figure 37:
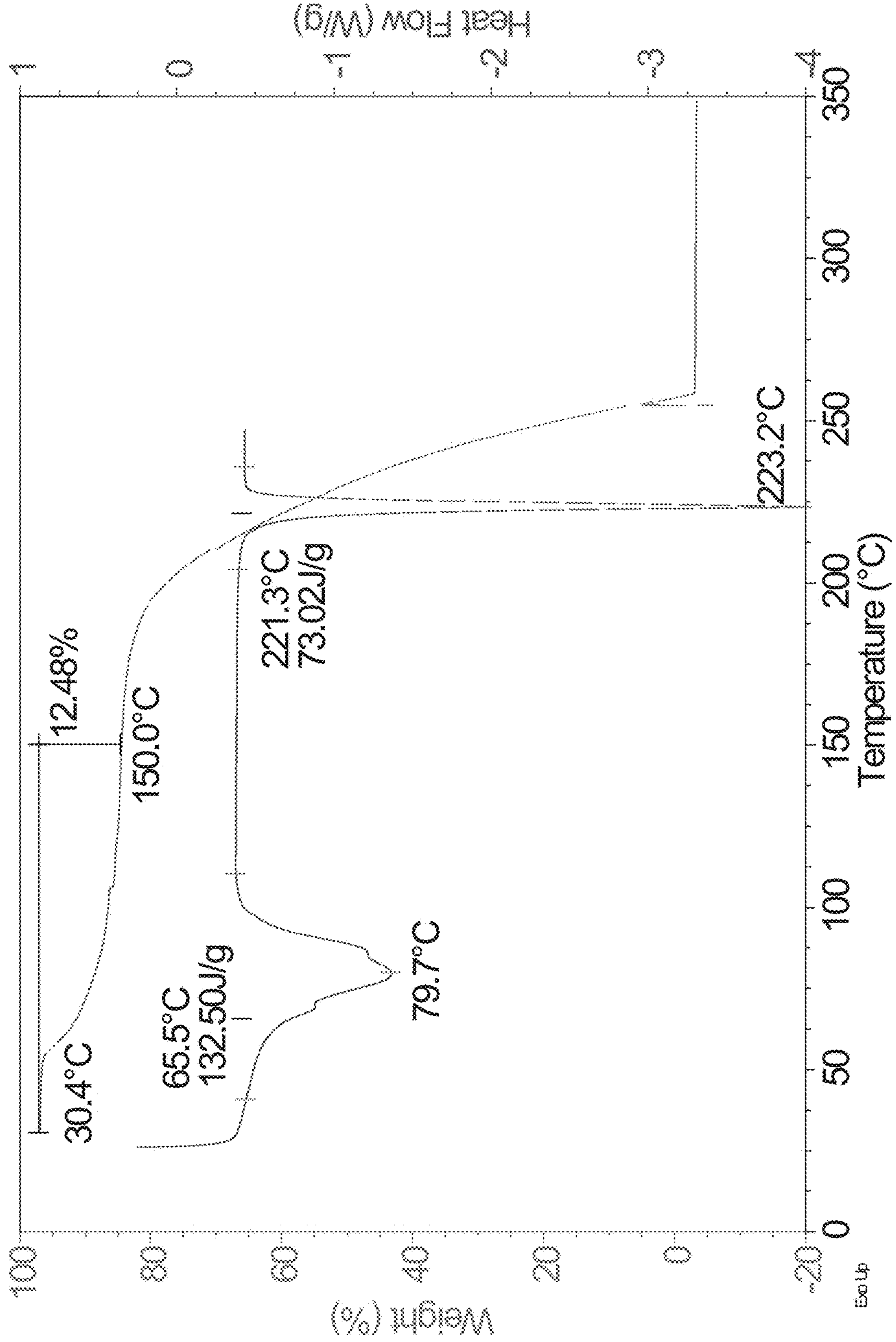
FIG. 37 depicts DSC and TGA thermograms of the Free Form Type D of the compound of formula (I), prepared as described in Example 23.

The DSC and TGA thermograms of Free Form Type B are shown in FIG. 37. DSC analysis was performed with a TA instruments 02000 DSC in crimped Aluminum pan. DSC analysis was performed over a temperature range from room temperature to 300° C. at a ramp rate of 10° C. per minute, with N2 as the purge gas. TGA was conducted at 10° C./min ramping from RT to 350° C. in open Platinum pan using a TA Instruments Q5000 TGA, with $N_2$ as the purge gas. The DSC thermogram comprises endothermic peaks at 79.7° C. (peak temperature) and 221.3° C. (onset temperature). The TGA thermogram indicates a 12.48% weight loss up to 150° C.

Figure 38:
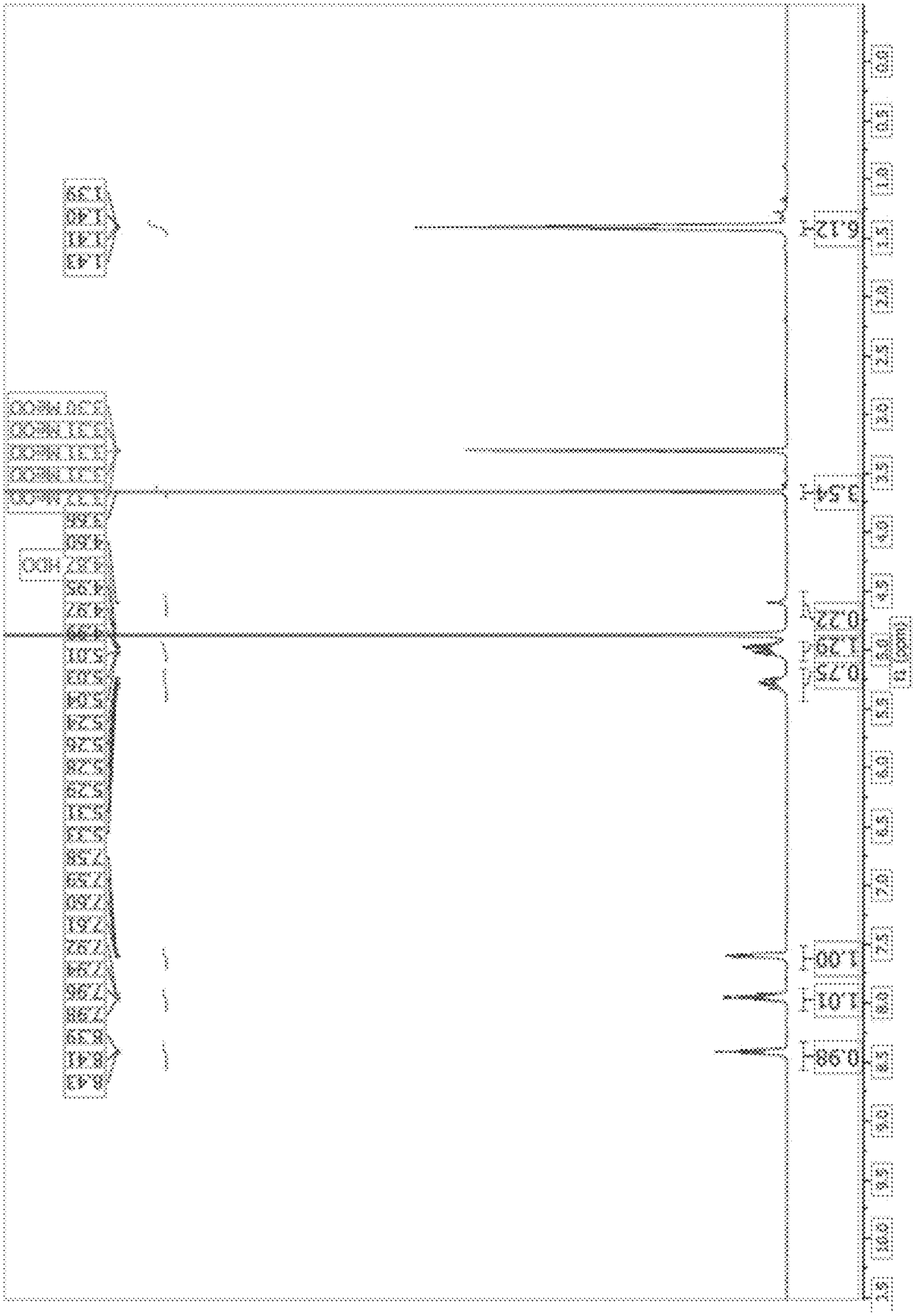
FIG. 38 depicts a $^{1}H$ NMR spectrum of the Free Form Type D of the compound of formula (I), prepared as described in Example 23.

The $^1$H NMR spectrum of Free Form Type D, taken in $CD_3OD$, is shown in FIG. 38. The peak integrations of the $^1$H NMR spectrum revealed that Free Form Type D is a dioxane solvate and that Compound 1 and Dioxane are present in a molar ratio of about 1.0:0.4. Partial $^1$H NMR ($CD_3OD$) δ 8.43-8.39 (m, 1H), 7.98-7.92 (m, 1H), 7.61-7.58 (m, 1H), 3.66 (s, 0.4H).

Example 23

Amorphous Solid Dispersion of Compound 1

A 50:50 spray-dried dispersion of Compound 1 and HPMCAS (hydroxypropyl methylcellulose acetate succinate) was prepared. A solution of Compound 1 and HPMCAS in acetone was spray dried on a Buchi B-290. After spray drying, the solid dispersion was dried overnight at 40° C. to remove residual solvent. XRPD analysis of the material obtained revealed a diffraction pattern consistent with an amorphous form. The material was determined by DSC analysis to be a monophasic solid dispersion with a single glass transition temperature ($T_g$=84.6° C.). Dissolution testing in simulated intestinal fluid demonstrated that the material can maintain sufficient supersaturation to achieve exposure in vivo.

Example 24

Pharmacokinetics of Compound 1 Solid Forms in Plasma Following Single PO Administration in Male Sprague Dawley Rats Study Design. Twelve (12) male Sprague Dawley rats (purchased from SLAC Laboratory Animal Co. LTD were randomized into four groups (3 animals per group). The animals were fasted overnight, the forms of Compound 1 shown in Table 24 were administered by oral gavage, and the animals were fed 4 hours post-dose. Each form of Compound 1 was administered as a suspension in water containing 0.5% microcrystalline cellulose and 0.1% Tween 80. The Dose Levels and Dose Concentrations shown in Table 24 are based on the corresponding amount of free Compound 1.

TABLE 24

Study Design

| Group | Form of Compound 1 | Dose Level (mg/kg) | Dose Conc. (mg/mL) | Dose Volume (mL/kg) |
|---|---|---|---|---|
| 1 | Free Form A | 10 | 2 | 5 |
| 2 | Free Form C | 10 | 2 | 5 |
| 3 | Citrate Cocrystal Type A | 11.7 | 2.34 | 5 |
| 4 | Maleate Cocrystal Type A | 10 | 2 | 5 |

Blood Collection. Blood was serially collected from each animal 0.083 hr, 0.25 hr, 0.5 hr, 1 hr, 2 hr, 4 hr, 8 hr, 24 hr, 48 hr, and 72 hrs post-dose. For each collection, the animal was restrained manually, and approximately 150 μL of blood sample was collected via the tail vein into $K_2$EDTA tubes. The blood samples were put on ice and centrifuged at 2000 g for 5 min to obtain plasma. Plasma samples were stored at approximately −70° C. until analysis.

To enable the calculation of oral bioavailability, Compound 1 was dissolved in a vehicle containing 10% N-Methyl-2-pyrrolidone (NMP), 10% Solutol HS 15, and 80% saline and administered at 1 mg/kg as intravenous (IV) bolus dose to a separate group of male Sprague-Dawley rats, and blood samples were collected at similar time points to those shown above. Further, plasma samples were obtained from the collected blood samples and stored at approximately −70° C. until analysis.

Further, the amorphous solid dispersion of Compound 1, as described in Example 23, was suspended in an aqueous vehicle containing 0.5% methyl cellulose (MC) and 0.2% Tween80 at 0.2 mg/mL concentration and dosed at 1 mg/kg as a single oral dose to a separate group of male Sprague-Dawley rats after an overnight fasting. Blood samples were collected at similar time points to those shown above. Further, plasma was harvested and stored at approximately −70° C. until analysis.

Sample Preparation and Analysis. The concentration of Compound 1 in the plasma samples was determined by LC-MS/MS analysis.

A 20 μL aliquot of each sample was diluted with 200 μL of acetonitrile containing dexamethasone as an internal standard (40 ng/mL). The resulting mixture was vortexed for 2 min and centrifuged at 5800 rpm for 10 min. A 2 μL sample was injected into LC-MS/MS.

LC-MS/MS analysis was conducted on a UPLC/MS-MS-018 (API-5500) system under the conditions set forth in Table 25.

TABLE 25

LC-MS/MS Conditions for Quantitation of Compound 1 in Plasma

| | |
|---|---|
| Column | Waters BEH $C_{18}$ (2.1 × 50 mm, 1.7 μm) |
| Mobile Phase A | $H_2O$-0.025% Formic Acid-1 mM $NH_4OAC$ |
| Mobile Phase B | MeOH-0.025% Formic Acid-1 mM $NH_4OAC$ |
| Flow Rate | 0.6 mL/min |
| Gradient Program | Analysis was conducted over a 1.5 minute gradient elution program employing Mobile Phase A (10-90%) and Mobile Phase B (10-90%). |

Figure 39:
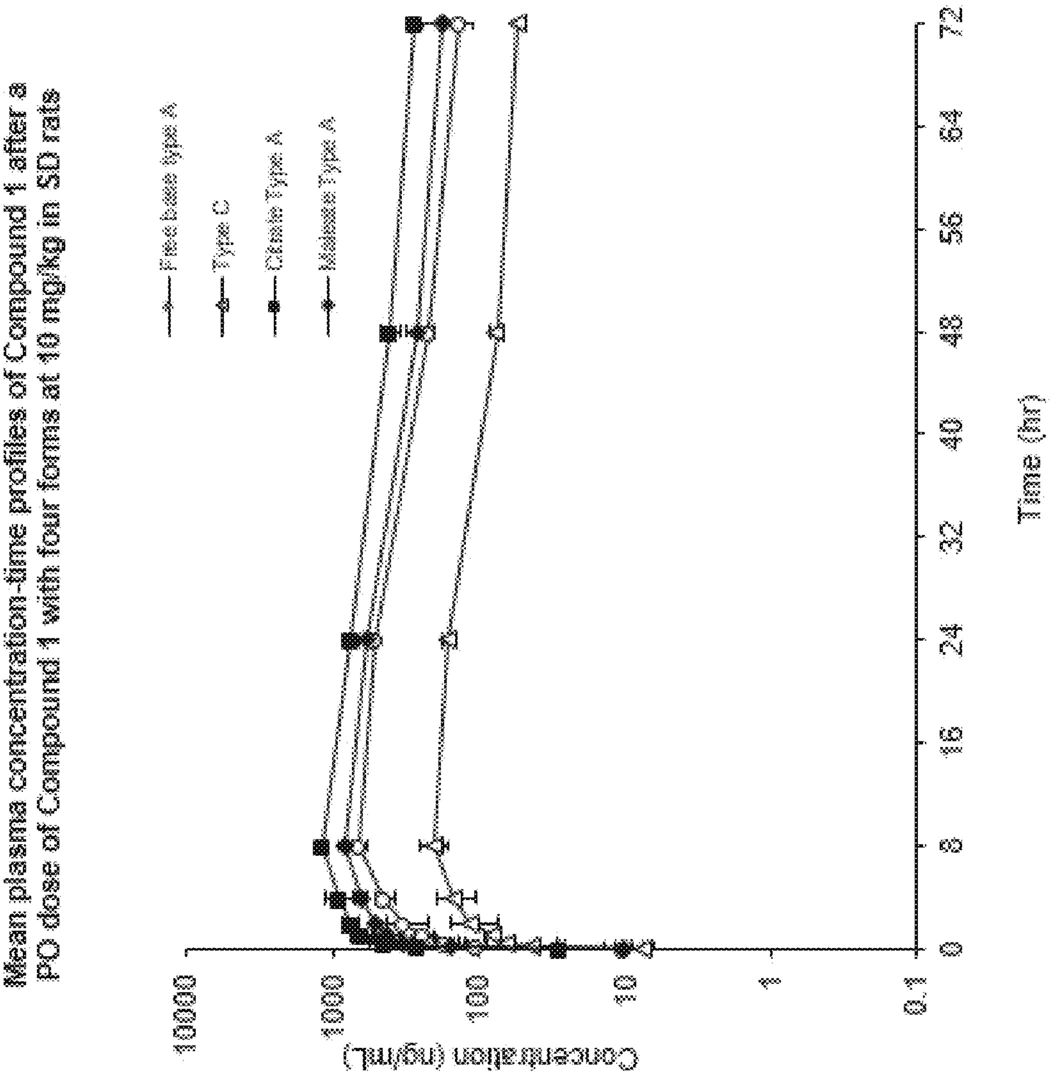
FIG. 39 depicts mean plasma-concentration time profiles of Compound 1 measured in the pharmacokinetic study described in Example 25.

Results. The mean plasma concentration-time profiles of Compound 1 in each of the four study groups are shown in FIG. 39. The $AUC_{inf}$ and absolute bioavailability (% F) of each form of compound 1 are reported in Table 26. Historical data for IV administration of Compound 1 and administration of Compound 1 as a spray dried dispersion are also provided in Table 26. The absolute bioavailability of each form of Compound 1 was determined by dividing the $AUC_{inf}$ of the form in question by the $AUC_{inf}$ obtained by IV administration of Compound 1 and correcting for differences in dose. The measured absolute bioavailability of the citrate and maleate cocrystals, as reported in Table 26, was higher than the measured bioavailability of the other forms of Compound 1.

TABLE 26

Absolute Bioavailability of Compound 1 Solid Forms

| Group | Form of Compound 1 | Dose Level (mg/kg) | $AUC_{inf}$ (ng · hr/mL) | Absolute % F |
|---|---|---|---|---|
| | IV Administration (historical) | 1 | 4802 | 100 |
| | Spray Dried Dispersion (historical) | 1 | 3436 | 71.6 |
| 1 | Free Form A | 10 | 30698 | 63.9 |
| 2 | Free Form C | 10 | 10846 | 22.6 |
| 3 | Citrate Cocrystal Type A | 11.7 | 58247 | 104 |
| 4 | Maleate Cocrystal Type A | 10 | 38625 | 80.4 |

What is claimed is:

1. A crystalline form of a compound of formula (I)

(I)

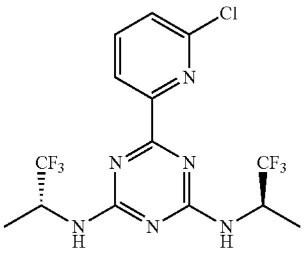

;

wherein the crystalline form comprises at least one peak position, in degrees 2-theta (±0.2 degrees 2-theta), selected from the group consisting of 11.7, 12.8, 14.2, 17.8, 19.8, 20.7, 21.8, 22.2, and 25.0.

2. The crystalline form of claim 1, wherein the crystalline form is characterized by an X-ray powder diffraction pattern, acquired in reflection mode, comprising at least two peak positions, in degrees 2-theta (±0.2 degrees 2-theta), selected from the group consisting of 11.7, 12.8, 14.2, 17.8, 19.8, 20.7, 21.8, 22.2, and 25.0.

3. The crystalline form of claim 1, wherein the X-ray powder diffraction pattern comprises at least three peak positions, in degrees 2-theta (±0.2 degrees 2-theta), selected from the group consisting of 11.7, 12.8, 14.2, 17.8, 19.8, 20.7, 21.8, 22.2, and 25.0.

4. The crystalline form of claim 1, wherein the X-ray powder diffraction pattern comprises at least four peak positions, in degrees 2-theta (±0.2 degrees 2-theta), selected from the group consisting of 11.7, 12.8, 14.2, 17.8, 19.8, 20.7, 21.8, 22.2, and 25.0.

5. The crystalline form of claim 1, wherein the X-ray powder diffraction pattern comprises peak positions, in degrees 2-theta (±0.2 degrees 2-theta), of 11.7, 17.8, and 21.8, and at least three peak positions selected from the group consisting of 12.8, 14.2, 19.8, 20.7, 22.2, and 25.0.

6. The crystalline form of claim 1, wherein the X-ray powder diffraction pattern comprises peak positions, in degrees 2-theta (±0.2 degrees 2-theta), of 11.7, 12.8, 14.2, 17.8, 19.8, 20.7, 21.8, 22.2, and 25.0.

7. The crystalline form of claim 1, wherein the crystalline form is characterized by a differential scanning calorimetry thermogram comprising endothermic peaks having an onset temperature of 221.9° C. (±5.0° C.).

8. A pharmaceutical composition comprising a therapeutically effective amount of the crystalline form of claim 1, and one or more pharmaceutical excipients.

9. A method for treating a cancer characterized by the presence of an IDH1 or IDH2 mutation in a patient in need thereof, comprising administering to the patient a therapeutically effective amount of the crystalline form of claim 1.

10. The method of claim 9, wherein the cancer is characterized by the presence of an IDH1 mutation.

11. The method of claim 10, wherein the IDH1 mutation is an R132X mutation.

12. The method of claim 11, wherein the IDH1 mutation is an R132H or R132C mutation.

13. The method of claim 9, wherein the cancer is characterized by the presence of an IDH2 mutation.

14. The method of claim 13, wherein the IDH2 mutation is an R140X mutation.

15. The method of claim 14, wherein the IDH2 mutation is an R140Q, R140W, or R140L mutation.

16. The method of claim 13, wherein the IDH2 mutation is an R172X mutation.

17. The method of claim 16, wherein the IDH2 mutation is an R172K or R172G mutation.

18. The method of claim 9, wherein the cancer is selected from glioma, acute myelogenous leukemia, sarcoma, melanoma, non-small cell lung cancer (NSCLC), cholangiocarcinomas, chondrosarcoma, myelodysplastic syndromes (MDS), myeloproliferative neoplasm (MPN), colon cancer, and angio-immunoblastic non-Hodgkin's lymphoma (NHL).

19. The method of claim 18, wherein the cancer is glioma.

20. The method of claim 19, wherein the glioma is a low grade glioma or a secondary high grade glioma.

21. The method of claim 19, wherein the glioma is a low grade glioma.

22. The method of claim 19, wherein the glioma is a secondary high grade glioma, and the secondary high grade glioma is glioblastoma.

23. The method of claim 9, wherein the cancer is refractory or relapsed.

24. The method of claim 9, wherein the cancer is newly diagnosed or previously untreated.

25. The method of claim 9, wherein the crystalline form is administered to the patient in combination with an additional therapy.

26. The method of claim 9, wherein the patient was previously administered a cancer therapy for the cancer.

27. The method of claim 9, wherein the crystalline form is administered to the patient at a daily dose of about 10 mg, about 25 mg, about 50 mg, about 100 mg, about 200 mg, or about 300 mg of the compound of formula (I).

28. The method of claim 9, wherein the crystalline form is administered to the patient at a dose of about 10 mg or about 50 mg of the compound of formula (I) twice per day.

* * * * *